(12) United States Patent
Perez et al.

(10) Patent No.: US 12,384,751 B2
(45) Date of Patent: Aug. 12, 2025

(54) ALLOSTERIC ACTIVATORS OF THE ALPHA$_{1A}$-ADRENERGIC RECEPTOR

(71) Applicant: The Cleveland Clinic Foundation, Cleveland, OH (US)

(72) Inventors: Dianne M. Perez, Cleveland, OH (US); Shaun R. Stauffer, Cleveland, OH (US); Jonathan Macdonald, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 888 days.

(21) Appl. No.: 17/605,801

(22) PCT Filed: Apr. 23, 2020

(86) PCT No.: PCT/US2020/029583
§ 371 (c)(1),
(2) Date: Oct. 22, 2021

(87) PCT Pub. No.: WO2020/219720
PCT Pub. Date: Oct. 29, 2020

(65) Prior Publication Data
US 2022/0227717 A1  Jul. 21, 2022

Related U.S. Application Data

(60) Provisional application No. 62/837,565, filed on Apr. 23, 2019.

(51) Int. Cl.
| | | |
|---|---|---|
| *C07D 249/04* | (2006.01) | |
| *A61K 31/415* | (2006.01) | |
| *A61K 31/4164* | (2006.01) | |
| *A61K 31/4192* | (2006.01) | |
| *A61K 45/06* | (2006.01) | |
| *C07D 231/12* | (2006.01) | |
| *C07D 233/06* | (2006.01) | |

(52) U.S. Cl.
CPC .......... *C07D 249/04* (2013.01); *A61K 31/415* (2013.01); *A61K 31/4164* (2013.01); *A61K 31/4192* (2013.01); *A61K 45/06* (2013.01); *C07D 231/12* (2013.01); *C07D 233/06* (2013.01)

(58) Field of Classification Search
CPC ................................................. C07D 249/04
See application file for complete search history.

(56) References Cited

U.S. PATENT DOCUMENTS

| | | | |
|---|---|---|---|
| 5,952,362 | A | 9/1999 | Cournoyer et al. |
| 6,057,349 | A | 5/2000 | Cournoyer et al. |
| 2002/0086057 | A1 | 7/2002 | Odink et al. |
| 2004/0170689 | A1 | 9/2004 | Odink et al. |
| 2005/0154041 | A1 | 7/2005 | Michel et al. |
| 2009/0227560 | A1 | 9/2009 | Kuroita et al. |
| 2014/0336165 | A1 | 11/2014 | Hondo et al. |
| 2019/0062281 | A1 | 2/2019 | Schiltz et al. |

FOREIGN PATENT DOCUMENTS

| | | |
|---|---|---|
| EM | 1341529 | 9/2003 |
| EP | 1682110 | 7/2006 |
| EP | 0887346 | 12/2007 |
| JP | 2007509897 | 4/2007 |
| WO | WO 96/16951 A1 | 6/1996 |
| WO | WO 2002/038133 | 5/2002 |
| WO | WO 2005/046664 | 5/2005 |
| WO | WO 2009/003868 A2 | 1/2009 |
| WO | WO 2012/123311 A1 | 9/2012 |
| WO | WO 2019/134985 A1 | 7/2019 |

OTHER PUBLICATIONS

International Search Report and Written Opinion for PCT/US20/29583. Mailed Aug. 31, 2020. 18 pages.
Allegretti et al., Allosteric Modulation of Chemoattractant Receptors. Front Immunol. May 2, 2016;7:170. 7 pages.
Alsene et al., Disruption of prepulse inhibition after stimulation of central but not peripheral alpha-1 adrenergic receptors. Neuropsychopharmacology. Oct. 2006;31(10):2150-61.
Arnsten et al., The alpha-1 adrenergic agonist, cirazoline, impairs spatial working memory performance in aged monkeys. Pharmacol Biochem Behav. Sep. 1997;58(1):55-9.
Attar et al., A shortened Barnes maze protocol reveals memory deficits at 4-months of age in the triple-transgenic mouse model of Alzheimer's disease. PLoS One. Nov. 13, 2013;8(11):e80355. 9 pages.
Auffret et al., Progressive age-related impairment of the late long-term potentiation in Alzheimer's disease presenilin-1 mutant knock-in mice. J Alzheimers Dis. 2010;19(3):1021-33.
Azami et al., Involvement of dorsal hippocampal alpha-adrenergic receptors in the effect of scopolamine on memory retrieval in inhibitory avoidance task. Neurobiol Learn Mem. May 2010;93(4):455-62.
Bermingham-Mcdonogh et al., Reduced anion-binding affinity of Cu,Zn superoxide dismutases chemically modified at arginine. Biochem Biophys Res Commun. Oct. 29, 1982;108(4):1376-82.
Billings et al., Intraneuronal Abeta causes the onset of early Alzheimer's disease-related cognitive deficits in transgenic mice. Neuron. Mar. 3, 2005;45(5):675-88.
Blech et al., Hydroperoxide anion, HO-2, is an affinity reagent for the inactivation of yeast Cu,Zn superoxide dismutase: modification of one histidine per subunit. Arch Biochem Biophys. Jul. 15, 1983;224(2):579-86.

(Continued)

*Primary Examiner* — Paul V Ward
(74) *Attorney, Agent, or Firm* — Casimir Jones SC; Anne M. Reynolds

(57) ABSTRACT

The present invention relates to compounds that are activators of the Alpha$_{1A}$-Adrenergic Receptor ($\alpha_{1A}$-AR) and methods of using such compounds: for treating neurological conditions, for cardio-protection, and for treating other conditions. In certain embodiments, the $\alpha_{1A}$-AR activator compound is a compound of Formula I. In certain embodiments, the neurological condition is Alzheimer's disease, benign prostatic hyperplasia, memory loss, depression, or Parkinson's disease.

20 Claims, 51 Drawing Sheets

(56) References Cited

OTHER PUBLICATIONS

Blue et al., Pharmacological characteristics of Ro 115-1240, a selective alpha1A/1L-adrenoceptor partial agonist: a potential therapy for stress urinary incontinence. BJU Int. Jan. 2004;93(1):162-70.
Borders et al., Essentiality of the active-site arginine residue for the normal catalytic activity of Cu,Zn superoxide dismutase. Biochem J. Sep. 15, 1985;230(3):771-6.
Borders et al., L-amino acid ethyl ester hydrochlorides: Derivatives for qualitative organic analysis. J. Chem. Educ. 1984, 61, 9, 814-815.
Borders et al., α-Brominated 4-hydroxy-3,5-dinitroacetophenones: Potent inhibitors of the erythrocyte anion transport protein. Bioorganic Chemistry. 1989. vol. 17:1. pp. 96-107.
Bota et al., The effects of female sexual hormones on the expression and function of α1A- and α1D-adrenoceptor subtypes in the late-pregnant rat myometrium. Eur J Pharmacol. Dec. 15, 2015;769:177-84.
Brozoski et al., Cognitive deficit caused by regional depletion of dopamine in prefrontal cortex of rhesus monkey. Science. Aug. 31, 1979;205(4409):929-32.
Burns et al., Reduced lean mass in early Alzheimer disease and its association with brain atrophy. Arch Neurol. Apr. 2010;67(4):428-33.
Buzsaki. Two-stage model of memory trace formation: a role for "noisy" brain states. Neuroscience. 1989;31(3):551-70.
Campbell et al., Homobivalent Conjugation Increases the Allosteric Effect of 9-aminoacridine at the α1-Adrenergic Receptors. Mol Pharmacol. Feb. 2017;91(2):135-144.
Chadwick et al., Amitriptyline-mediated cognitive enhancement in aged 3xTg Alzheimer's disease mice is associated with neurogenesis and neurotrophic activity. PLoS One. 2011;6(6):e21660. 13 pages.
Chapman et al., Impaired synaptic plasticity and learning in aged amyloid precursor protein transgenic mice. Nat Neurosci. Mar. 1999;2(3):271-6.
Christopoulos. Allosteric binding sites on cell-surface receptors: novel targets for drug discovery. Nat Rev Drug Discov. Mar. 2002;1(3):198-210.
Collette et al., Long-term α1B-adrenergic receptor activation shortens lifespan, while α1A-adrenergic receptor stimulation prolongs lifespan in association with decreased cancer incidence. Age (Dordr). 2014;36(4):9675. 10 pages.
Cullen et al., Block of LTP in rat hippocampus in vivo by beta-amyloid precursor protein fragments. Neuroreport. Oct. 20, 1997;8(15):3213-7.
Daly et al., Cellular localization and pharmacological characterization of functioning alpha-1 adrenoceptors by fluorescent ligand binding and image analysis reveals identical binding properties of clustered and diffuse populations of receptors. J Pharmacol Exp Ther. Aug. 1998;286(2):984-90.
Daly et al., Fluorescent ligand binding reveals heterogeneous distribution of adrenoceptors and 'cannabinoid-like' receptors in small arteries. Br J Pharmacol. Feb. 2010;159(4):787-96.
Dekosky et al., Synapse loss in frontal cortex biopsies in Alzheimer's disease: correlation with cognitive severity. Ann Neurol. May 1990;27(5):457-64.
Delacourte et al., The biochemical pathway of neurofibrillary degeneration in aging and Alzheimer's disease. Neurology. Apr. 12, 1999;52(6): 16 pages.
Dickson et al., Correlations of synaptic and pathological markers with cognition of the elderly. Neurobiol Aging. May-Jun. 1995;16(3):285-98; discussion 298-304.
Doze et al., Long-term α1A-adrenergic receptor stimulation improves synaptic plasticity, cognitive function, mood, and longevity. Mol Pharmacol. Oct. 2011;80(4):747-58.
Erne et al., Calcium antagonist induced vasodilation in peripheral, coronary and cerebral vasculature as important factors in the treatment of elderly hypertensives. Eur Heart J. Nov. 1987;8 Suppl K:49-56.

Esquerda-Canals et al., Mouse Models of Alzheimer's Disease. J Alzheimers Dis. 2017;57(4):1171-1183.
Ferry et al., Basolateral amygdala noradrenergic influences on memory storage are mediated by an interaction between beta- and alpha1-adrenoceptors. J Neurosci. Jun. 15, 1999;19(12):5119-23.
Ferry et al., Involvement of alpha1-adrenoceptors in the basolateral amygdala in modulation of memory storage. Eur J Pharmacol. May 7, 1999;372(1):9-16.
Flood et al., Hippocampal plasticity in normal aging and decreased plasticity in Alzheimer's disease. Prog Brain Res. 1990;83:435-43.
Gibbs et al., Stimulation of alpha1-adrenoceptors inhibits memory consolidation in the chick. Eur J Neurosci. Oct. 2001;14(8):1369-76.
Grundman. Weight loss in the elderly may be a sign of impending dementia. Arch Neurol. Jan. 2005;62(1):20-2.
Guo et al., Central alpha 1-adrenoceptor stimulation functionally antagonizes the hypnotic response to dexmedetomidine, an alpha 2-adrenoceptor agonist. Anesthesiology. Aug. 1991;75(2):252-6.
Gupta et al., alpha1-Adrenergic receptors regulate neurogenesis and gliogenesis. Mol Pharmacol. Aug. 2009;76(2):314-26.
Hackos et al., Diverse modes of NMDA receptor positive allosteric modulation: Mechanisms and consequences. Neuropharmacology. Jan. 2017;112(Pt A):34-45.
Hamilton et al., Widespread deficits in adult neurogenesis precede plaque and tangle formation in the 3xTg mouse model of Alzheimer's disease. Eur J Neurosci. Sep. 2010;32(6):905-20.
Harley et al., Beta1-adrenoceptor or alpha1-adrenoceptor activation initiates early odor preference learning in rat pups: support for the mitral cell/cAMP model of odor preference learning. Learn Mem. Jan.-Feb. 2006;13(1):8-13.
Hatfield et al., Norepinephrine infused into the basolateral amygdala posttraining enhances retention in a spatial water maze task. Neurobiol Learn Mem. Mar. 1999;71(2):232-9.
Hong et al., A study of alpha-adrenoceptor gene polymorphisms and Alzheimer disease. J Neural Transm (Vienna). 2001;108(4):445-50.
Horie et al., Selectivity of the imidazoline alpha-adrenoceptor agonists (oxymetazoline and cirazoline) for human cloned alpha 1-adrenoceptor subtypes. Br J Pharmacol. Sep. 1995;116(1):1611-8.
Hrometz et al., Expression of multiple alpha1-adrenoceptors on vascular smooth muscle: correlation with the regulation of contraction. J Pharmacol Exp Ther. Jul. 1999;290(1):452-63.
Hwa et al., Chimeras of alpha1-adrenergic receptor subtypes identify critical residues that modulate active state isomerization. J Biol Chem. Apr. 5, 1996;271(14):7956-64.
Hwa et al., Identification of critical determinants of alpha 1-adrenergic receptor subtype selective agonist binding. J Biol Chem. Sep. 29, 1995;270(39):23189-95.
Hwa et al., Synergism of constitutive activity in alpha 1-adrenergic receptor activation. Biochemistry. Jan. 21, 1997;36(3):633-9.
Hwa et al., The unique nature of the serine interactions for alpha 1-adrenergic receptor agonist binding and activation. J Biol Chem. Mar. 15, 1996;271(11):6322-7.
Introini-Collison et al., Involvement of the amygdala in the memory-enhancing effects of clenbuterol. Psychopharmacology (Berl). 1991;104(4):541-4.
Izumi et al., Norepinephrine promotes long-term potentiation in the adult rat hippocampus in vitro. Synapse. Mar. 1, 1999;31(3):196-202.
Jacobsen et al., Early-onset behavioral and synaptic deficits in a mouse model of Alzheimer's disease. Proc Natl Acad Sci U S A. Mar. 28, 2006;103(13):5161-6.
Johnson et al., Characterization of alpha 1-adrenoceptors which increase cyclic AMP accumulation in rat cerebral cortex. Eur J Pharmacol. Oct. 7, 1986;129(3):293-305.
Jones et al., Anatomy of brain α1-adrenergic receptors: in vitro autoradiography with [125I]-heat. J CompNeurol 1985; 231:190-208.
Katsuki et al., Noradrenergic regulation of synaptic plasticity in the hippocampal CA1 region. J Neurophysiol. Jun. 1997;77(6):3013-20.
Kiowski et al., Mechanisms of action and clinical use of calcium antagonists in hypertension. Circulation. Dec. 1989;80(6 Suppl):IV136-44.

(56) References Cited

OTHER PUBLICATIONS

Kiowski. Place of calcium antagonists in the treatment of hypertension. Cor Vasa. 1990;32(2 Suppl 1): 13 pages.
Klyubin et al., Soluble Arctic amyloid beta protein inhibits hippocampal long-term potentiation in vivo. Eur J Neurosci. May 2004;19(10):2839-46.
Kunieda et al., Systemic overexpression of the alpha 1B-adrenergic receptor in mice: an animal model of epilepsy. Epilepsia. Nov. 2002;43(11):1324-9.
Leblanc et al., alpha-Noradrenergic potentiation of neurotransmitter- stimulated cAMP production in rat striatal slices. Brain Res. Feb. 13, 1984;293(1):57-65.
Leppik et al., Allosteric interactions between the antagonist prazosin and amiloride analogs at the human alpha(1A)-adrenergic receptor. Mol Pharmacol. Mar. 2000;57(3):436-45.
Liang et al., Involvement of amygdala pathways in the influence of post-training intra-amygdala norepinephrine and peripheral epinephrine on memory storage. Brain Res. Feb. 5, 1990;508(2):225-33.
Liang et al., Modulating effects of posttraining epinephrine on memory: involvement of the amygdala noradrenergic system. Brain Res. Mar. 12, 1986;368(1):125-33.
Lin et al., Phosphorylation of the CAMP response element-binding protein and activation of transcription by alpha1 adrenergic receptors. J Biol Chem. Nov. 6, 1998;273(45):30033-8.
Lynch et al., Variations in synaptic plasticity and types of memory in corticohippocampal networks. J Cogn Neurosci. Summer 1992;4(3):189-99.
Masliah et al., Altered expression of synaptic proteins occurs early during progression of Alzheimer's disease. Neurology. Jan. 9, 2001;56(1):127-9.
Mccune et al., Bulk is a determinant of oxymetazoline affinity for the alpha1A-adrenergic receptor. Recept Channels. 2004;10(3-4):109-16.
Middei et al., Learning discloses abnormal structural and functional plasticity at hippocampal synapses in the APP23 mouse model of Alzheimer's disease. Learn Mem. Apr. 19, 2010;17(5):236-40.
Minneman et al., Selectivity of agonists for cloned alpha 1-adrenergic receptor subtypes. Mol Pharmacol. Nov. 1994;46(5):929- 36.
Modiri et al., Selectivity of oxymetazoline for urethral pressure vs blood pressure in the anaesthetized female rabbit. Scand J Urol Nephrol. Jun. 2000;34(3):151-6.
Moshfegh et al., Involvement of dorsal hippocampal α1-adrenergic receptors in the effect of WIN55,212-2 on memory retrieval in inhibitory avoidance task. Neurosci Lett. Feb. 4, 2011;489(2):69-73.
Musselman et al., A randomized crossover study to evaluate Ro 115-1240, a selective alpha1A/1L-adrenoceptor partial agonist in women with stress urinary incontinence. BJU Int. Jan. 2004;93(1):78-83.
Nicoll et al., Contrasting properties of two forms of long-term potentiation in the hippocampus. Nature. Sep. 14, 1995;377(6545):115-8.
Oddo et al., Amyloid deposition precedes tangle formation in a triple transgenic model of Alzheimer's disease. Neurobiol Aging. Dec. 2003;24(8):1063-70.
Ondrejcak et al., Alzheimer's disease amyloid beta-protein and synaptic function. Neuromolecular Med. Mar. 2010;12(1):13-26.
Ono et al., BODIPY-based molecular probe for imaging of cerebral β-amyloid plaques. ACS Chem Neurosci. Apr. 18, 2012;3(4):319-24.
Papay et al., Localization of the mouse alpha1A-adrenergic receptor (AR) in the brain: alpha1AAR is expressed in neurons, GABAergic interneurons, and NG2 oligodendrocyte progenitors. J Comp Neurol. Jul. 10, 2006;497(2):209-22.
Papay et al., Mice expressing the alpha(1B)-adrenergic receptor induces a synucleinopathy with excessive tyrosine nitration but decreased phosphorylation. J Neurochem. Nov. 2002;83(3):623-34.
Perez et al., Cardiac and neuroprotection regulated by α(1)-adrenergic receptor subtypes. J Recept Signal Transduct Res. Apr. 2011;31(2):98-110.
Perez et al., Cloning, expression, and tissue distribution of the rat homolog of the bovine alpha 1C-adrenergic receptor provide evidence for its classification as the alpha 1A subtype. Mol Pharmacol. Nov. 1994;46(5):823-31.
Perez et al., Constitutive activation of a single effector pathway: evidence for multiple activation states of a G protein-coupled receptor. Mol Pharmacol. Jan. 1996;49(1):112-22.
Perez et al., Solution-phase library screening for the identification of rare clones: isolation of an alpha 1D-adrenergic receptor cDNA. Mol Pharmacol. Dec. 1991;40(6):876-83.
Perez. Structure-function of alpha1-adrenergic receptors. Biochem Pharmacol. Apr. 15, 2007;73(8):1051-62.
Perkins et al., Characterization of the adrenergic receptors mediating a rise in cyclic 3'-5'-adenosine monophosphate in rat cerebral cortex. J Pharmacol Exp Ther. May 1973;185(2):371-8.
Piascik et al., The specific contribution of the novel alpha-1D adrenoceptor to the contraction of vascular smooth muscle. J Pharmacol Exp Ther. Dec. 1995;275(3):1583-9.
Pigini et al., Structure-activity relationship at alpha-adrenergic receptors within a series of imidazoline analogues of cirazoline. Bioorg Med Chem. May 2000;8(5):883-8.
Porter et al., Activation of the alpha1b-adrenergic receptor is initiated by disruption of an interhelical salt bridge constraint. J Biol Chem. Nov. 8, 1996;271(45):28318-23.
Porter et al., The agonism and synergistic potentiation of weak partial agonists by triethylamine in alpha 1-adrenergic receptor activation: evidence for a salt bridge as the initiating process. Mol Pharmacol. Apr. 1998;53(4):766-71.
PubChem-CID-117052137, Create Date: Jan. 30, 2016. 7 pages.
PubChem-CID-66749667, Create Date: Nov. 30, 2012, 8 pages.
Pussinen et al., Minor role for alpha1-adrenoceptors in the facilitation of induction and early maintenance of long-term potentiation in the CA1 field of the hippocampus. J Neurosci Res. Feb. 1, 1998;51(3):309-15.
Puumala et al., Effects of St-587 and prazosin on water maze and passive avoidance performance of scopolamine-treated rats. Pharmacol Biochem Behav. Sep. 1996;55(1):107-15.
Puumala et al., Stimulation and blockade of alpha1 adrenoceptors affect behavioural activity, but not spatial working memory assessed by delayed non-matching to position task in rats. J Psychopharmacol. 1997;11(1):45-51.
Puumala et al., Stimulation of alpha-1 adrenergic receptors facilitates spatial learning in rats. Eur Neuropsychopharmacol. Feb. 1998;8(1):17-26.
Ramarao et al., Genomic organization and expression of the human alpha 1B-adrenergic receptor. J Biol Chem. Oct. 25, 1992;267(30):21936-45.
Rokosh et al., Knockout of the alpha 1A/C-adrenergic receptor subtype: the alpha 1A/C is expressed in resistance arteries and is required to maintain arterial blood pressure. Proc Natl Acad Sci U S A. Jul. 9, 2002;99(14):9474-9.
Romberg et al., Impaired attention in the 3xTgAD mouse model of Alzheimer's disease: rescue by donepezil (Aricept). J Neurosci. Mar. 2, 2011;31(9):3500-7.
Rorabaugh et al., alpha1A- but not alpha1B-adrenergic receptors precondition the ischemic heart by a staurosporine-sensitive, chelerythrine-insensitive mechanism. Cardiovasc Res. Feb. 1, 2005;65(2):436-45.
Ruffolo et al., Receptor interactions of imidazolines. IX. Cirazoline is an alpha-1 adrenergic agonist and an alpha-2 adrenergic antagonist. J Pharmacol Exp Ther. Jul. 1982;222(1):29-36.
Rutecki et al., Noradrenergic modulation of epileptiform activity in the hippocampus. Epilepsy Res. Feb. 1995;20(2):125-36.
Scanziani et al., Presynaptic inhibition of excitatory synaptic transmission mediated by alpha adrenergic receptors in area CA3 of the rat hippocampus in vitro. J Neurosci. Dec. 1993;13(12):5393-401.
Scheiderer et al., Coactivation of M(1) muscarinic and alpha1 adrenergic receptors stimulates extracellular signal-regulated protein kinase and induces long-term depression at CA3-CA1 synapses in rat hippocampus. J Neurosci. May 14, 2008;28(20):5350-8.
Scheiderer et al., Novel form of long-term synaptic depression in rat hippocampus induced by activation of alpha 1 adrenergic receptors. J Neurophysiol. Feb. 2004;91(2):1071-7.

(56) References Cited

OTHER PUBLICATIONS

Schmeichel et al., Wake-promoting actions of noradrenergic α1- and β-receptors within the lateral hypothalamic area. Eur J Neurosci. Mar. 2013;37(6):891-900.

Schultz et al., Acummulation of cyclic adenosine 3', 5'-monophosphate in cerebral cortical slices from rat and mouse: stimulatory effect of alpha- and beta-adrenergic agents and adenosine. J Neurochem. Nov. 1973;21(5):1319-26.

Segal et al., Actions of norepinephrine in the rat hippocampus. Prog Brain Res. 1991;88:323-30.

Selkoe. Alzheimer's disease: genes, proteins, and therapy. Physiol Rev. Apr. 2001;81(2):741-66.

Shankar et al., Amyloid-beta protein dimers isolated directly from Alzheimer's brains impair synaptic plasticity and memory. Nat Med. Aug. 2008;14(8):837-42.

Sharpe et al., Allosteric alpha 1-adrenoreceptor antagonism by the conopeptide rho-TIA. J Biol Chem. Sep. 5, 2003;278(36):34451-7.

Shi et al., Novel proteins associated with human dilated cardiomyopathy: selective reduction in α(1A)-adrenergic receptors and increased desensitization proteins. J Recept Signal Transduct Res. Apr. 2013;33(2):96-106.

Shi et al., The role of α1-adrenergic receptors in regulating metabolism: increased glucose tolerance, leptin secretion and lipid oxidation. J Recept Signal Transduct Res. Apr. 2017;37(2):124-132.

Shi et al., α1A-Adrenergic receptor prevents cardiac ischemic damage through PKCδ/GLUT1/4-mediated glucose uptake. J Recept Signal Transduct Res. 2016;36(3):261-70.

Shimohama et al., Biochemical characterization of alpha-adrenergic receptors in human brain and changes in Alzheimer-type dementia. J Neurochem. Oct. 1986;47(4):1295-301.

Sirvio et al., Central alpha1-adrenoceptors: their role in the modulation of attention and memory formation. Pharmacol Ther. Jul. 1999;83(1):49-65.

Song et al., Characterization of cAMP accumulation mediated by three alpha1-adrenoceptor subtypes in HEK293 cells. Acta Pharmacol Sin. Jun. 2003;24(6):549-54.

Sterniczuk et al., Characterization of the 3xTg-AD mouse model of Alzheimer's disease: part 2. Behavioral and cognitive changes. Brain Res. Aug. 12, 2010;1348:149-55.

Stevens et al., Reference and working memory deficits in the 3xTg-AD mouse between 2 and 15-months of age: a cross-sectional study. Behav Brain Res. Feb. 1, 2015;278:496-505.

Stojkov et al., In vivo blockade of α1-adrenergic receptors mitigates stress-disturbed cAMP and cGMP signaling in Leydig cells. Mol Hum Reprod. Jan. 2014;20(1):77-88.

Sze et al., Loss of the presynaptic vesicle protein synaptophysin in hippocampus correlates with cognitive decline in Alzheimer disease. J Neuropathol Exp Neurol. Aug. 1997;56(8):933-44.

Szot et al., Alpha1-adrenoreceptor in human hippocampus: binding and receptor subtype mRNA expression. Brain Res Mol Brain Res. Oct. 3, 2005;139(2):367-71.

Szot et al., Changes in adrenoreceptors in the prefrontal cortex of subjects with dementia: evidence of compensatory changes. Neuroscience. Apr. 25, 2007;146(1):471-80.

Tamura et al., Weight loss in patients with Alzheimer's disease. J Nutr Elder. 2007;26(3-4):21-38.

Targowska-Duda et al., Molecular interactions of type I and type II positive allosteric modulators with the human α7 nicotinic acetylcholine receptor: an in silico study. J Biomol Struct Dyn. Feb. 2019;37(2):411-439.

Thonberg et al., A novel pathway for adrenergic stimulation of cAMP-response-element-binding protein (CREB) phosphorylation: mediation via alpha1-adrenoceptors and protein kinase C activation. Biochem J. May 15, 2002;364(Pt 1):73-9.

Tran et al., Chronic psychosocial stress accelerates impairment of long-term memory and late-phase long-term potentiation in an at-risk model of Alzheimer's disease. Hippocampus. Jul. 2011;21(7):724-32.

Ul Haq et al., Adrenergic modulation of sharp wave-ripple activity in rat hippocampal slices. Hippocampus. Mar. 2012;22(3):516-33.

Vucicevic et al., Prediction of blood-brain barrier permeation of α-adrenergic and imidazoline receptor ligands using PAMPA technique and quantitative-structure permeability relationship analysis. Eur J Pharm Sci. Feb. 20, 2015;68:94-105.

Wang et al., Block of long-term potentiation by naturally secreted and synthetic amyloid beta-peptide in hippocampal slices is mediated via activation of the kinases c-Jun N-terminal kinase, cyclin-dependent kinase 5, and p38 mitogen-activated protein kinase as well as metabotropic glutamate receptor type 5. J Neurosci. Mar. 31, 2004;24(13):3370-8.

Waugh et al., Novel aromatic residues in transmembrane domains IV and V involved in agonist binding at alpha(1a)-adrenergic receptors. J Biol Chem. Apr. 21, 2000;275(16):11698-705.

Waugh et al., Phe-308 and Phe-312 in transmembrane domain 7 are major sites of alpha 1-adrenergic receptor antagonist binding. Imidazoline agonists bind like antagonists. J Biol Chem. Jul. 6, 2001;276(27):25366-71.

Wood et al., Excitatory amino acid signal transduction in the hippocampus: role of noradrenergic afferents and nitric oxide in cGMP increases in vivo. Life Sci. 1992;51(8):601-6.

Zarrindast et al., The role of alpha-adrenoceptors in the amnestic effect of intracerebroventricular dexamethasone. Pharmacol Res. Oct. 2002;46(4):339-44.

Zhao et al., Identification of critical extracellular loop residues involved in alpha 1-adrenergic receptor subtype-selective antagonist binding. Mol Pharmacol. Nov. 1996;50(5):1118-26.

Zhao et al., The third extracellular loop of the beta2-adrenergic receptor can modulate receptor/G protein affinity. Mol Pharmacol. Mar. 1998;53(3):524-9.

Zilles et al., Regional and laminar distributions of alpha 1-adrenoceptors and their subtypes in human and rat hippocampus. Neuroscience. 1991;40(2):307-20.

Zuscik et al., Hypotension, autonomic failure, and cardiac hypertrophy in transgenic mice overexpressing the alpha 1B-adrenergic receptor. J Biol Chem. Apr. 27, 2001;276(17):13738-43.

Zuscik et al., Overexpression of the alpha1B-adrenergic receptor causes apoptotic neurodegeneration: multiple system atrophy. Nat Med. Dec. 2000;6(12):1388-94.

A.

FIGURE 2 (cont'd)
B.
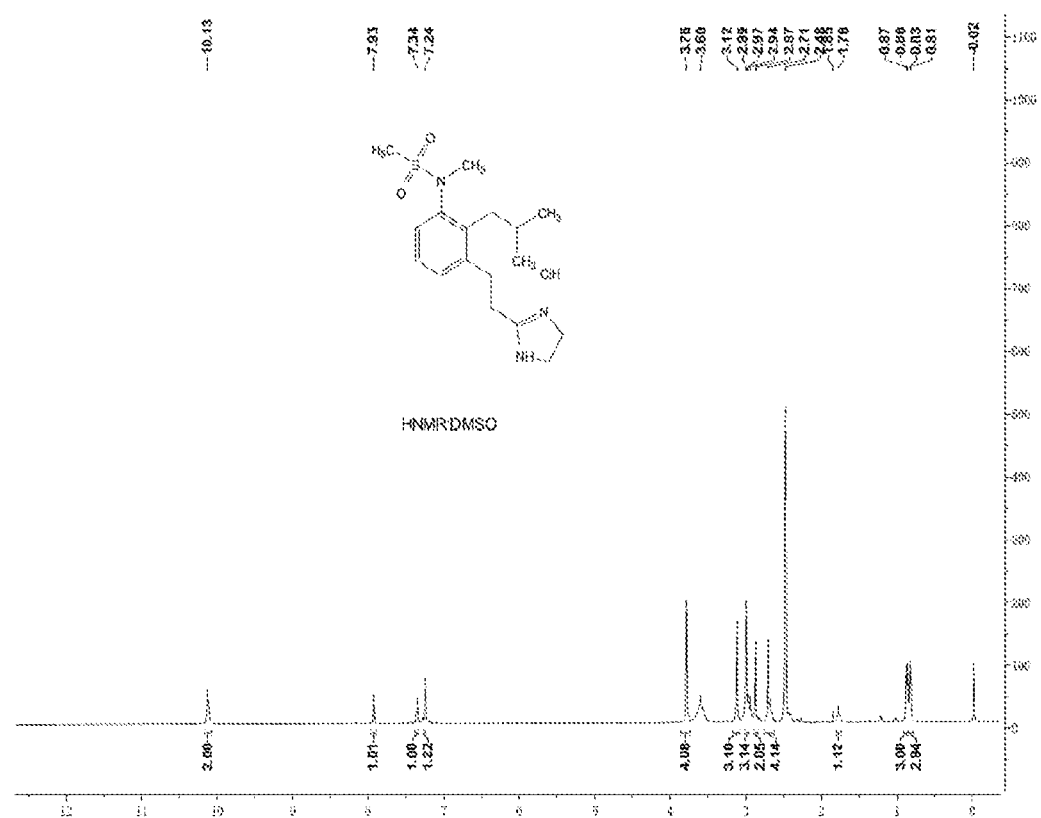
C.
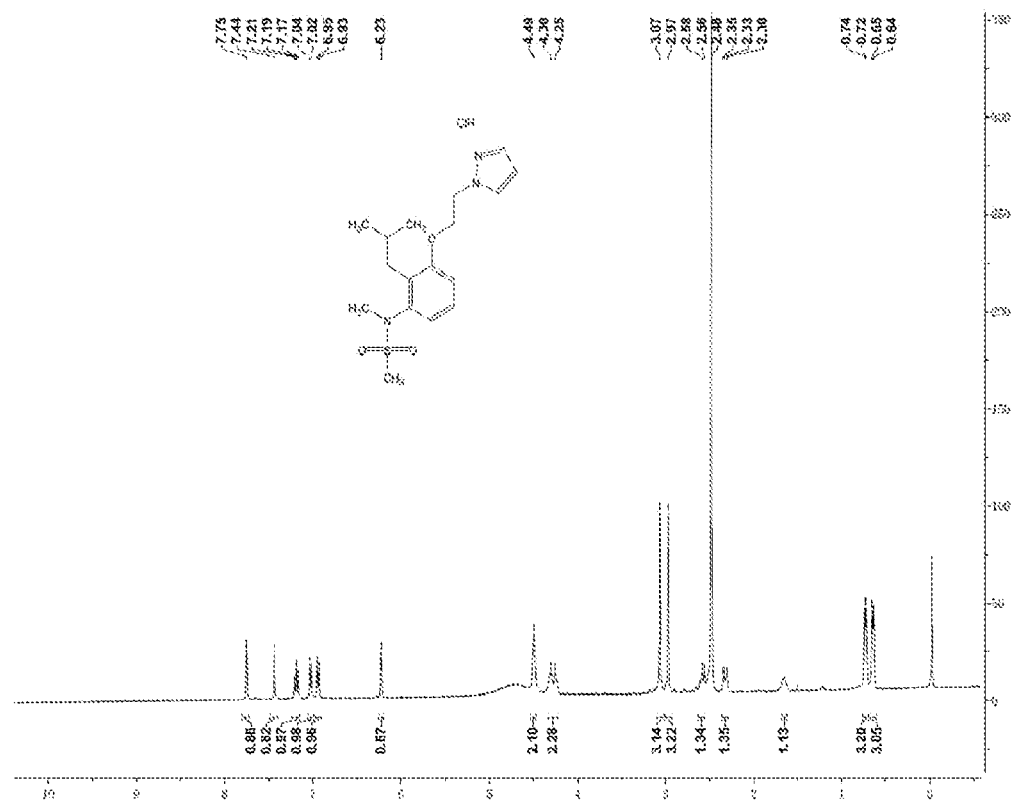

FIGURE 2 (cont'd)
D.
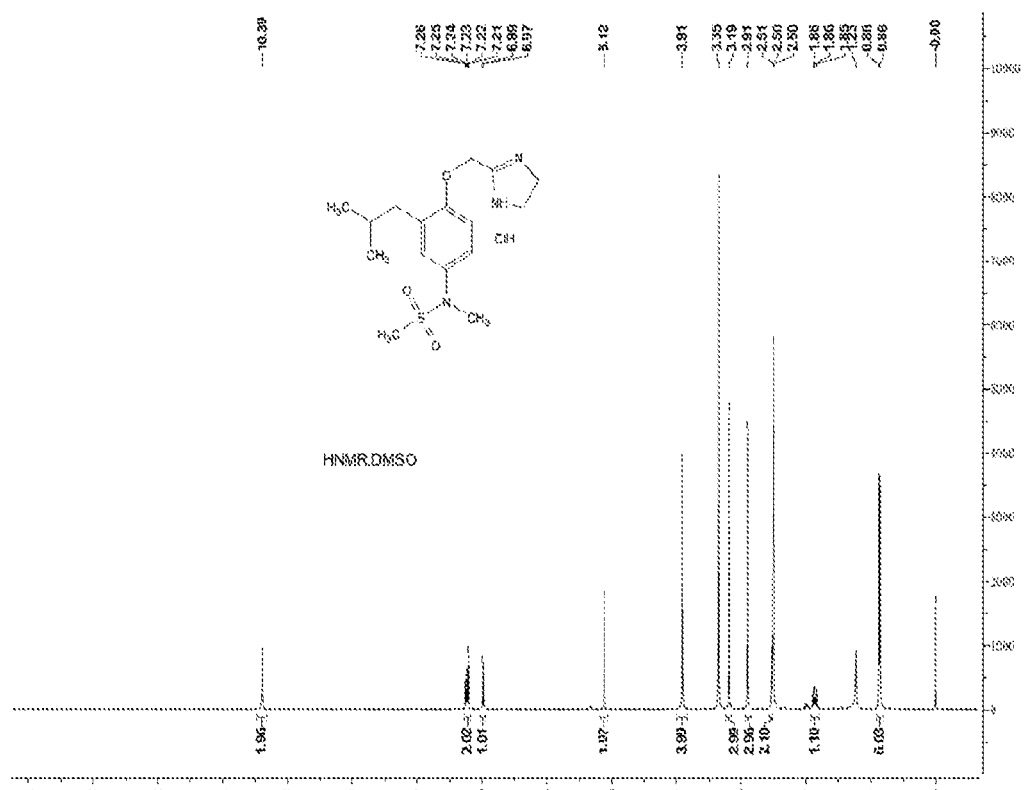
E.
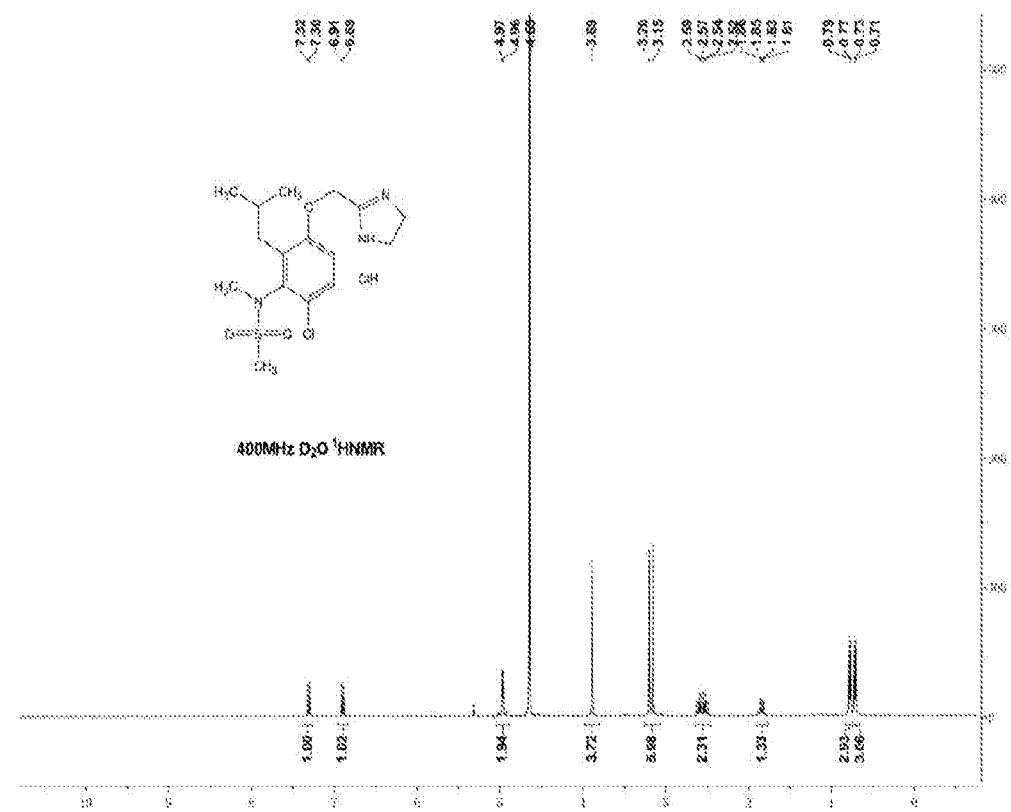

FIGURE 2 (cont'd)
F.
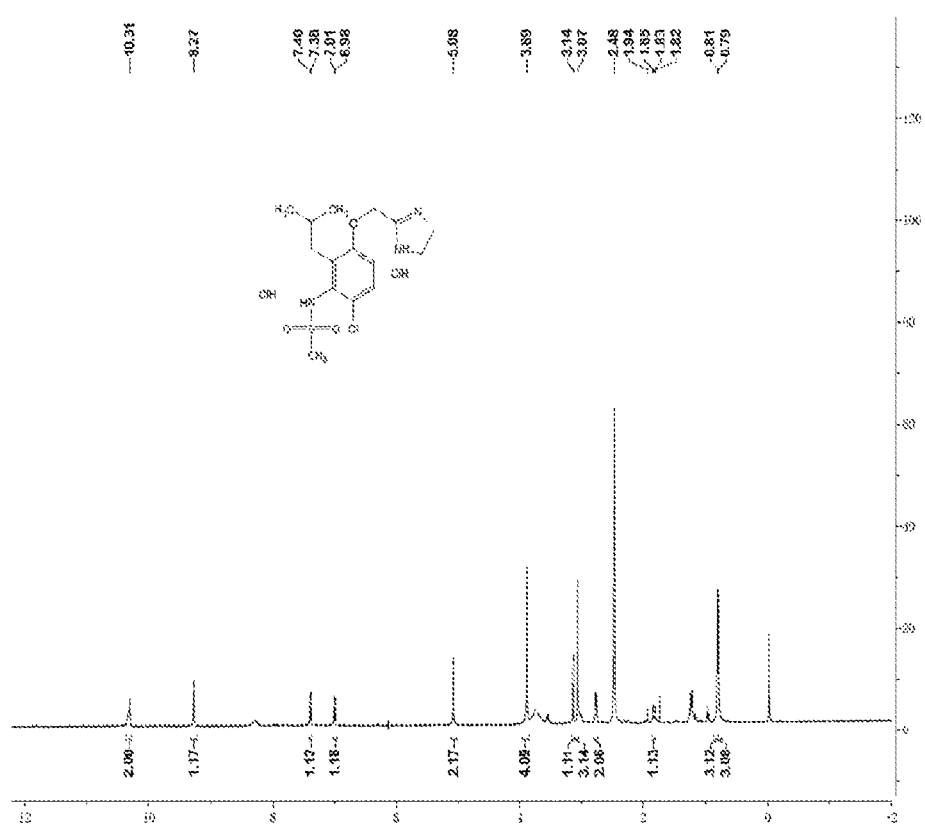
G.
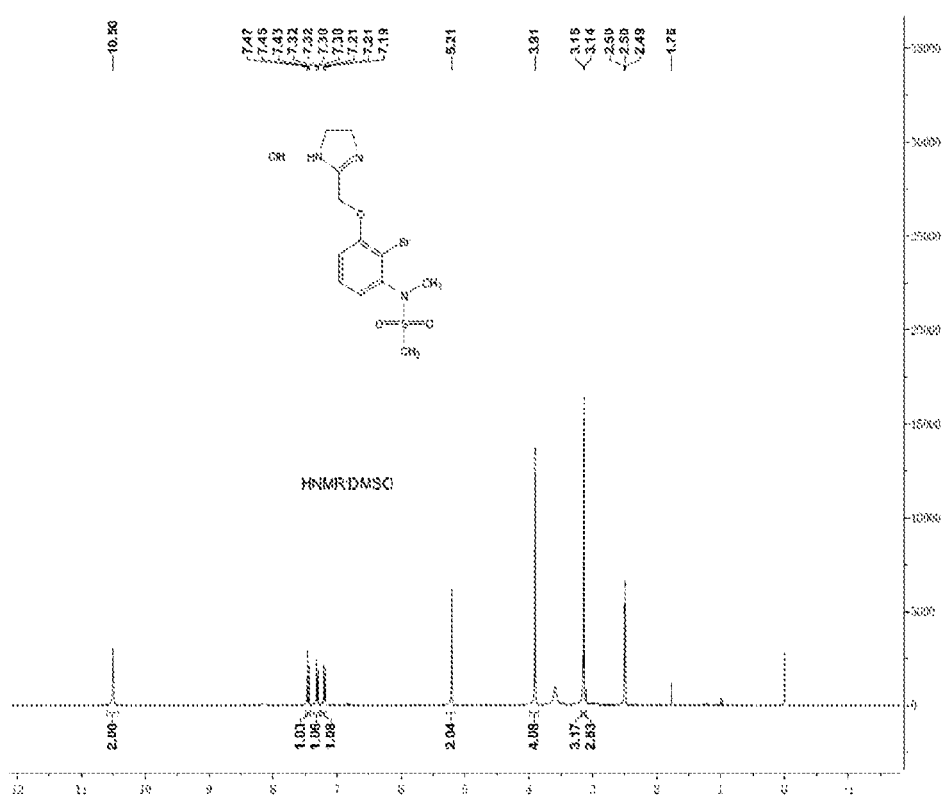

FIGURE 2 (cont'd)
H.
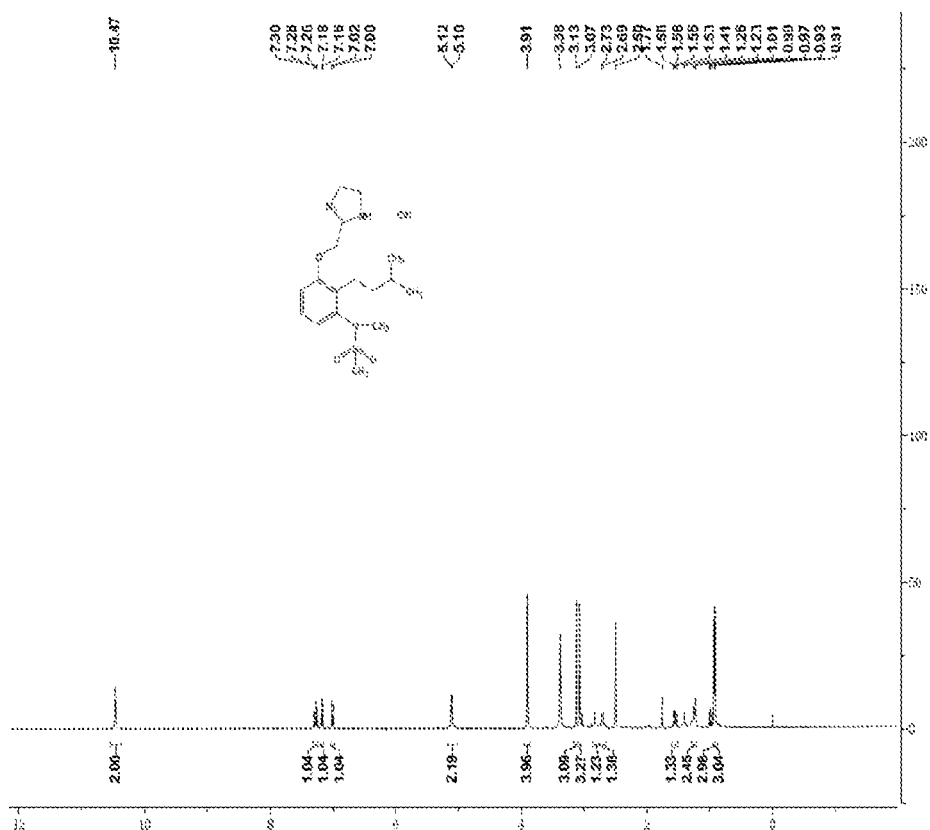
I.
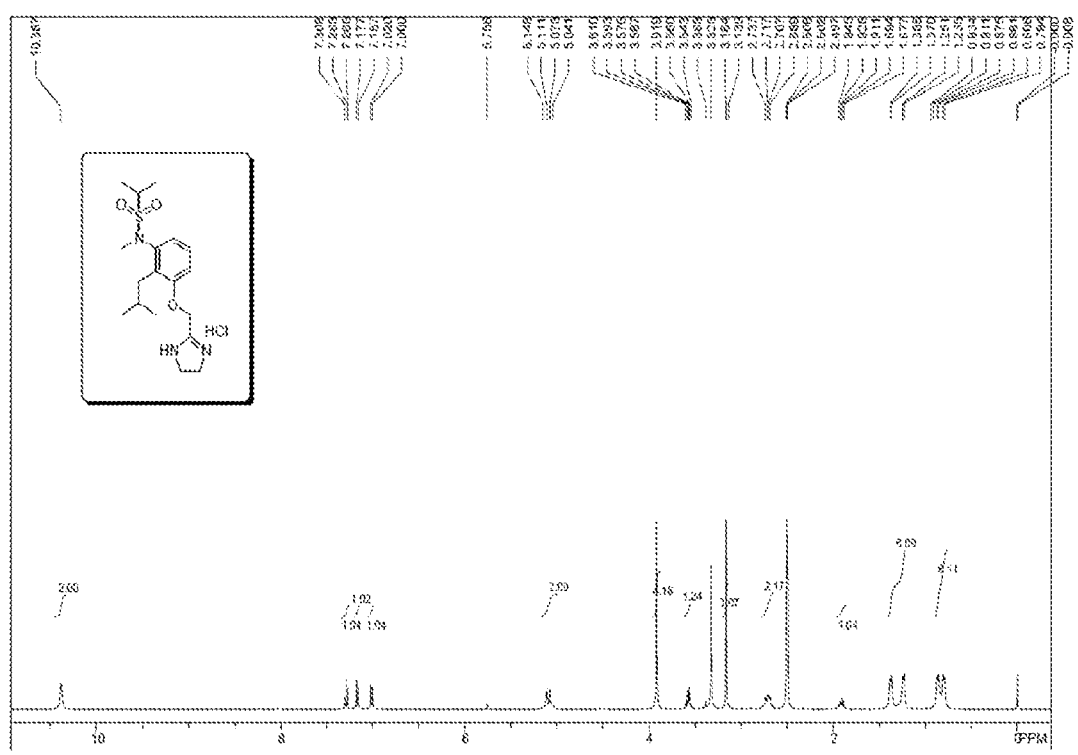

FIGURE 3
A.
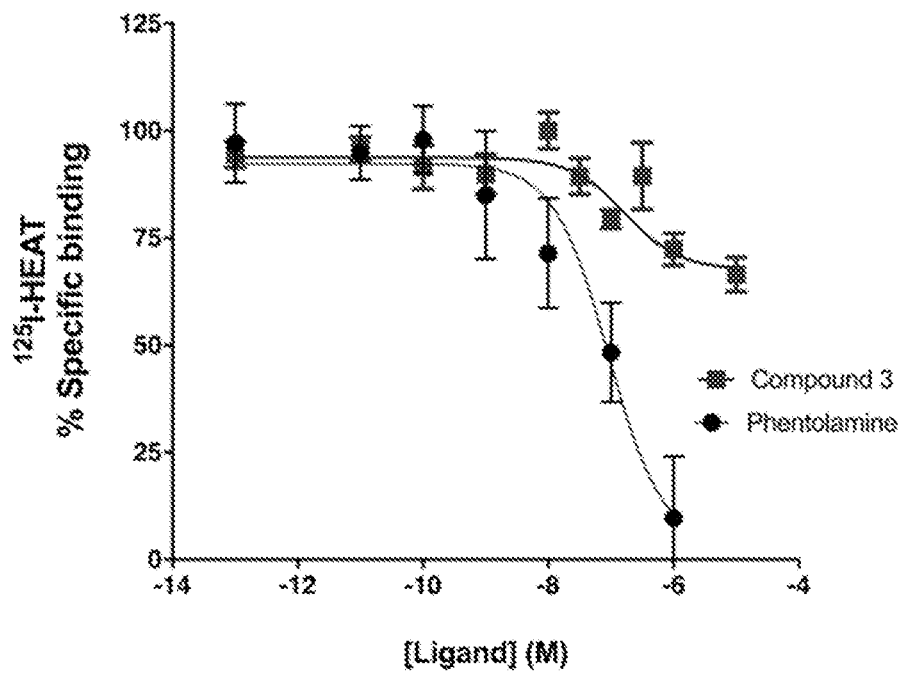
B.
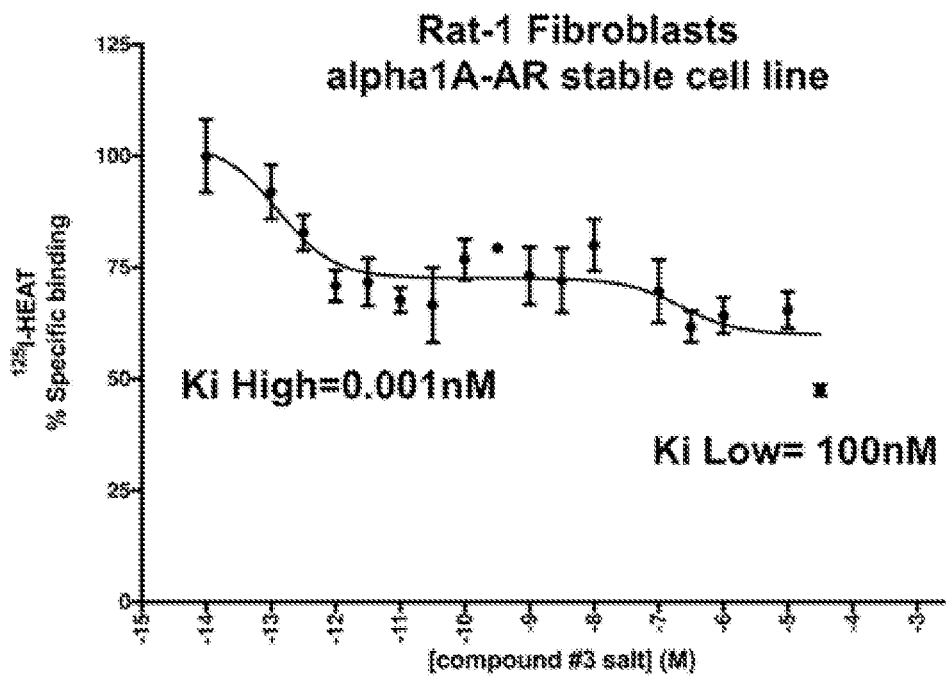

FIGURE 4
A.
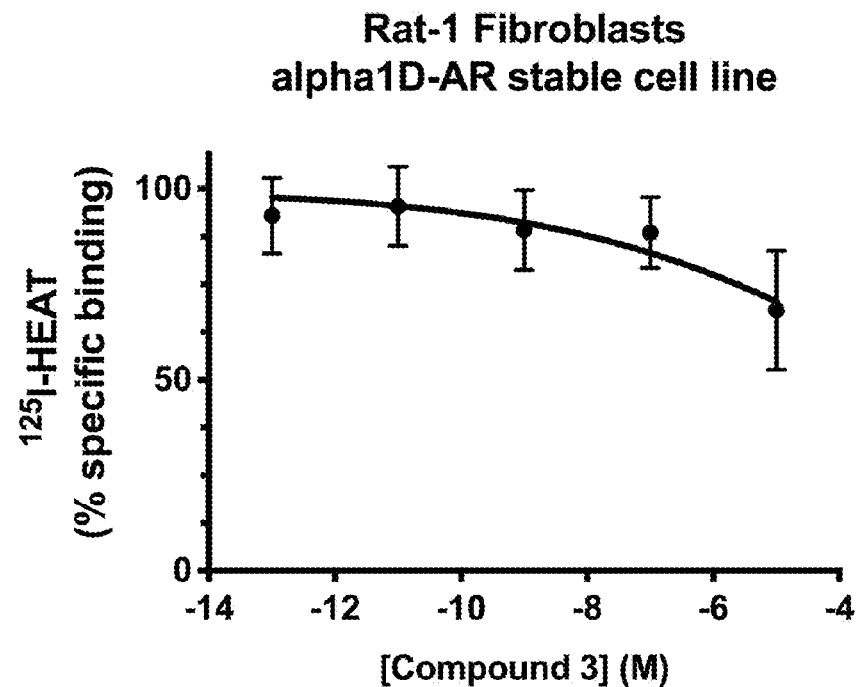
B.
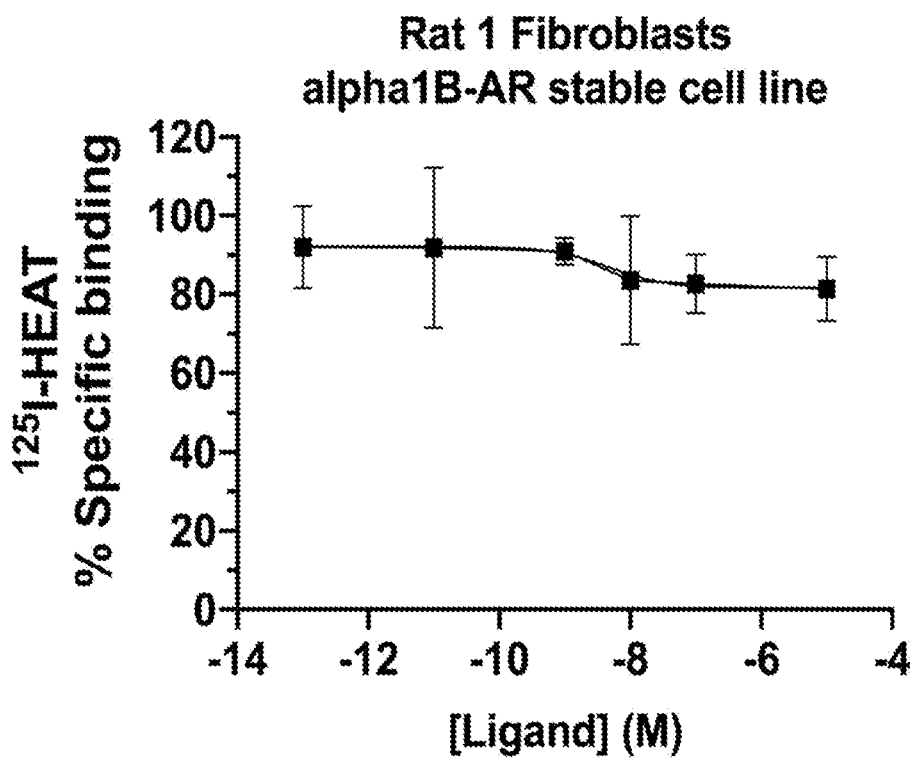

FIGURE 5
A.
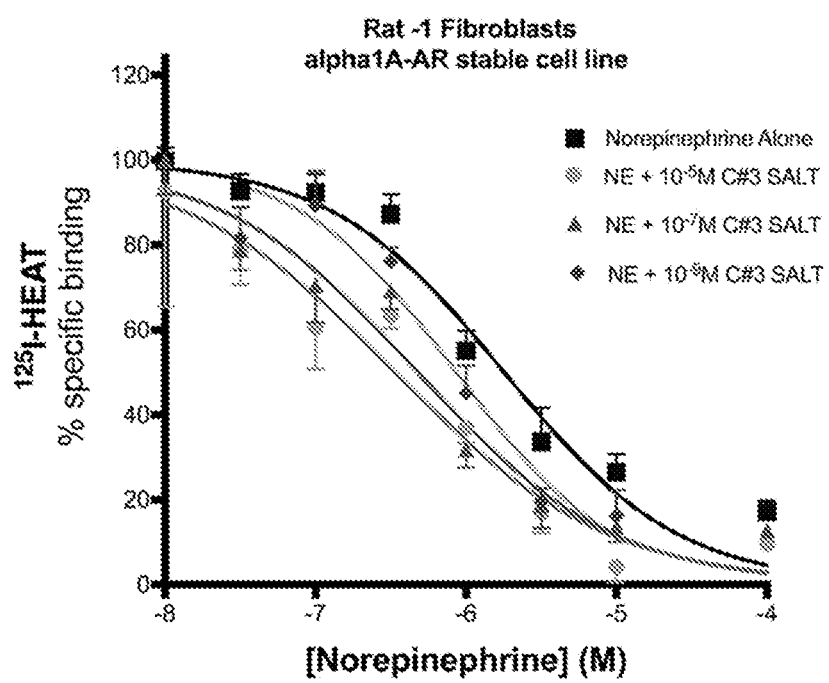
B.
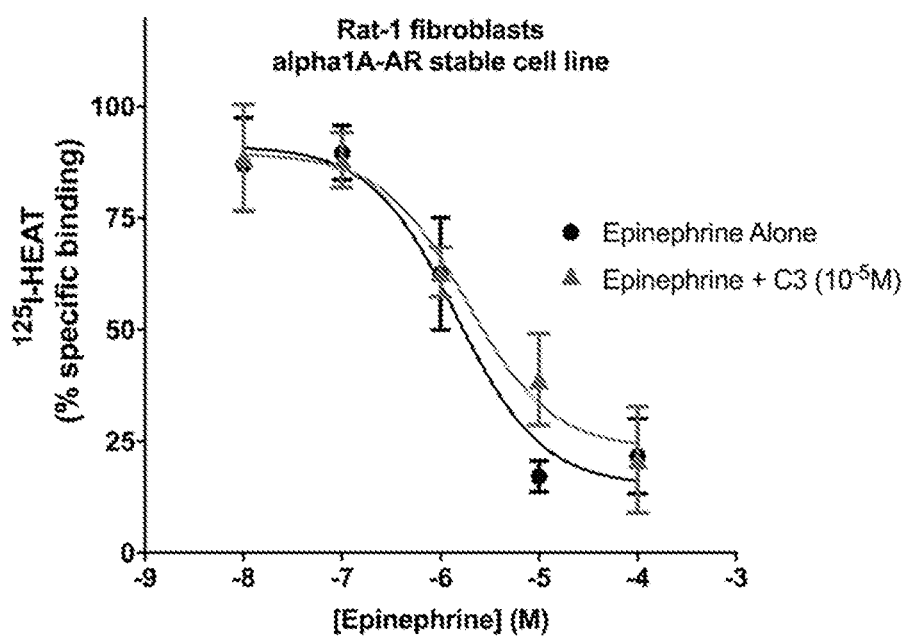

FIGURE 6
A.
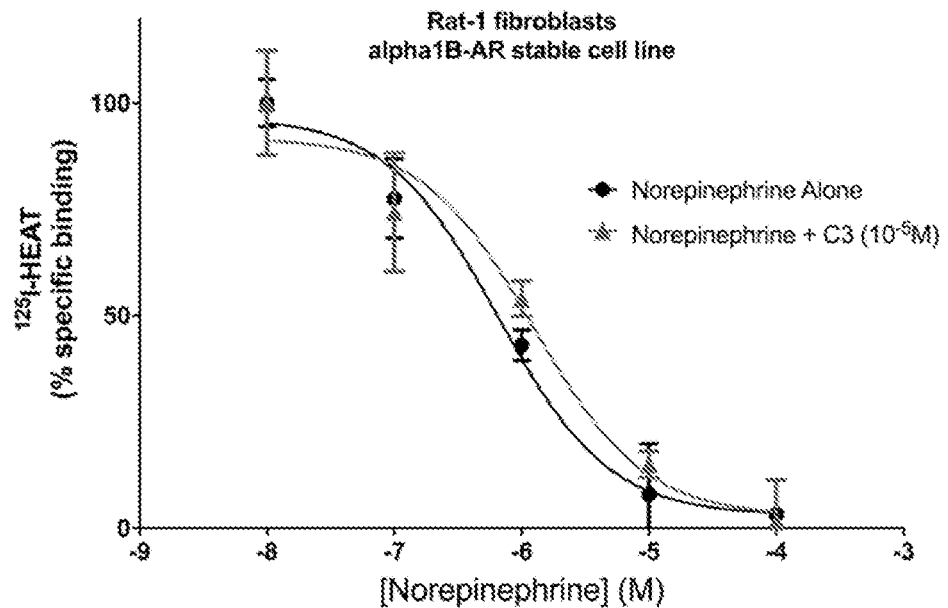
B.
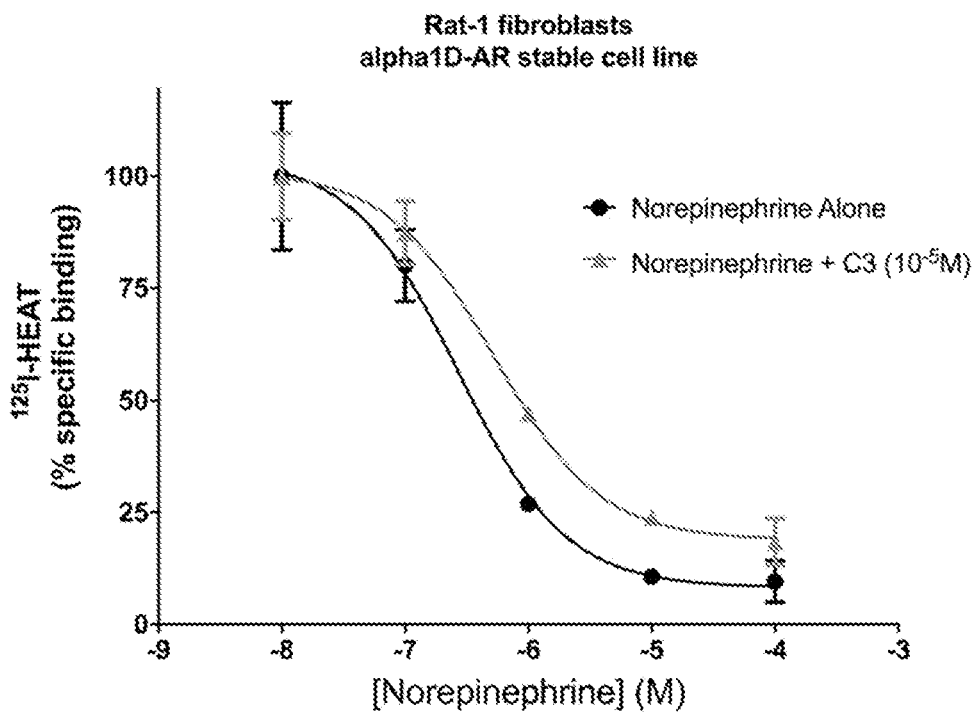

FIGURE 8
A.
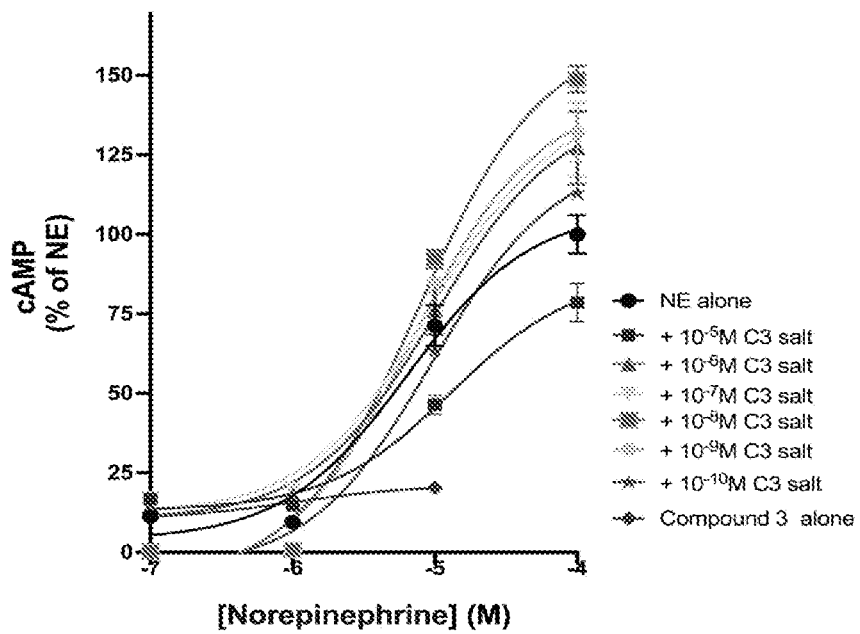
B.
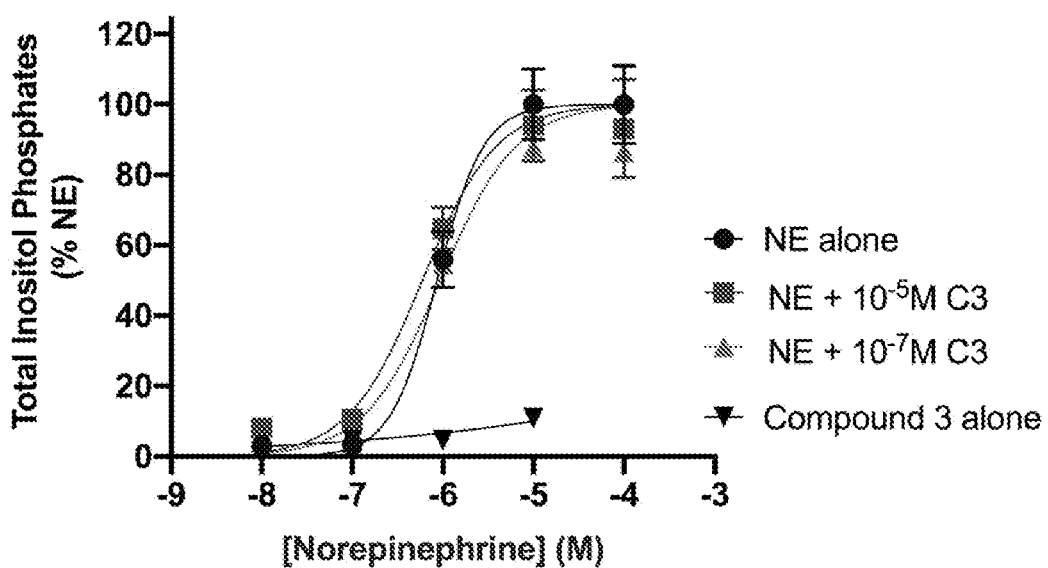

FIGURE 8 (cont'd)
C.
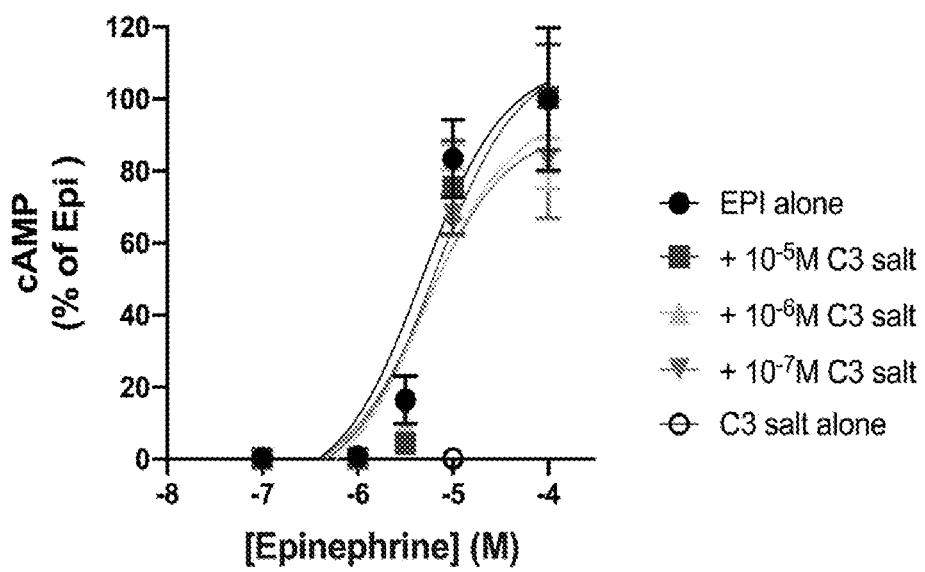
D.
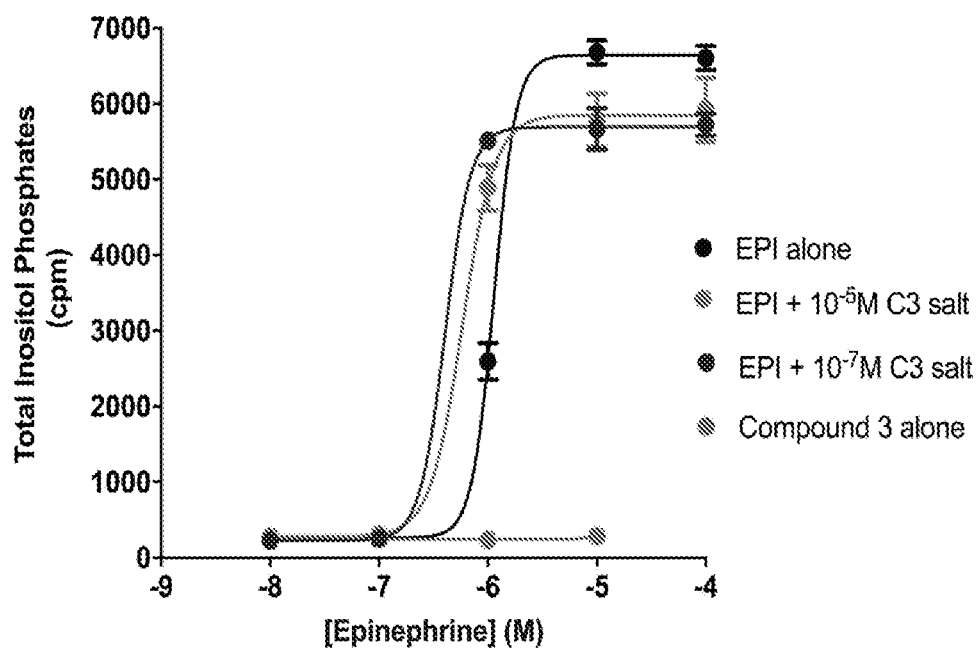

FIGURE 9
A.
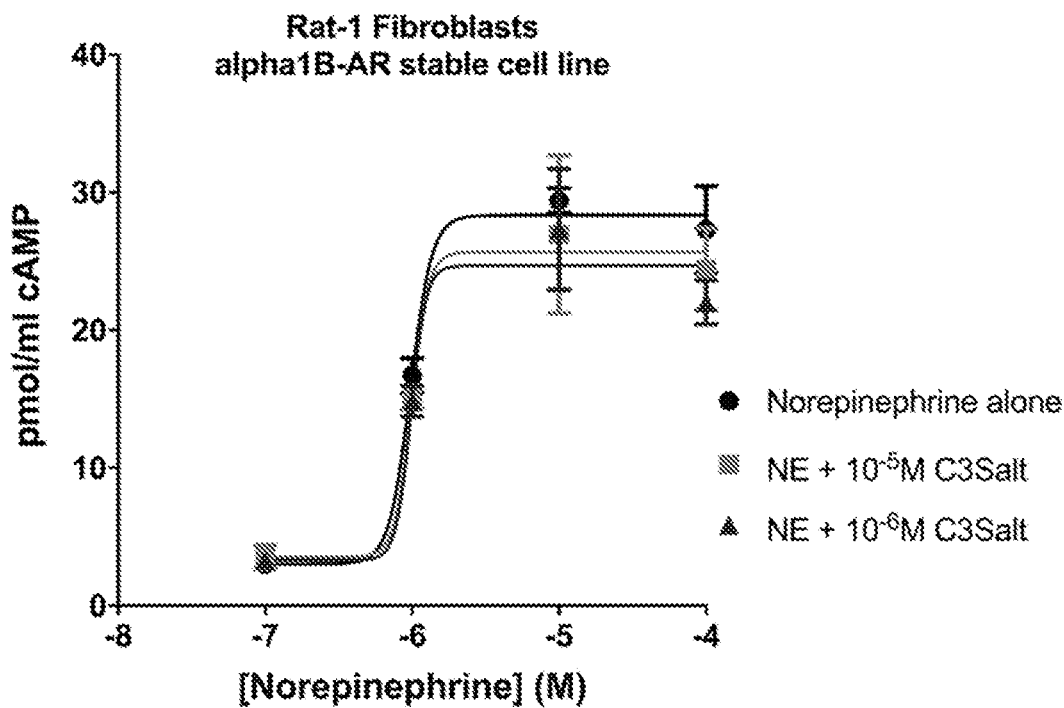
B.
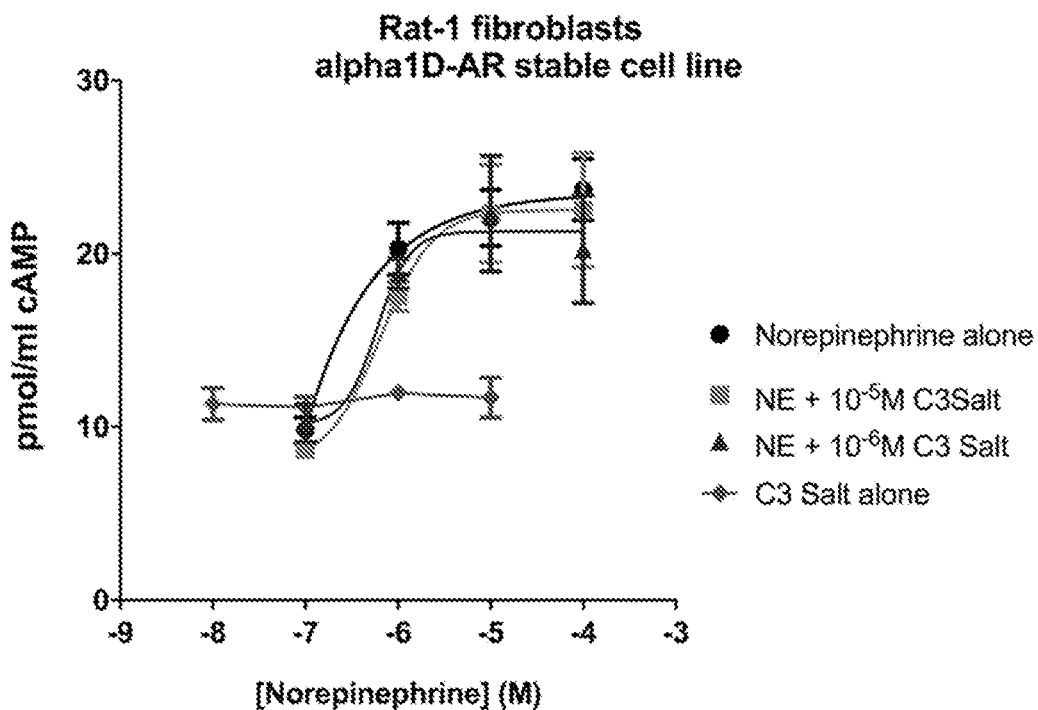

FIGURE 13
A.
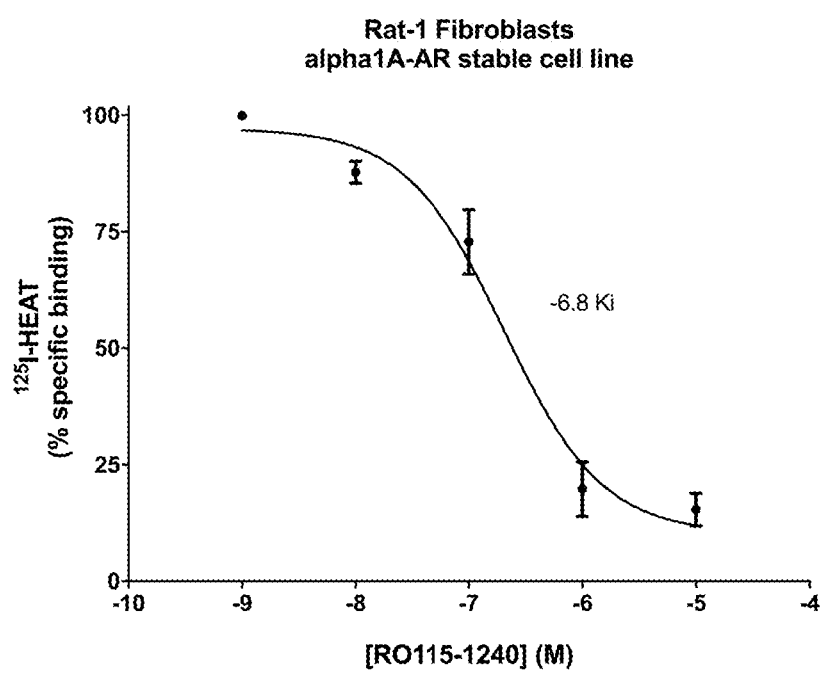
B.
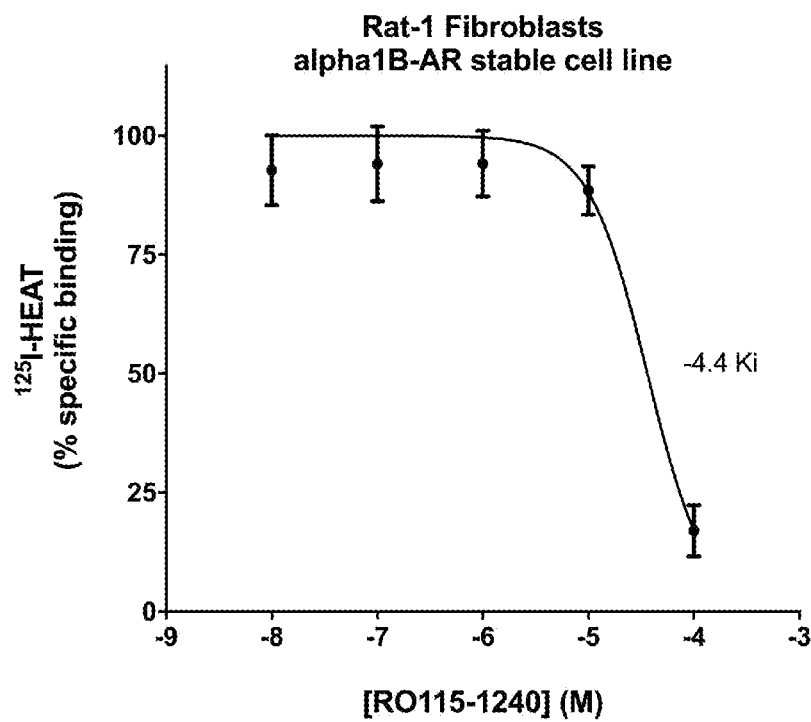

C.

FIGURE 14
A.
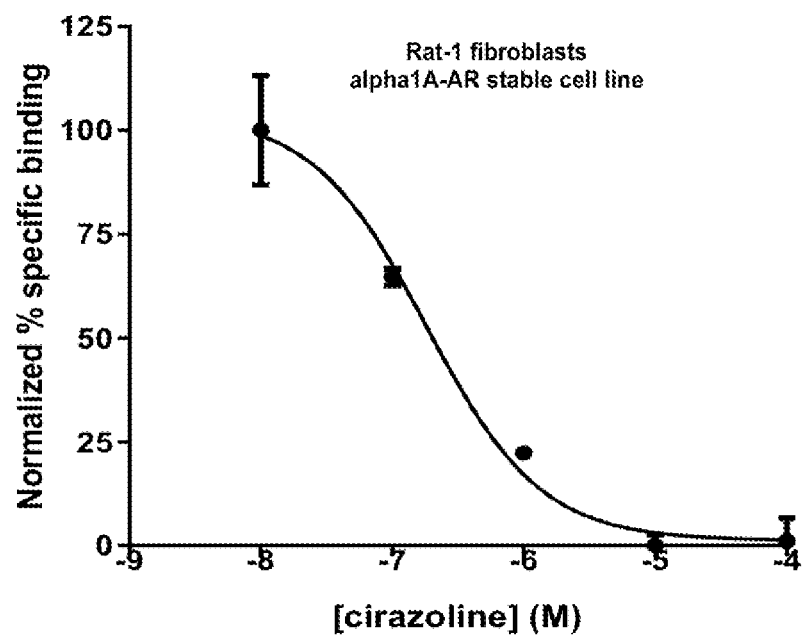
B.
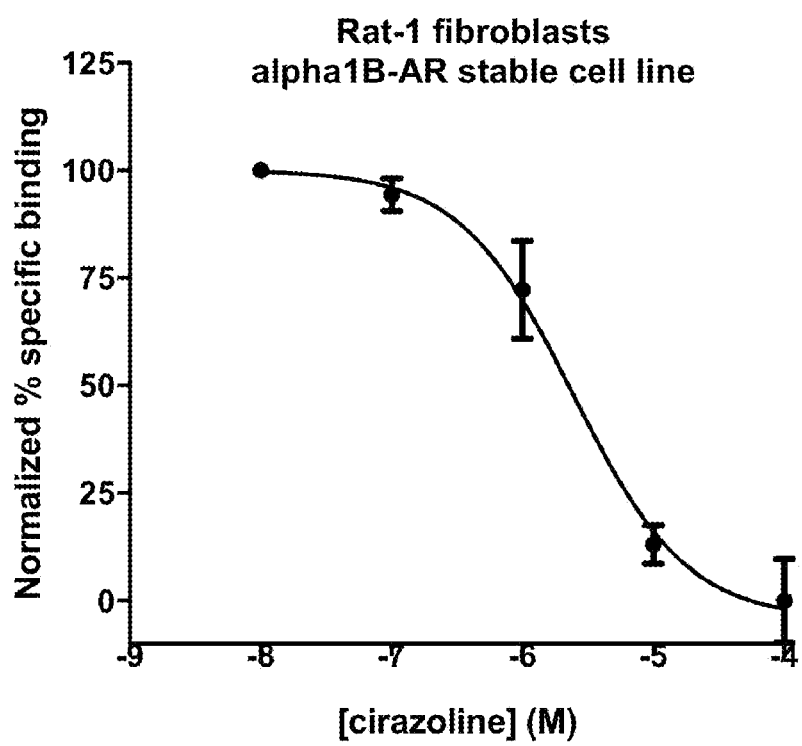

C.

FIGURE 15
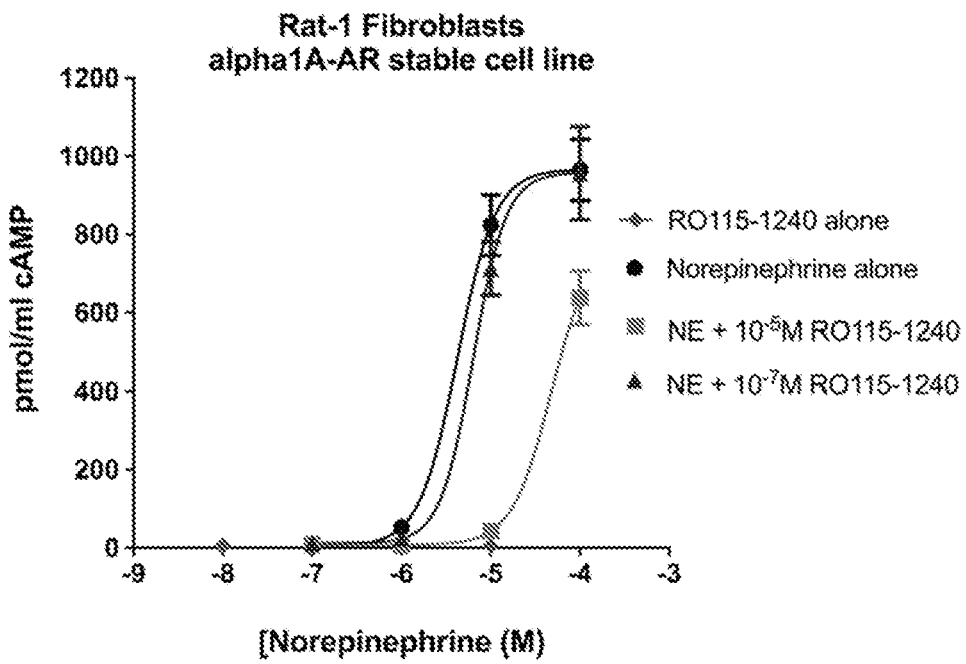
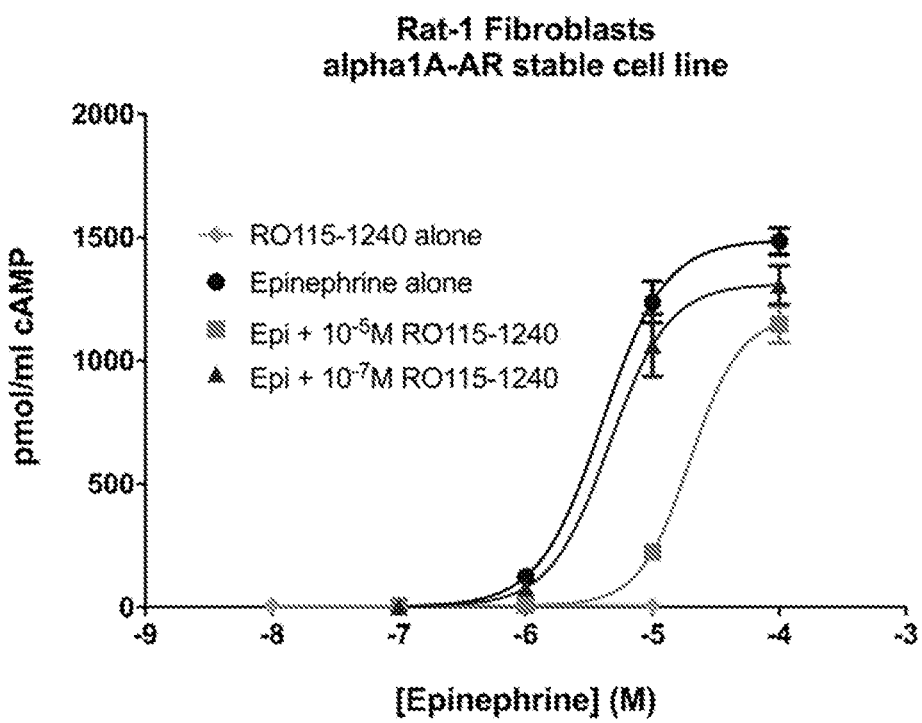

FIGURE 16
A.
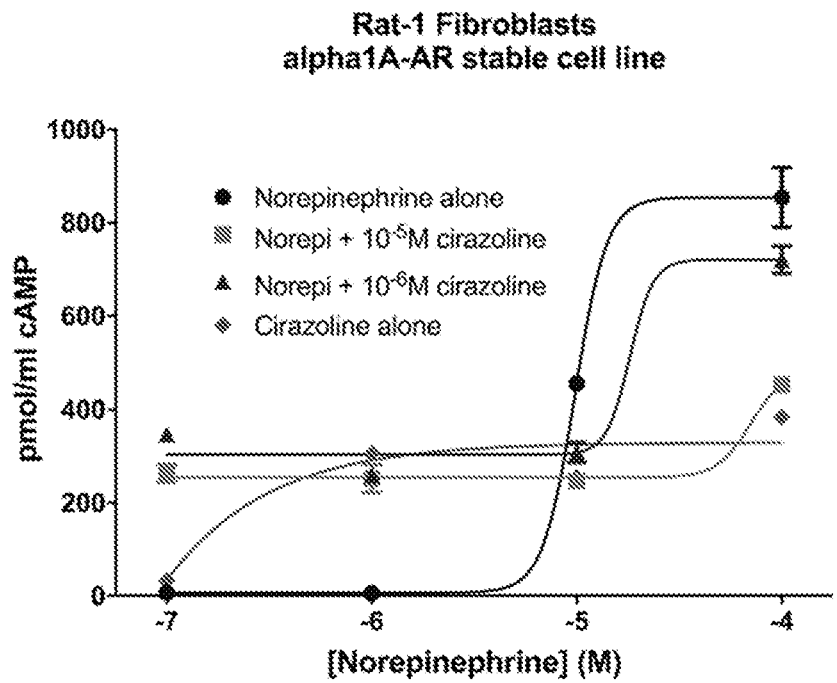
B.
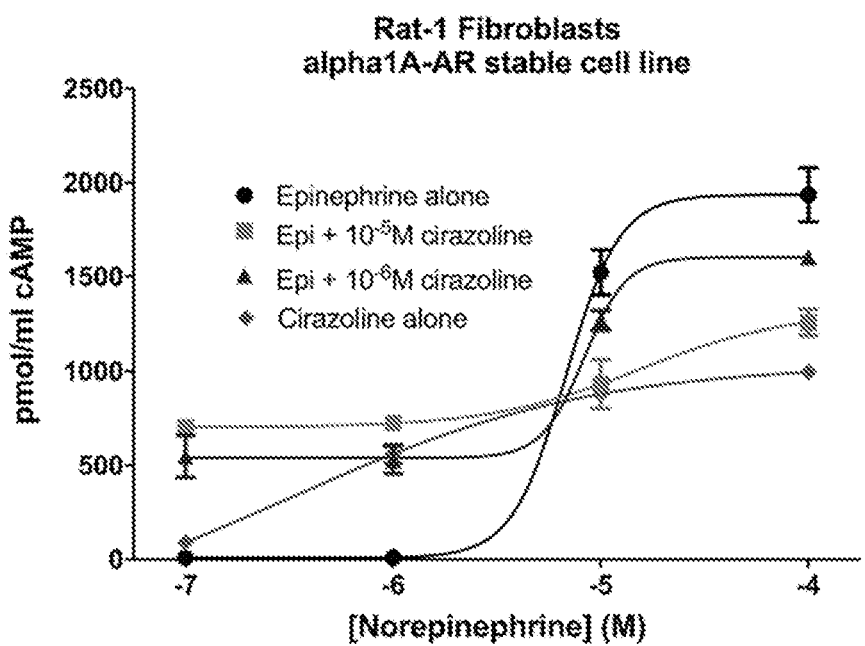

FIGURE 17
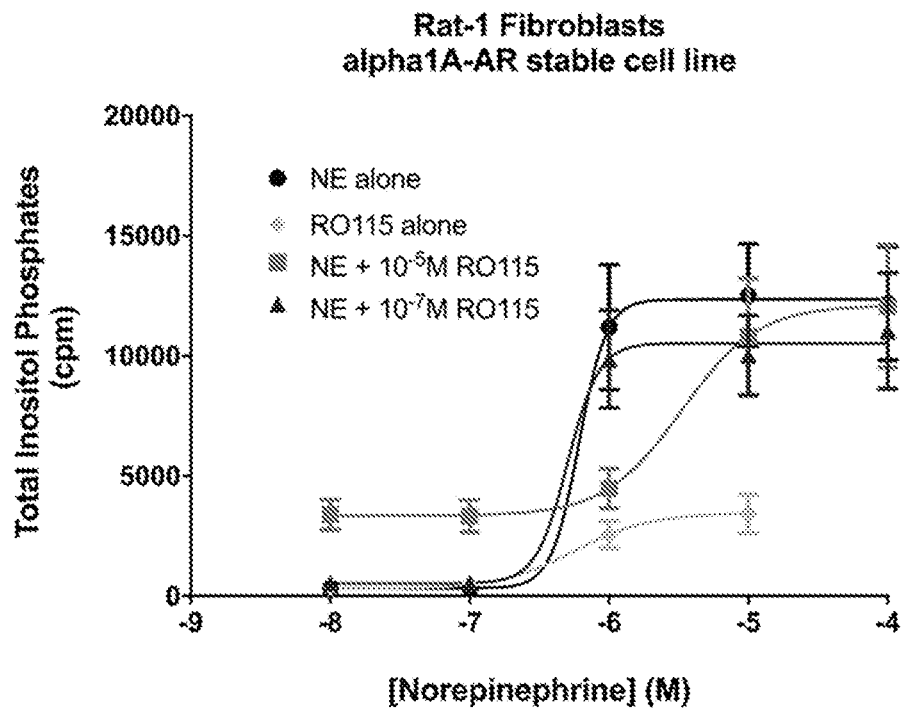
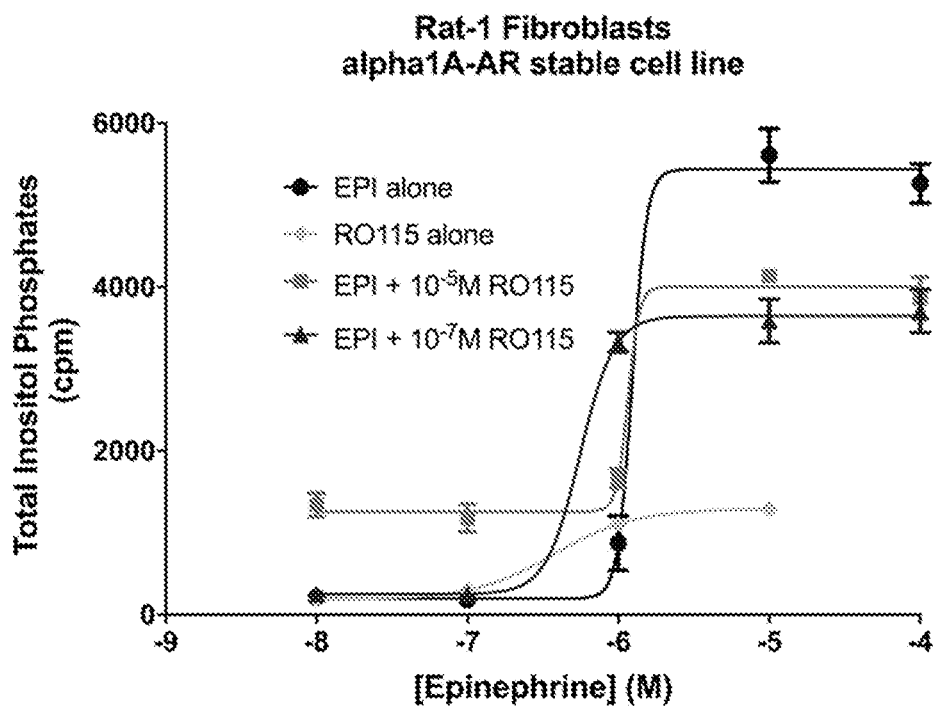

FIGURE 18
A.
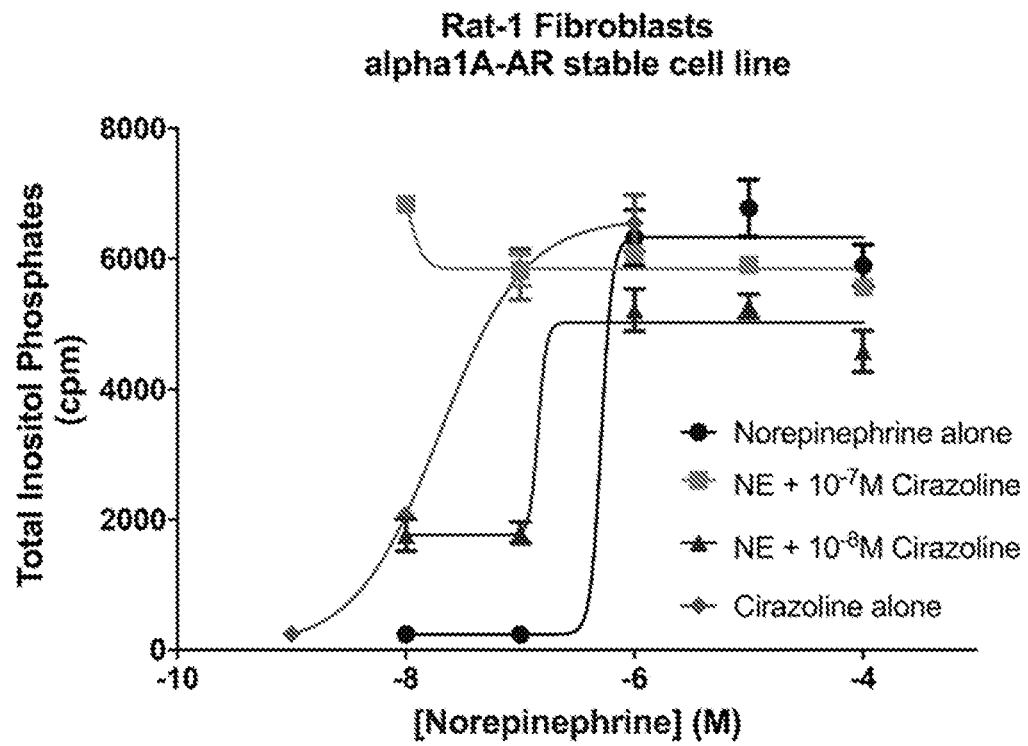
B.
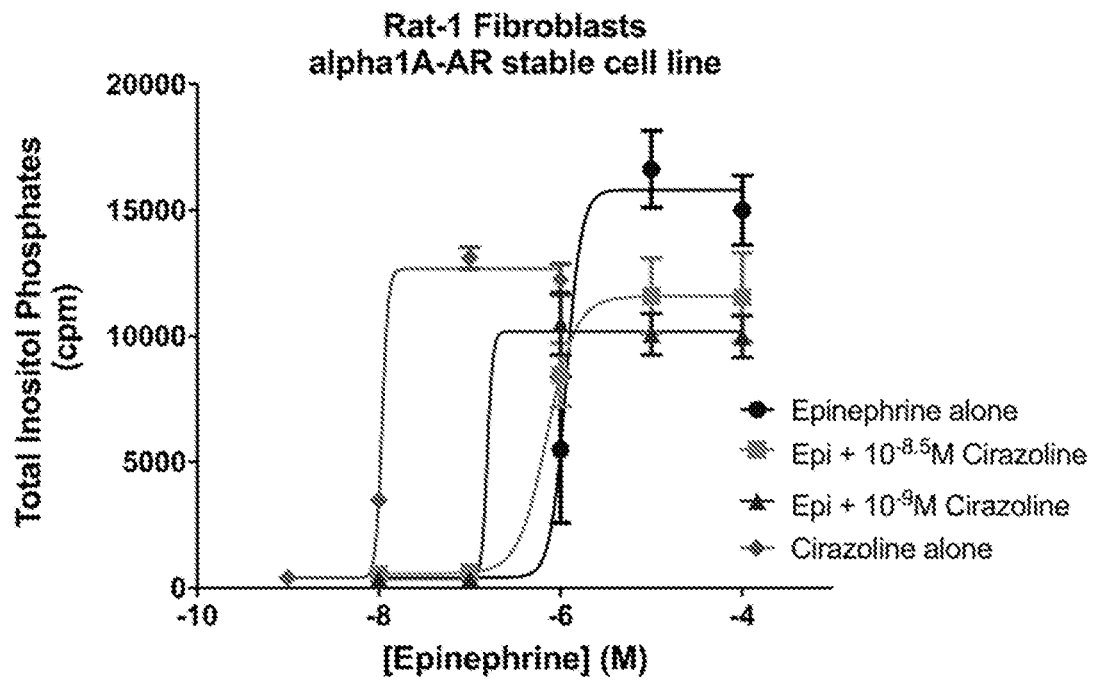

FIGURE 20
A.
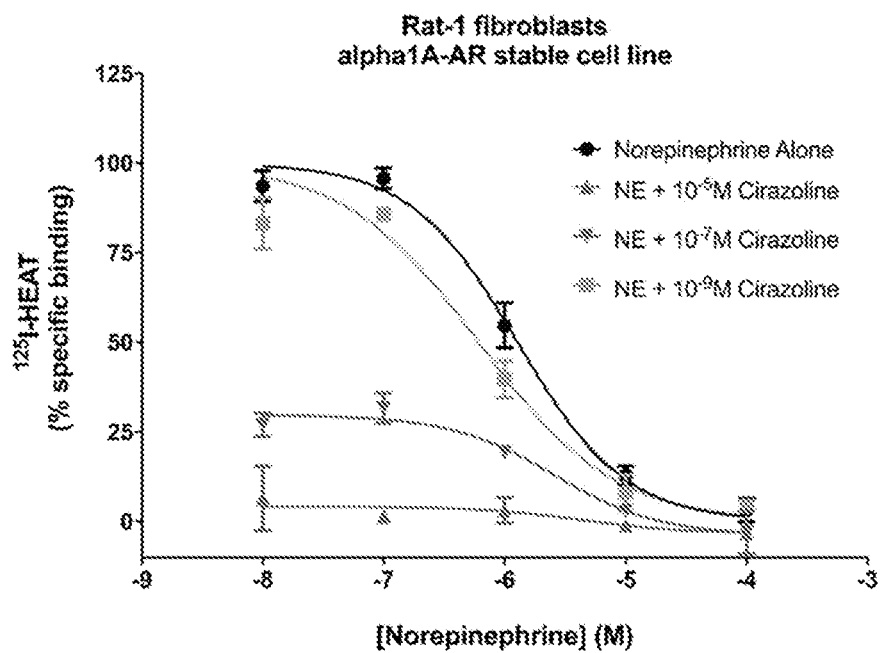
B.
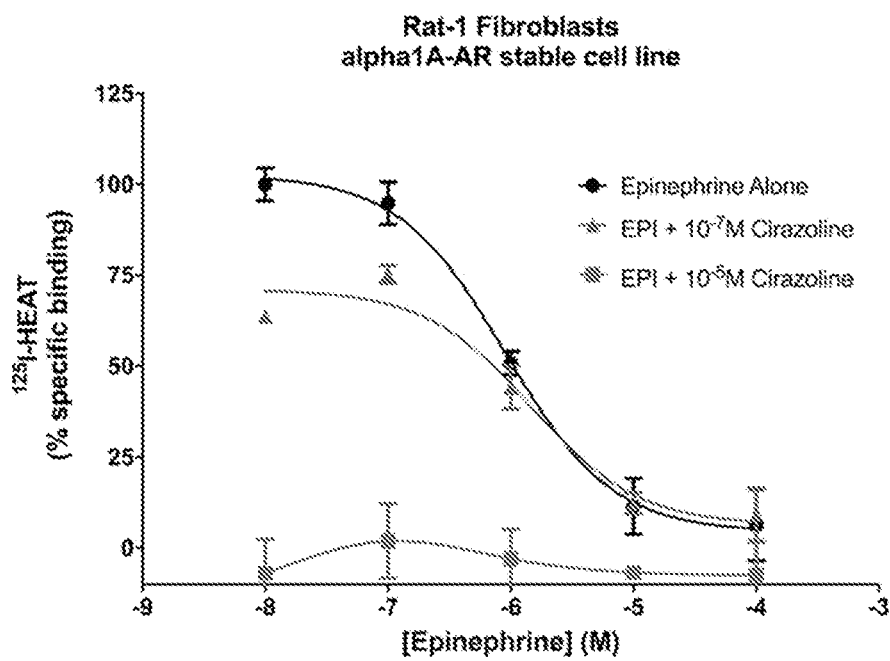

FIGURE 21
A.
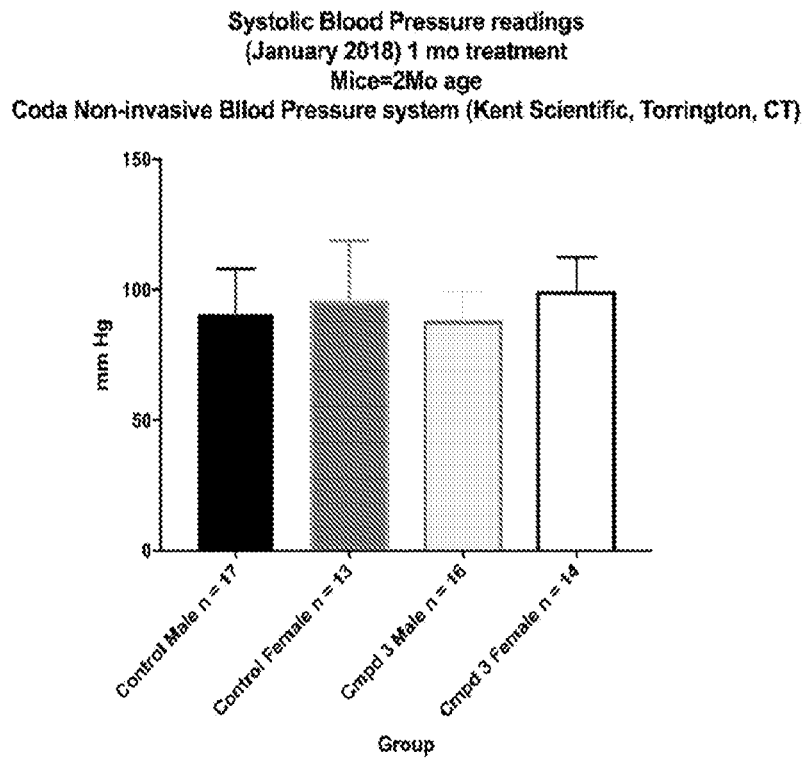
B.
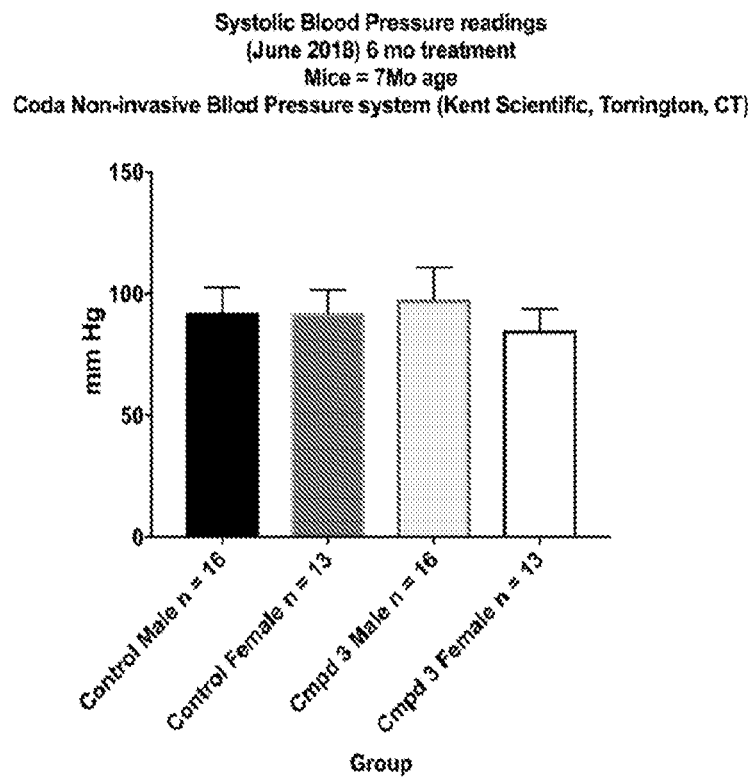

C.

FIGURE 22
A.
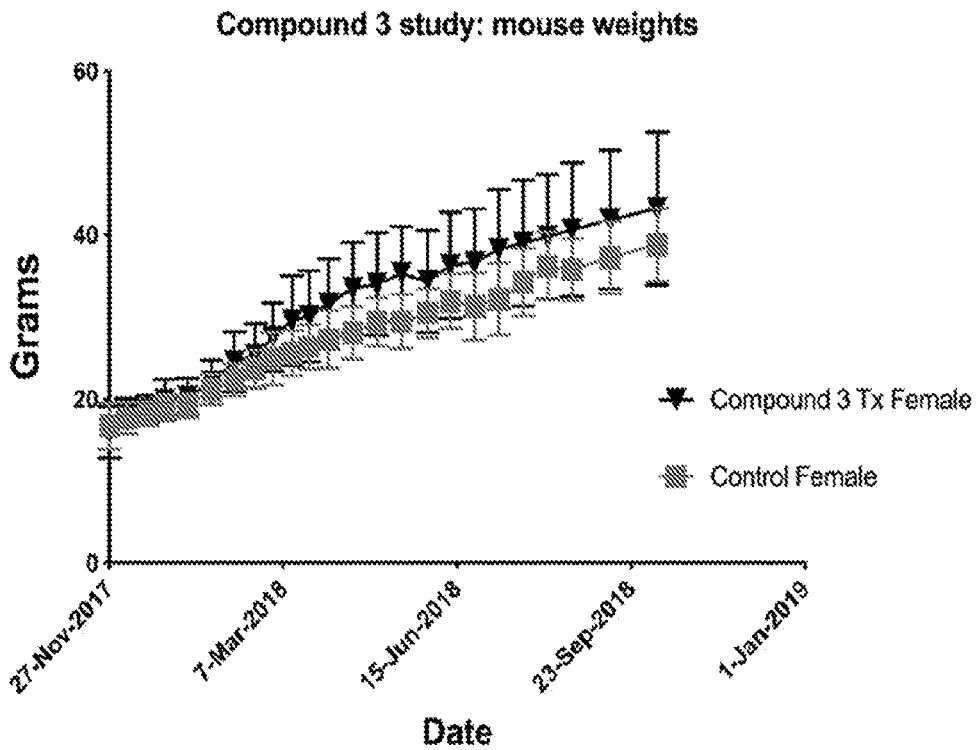
B.
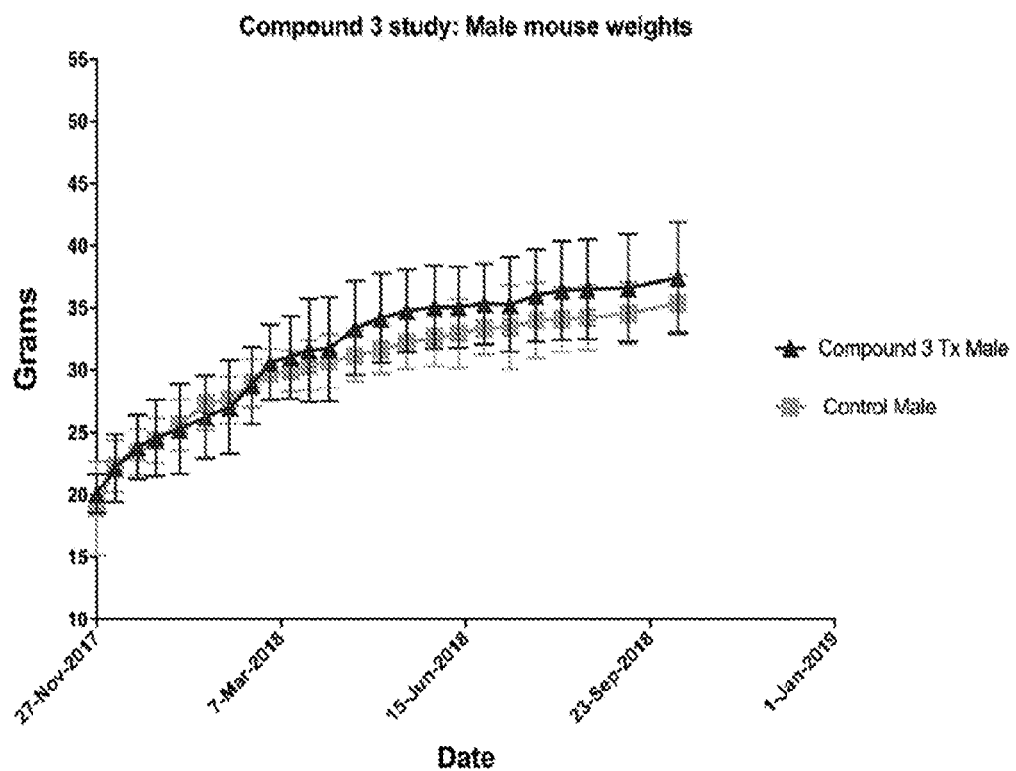

FIGURE 25
A.
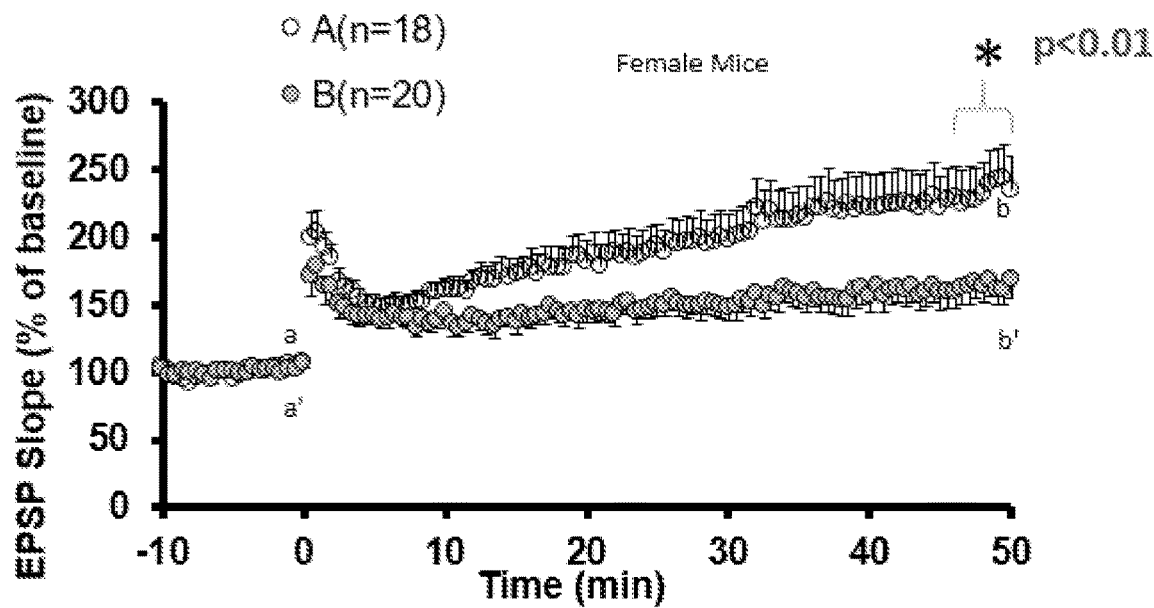
B.
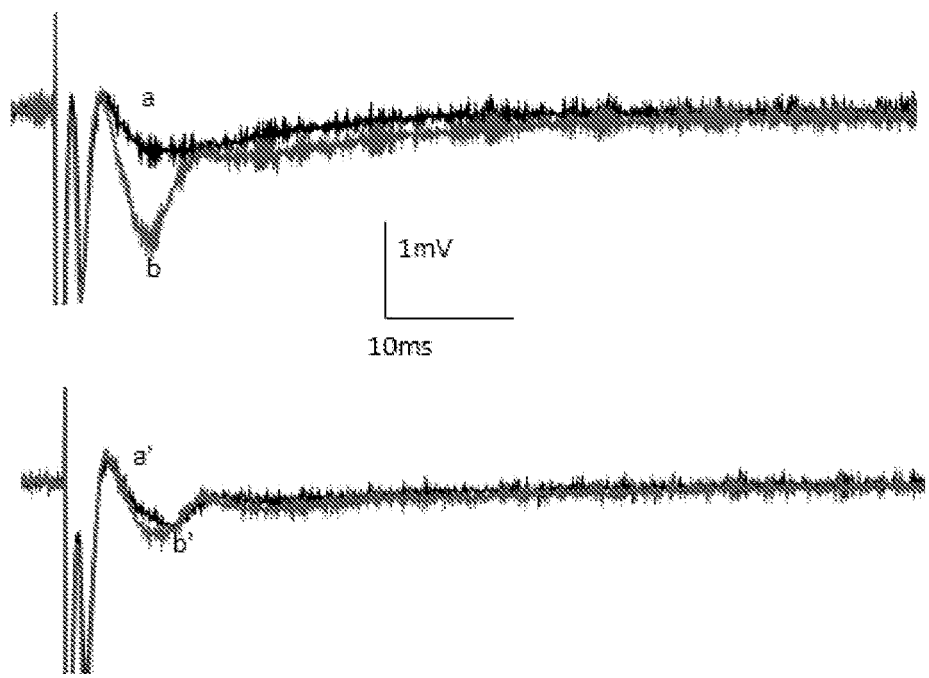

FIGURE 35

| Characteristic | Method | Result |
|---|---|---|
| Solubility | in hand | 11mg/ml |
| $T_{½}(h)$ plasma<br>$T_{½}(h)$ brain<br><br>T max (h) plasma<br>T max (h) brain | oral gavage<br>20mg/kg | 1.36<br>2.11<br><br>0.25<br>0.50 |
| Plasma $C_{max}$ | oral gavage | 754ng/ml |
| Brain $C_{max}$ | oral gavage | 47.86 ng/gram =<br>150nM |
| $AUC_{last}$ plasma<br>$AUC_{last}$ brain<br><br>$AUC_{inf}$ plasma<br>$AUC^{inf}$ brain | oral gavage | 860 h*ng/ml<br>217 h*ng/gram<br><br>870 h*ng/ml<br>236 h*ng/gram |
| Brain/Plasma ratio | | 0.27 |
| Plasma Binding<br>% free | rapid<br>equilibrium<br>dialysis<br>(mouse) | 86.20% |
| Intrinsic Clearance- | Mouse liver<br>microsomes | 30.8 (ul/min/mg) |
| Permeability Potential | Caco-2 cell<br>monolayer | $P_{app}$=46.14 (nm/s)<br>$P_{app}$ Efflux Ratio=7.68<br>ER+ amprenavir= 0.93 |

ALLOSTERIC ACTIVATORS OF THE ALPHA$_{1A}$-ADRENERGIC RECEPTOR

CROSS-REFERENCE TO RELATED APPLICATIONS

This application claims priority to U.S. Provisional Patent Application No. 62/837,565, filed on Apr. 23, 2019, the entire contents of which are fully incorporated herein by reference.

FIELD OF THE INVENTION

The present invention relates to compounds that are activators of the Alpha$_{1A}$-Adrenergic Receptor ($\alpha_{1A}$-AR) and methods of using such compounds for treating neurological conditions, for cardio-protection, and for treating other conditions. In certain embodiments, the $\alpha_{1A}$-AR activator compound has Formula (I) or Formula (Ia). In certain embodiments, the neurological condition is Alzheimer's disease, neurodegenerative disease, benign prostatic hyperplasia, memory loss, heart disease, depression, or Parkinson's disease.

BACKGROUND OF THE INVENTION

While Alzheimer's Disease (AD) is characterized by neuritic plaques and neurofibrillary tangles, composed mostly of β-amyloid (Aβ) and tau (1), clinical trials focused on amyloid immunotherapies have been disappointing and cognitive efficacy is questionable. Pathology starts in the entorhinal cortex and sequentially spreads to the hippocampus, the rest of the temporal lobe and eventually reaches all neocortical areas (2). Loss of neuronal synaptic density is another invariant feature of the disease that appears to precede neuronal loss (3) and this is where agents targeted to enhance neurogenesis and synaptic plasticity may benefit AD patients.

The cognitive decline observed in AD patients correlates better with synaptic pathology than either plaques or tangles. Thus, synaptic dysfunction is likely the most significant factor contributing to the initial stages of memory loss (4-7). AD mouse models correlate well to aspects of human disease as changes in long-term potentiation (LTP) have been observed in several AD mouse models (8-13). The cognitive impairments observed in AD patients are widely believed to be due to the progressive disruption of synaptic function and neurodegeneration (14-18). AD mice also have decreased neurogenesis in both subgranular zone (SGZ) and subventricular zone (SVZ) before Aβ pathology and treatments that increased hippocampal neurogenesis improved memory (18-19). Therefore, new therapeutics designed to improve cognitive, neurogenic, and synaptic functions are needed as an alternative method of treatment, particularly in light of the disappointing immunotherapies.

$\alpha_1$-adrenergic receptors (ARs) are G-Protein Coupled Receptors (GPCRs) that regulate neurotransmission through $\alpha_1$-AR subtypes ($\alpha_{1A}$, $\alpha_{1B}$, $\alpha_{1D}$) that are known to play roles in learning, memory, synaptic function and LTP. Previous studies assessing these roles in cognition have been inconsistent because of the use of non-selective ligands and many of these studies were published in the 1990s before the characterization of the cloned receptor subtypes and the subsequent development of animal models.

It is known, through transgenic animal models, that the different $\alpha_1$-AR subtypes can regulate different phenotypes in the brain. These studies were employed mouse models that systemically over express constitutively active $\alpha_1$-ARs that are chronically activated even when an agonist is not present. These mice provide the most selectivity in $\alpha_1$-AR subtype signaling currently available. Using these and KO mice, it was discovered that chronic stimulation of the $\alpha_{1B}$-AR subtype is apoptotic and neurodegenerative (20-23) while chronic stimulation of the $\alpha_{1A}$-AR subtype is neuroprotective, cardioprotective, neurogenic, and cognitive-enhancing (20, 24-28 all of which are herein incorporated by reference). As CAM $\alpha_{1A}$-AR mice have increased hippocampal synaptic plasticity and enhanced LTP, increased lifespan (24), hippocampal neurogenesis (26) and increased CA1 neuronal density, there is justification that agents that stimulate $\alpha_{1A}$-AR activity may be beneficial to AD. Normal mice treated with the mildly selective $\alpha_{1A}$-AR partial agonist cirazoline, increased both neurogenesis and cognition (24, 26) and $\alpha_{1A}$-AR KO mice had opposite effects. What is needed are compounds that are selectively increasing activation of $\alpha_{1A}$-AR but without known side effects such as increased blood pressure that are often associated with these types of drugs.

SUMMARY OF THE INVENTION

The present invention relates to compounds that may be activators of the Alpha$_{1A}$-Adrenergic Receptor ($\alpha_{1A}$-AR) and methods of using such compounds for treating neurological conditions, for cardio-protection, and for treating other conditions. In certain embodiments, the $\alpha_{1A}$-AR activator compound is a compound of formula (I) or formula (Ia) as described herein. In certain embodiments, the neurological condition is Alzheimer's disease, neurodegeneration, benign prostatic hyperplasia, memory loss, heart disease, depression, or Parkinson's disease.

Provided herein are compounds of formula (I):

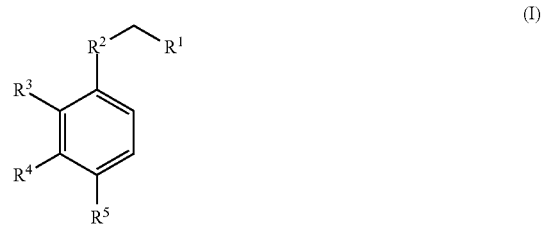

or a pharmaceutically acceptable salt thereof,
wherein:
$R^1$ is a 5- or 6-membered heteroaryl ring having 1, 2, or 3 nitrogen atoms, a 5- or 6-membered heterocyclyl ring having 1, 2, or 3 nitrogen atoms, or a guanidinyl group;
$R^2$ is —X—(CH$_2$)$_m$—, wherein X is selected from —O—, —NH—, —S—, and —CH$_2$—, and wherein m is 0, 1, or 2;
$R^3$ is selected from C$_2$-C$_6$ alkyl, C$_2$-C$_6$ alkenyl, C$_2$-C$_6$ alkynyl, C$_2$-C$_6$ hydroxyalkyl, C$_2$-C$_6$ haloalkyl, C$_2$-C$_6$ hydroxyhaloalkyl, C$_3$-C$_6$ cycloalkyl, aryl, halo, a hydrophobic amino acid moiety, and —(CHR$^a$)$_n$—R$^6$, wherein:
$R^a$ is selected from hydrogen and hydroxy;
n is 1 or 2; and
$R^6$ is selected from aryl, C$_3$-C$_6$ cycloalkyl, a 3- to 6-membered heterocyclic ring having 1, 2, or 3 heteroatoms selected from O, N, and S;
$R^4$ is selected from —NR$^b$—SO$_2$—R$^7$, —(CR$^c$R$^d$)—SO$_2$—R$^7$, and —(CR$^e$R$^f$)$_p$—R$^8$, wherein:
$R^b$ is selected from hydrogen, C$_1$-C$_3$ alkyl and C$_1$-C$_3$ haloalkyl;

$R^c$ and $R^d$ are each independently selected from hydrogen and methyl, or $R^c$ and $R^d$ are taken together with the carbon atom to which they are attached to form a $C_3$-$C_4$ cycloalkyl group;

$R^e$ and $R^f$ are each independently selected from hydrogen and halo;

p is 0 or 1;

$R^7$ is selected from hydrogen, $C_1$-$C_3$ alkyl, $C_1$-$C_3$ haloalkyl, and $C_3$-$C_6$ cycloalkyl; and $R^8$ is selected from $C_1$-$C_4$ alkoxy, $C_1$-$C_4$ haloalkoxy, hydroxy, —COOH, —CONH$_2$, and a 5-membered heteroaryl having 1, 2, or 3 nitrogen atoms; and $R^5$ is selected from hydrogen, halo, and any of the groups indicated for $R^3$ and $R^4$;

wherein each aryl, heteroaryl, cycloalkyl, and heterocyclyl can be independently unsubstituted or substituted with 1, 2, or 3 substituents independently selected from hydroxy, halo, $C_1$-$C_3$ alkyl, $C_1$-$C_3$ haloalkyl, and oxo.

In some embodiments, $R^1$ is selected from imidazolinyl, imidazolyl, triazolyl, pyrrolyl, pyrazolyl, imidazolidinyl, and tetrahydropyrimidinyl. In some embodiments, $R^1$ is selected from 4,5-dihydroimidazol-2-yl, imidazol-2-yl, pyrazol-1-yl, 1,2,3-triazol-2-yl, 1,2,3-triazol-1-yl, and 1,4,5,6-tetrahydropyrimidin-2-yl.

In some embodiments, $R^2$ is —X—(CH$_2$)$_m$—, wherein X is O and m is 0 (i.e. $R^2$ is O). In some embodiments, $R^2$ is —X—(CH$_2$)$_m$—, wherein X is O and m is 1 (i.e. $R^2$ is —O—CH$_2$—). In some embodiments, $R^2$ is —X—(CH$_2$)$_m$—, wherein X is —CH$_2$— and m is 0 (i.e. $R^2$ is —CH$_2$—).

In some embodiments, the compound has formula (Ia):

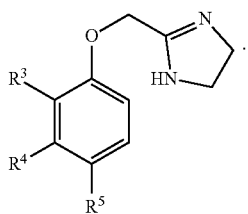

(Ia)

In some embodiments, $R^3$ is selected from $C_2$-$C_6$ alkyl, $C_2$-$C_6$ hydroxyalkyl, $C_2$-$C_6$ haloalkyl, $C_2$-$C_6$ hydroxyhaloalkyl, halo, and —(CHR$^a$)$_n$—R$^6$. In some embodiments, $R^3$ is isobutyl.

In some embodiments, $R^4$ is —NR$^b$—SO$_2$—R$^7$ or —(CR$^c$R$^d$)—SO$_2$—R$^7$. In some embodiments, $R^4$ is —NR$^b$—SO$_2$—R$^7$, $R^b$ is $C_1$-$C_3$ alkyl, and $R^7$ is hydrogen or $C_1$-$C_3$ alkyl. In some embodiments, $R^4$ is —N(CH$_3$)—SO$_2$—CH$_3$.

In some embodiments, $R^5$ is selected from hydrogen and halo. In some embodiments, $R^5$ is hydrogen.

In some embodiments, the compound is selected from:

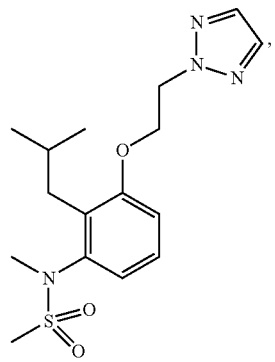

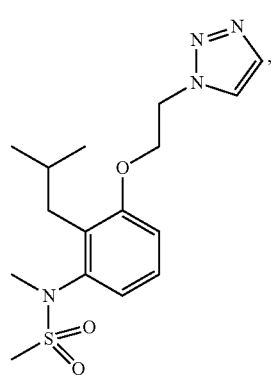

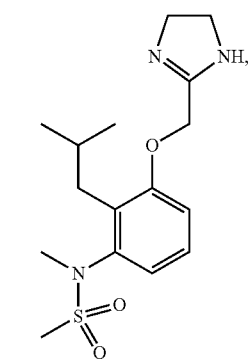

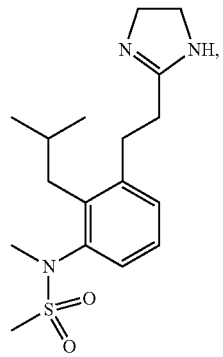

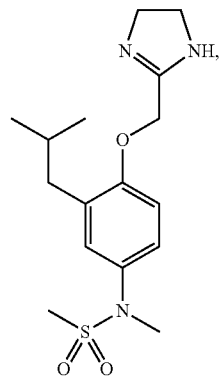

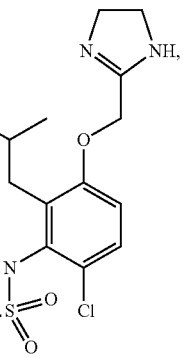

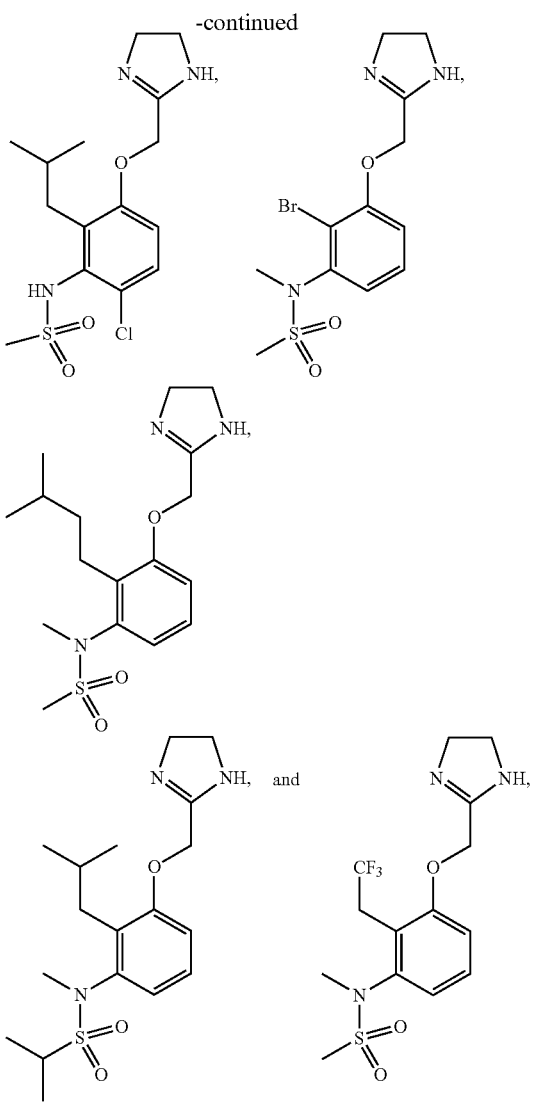

or a pharmaceutically acceptable salt thereof.

In some embodiments, the compound is not in a salt form. In some embodiments, the compound is in the form of a pharmaceutically acceptable salt. In some embodiments, compound is in the form of a hydrochloride salt.

In some embodiments, said compound is an alpha$_{1A}$-adrenergic receptor ($\alpha_{1A}$-AR) activator. In some embodiments, said compound is an $\alpha_{1A}$-AR activator of human $\alpha_{1A}$-AR.

In particular embodiments, the compound has at least one of the following properties in vivo: i) is a positive allosteric modulator (PAM) of the $\alpha_{1A}$-AR; ii) is brain-targeted; iii) is selective for and increases the affinity of the norepinephrine-bound receptor in the brain; iv) selectively increases the activation the $\alpha_{1A}$-AR subtype; v) has no measurable effect on the epinephrine-bound receptor in the periphery; vi) is not an agonist and does not increase any second messengers or calcium release on its own; vii) amplifies the norepinephrine-mediated cAMP response; viii) affects the cognitive centers with no side effects due to $\alpha_{1B}$- or $\alpha_{1D}$-AR activation; ix) has no, or a very small, measurable effect in the periphery to increase blood pressure; and/or x) crosses the blood brain barrier at therapeutic levels.

In certain embodiments, provided herein are methods comprising: treating a subject with a compound described above and herein (e.g., a compound of formula (I), such as a compound shown in FIG. 1). In some embodiments, the compounds described herein are used as a medicament to treat a disease or other condition described herein.

In particular embodiments, the subject (e.g., a human male or female) has at least one condition selected from the group consisting of: Alzheimer's disease, benign prostatic hyperplasia, memory loss, cognitive decline, depression, depressed mood, diabetes, seizures, neurodegeneration, Parkinson disease, autonomic failure, Multiple System Atrophy, amyotrophic lateral sclerosis (ALS), Huntington's disease, heart failure, cardiovascular disease, and Multiple Sclerosis. In further embodiments, the treating causes at least one of the following: improved memory, reduced depression, increased mood, increased metabolism, prolonged lifespan, arousal, satiety, recovery from heart failure, protection against stroke and/or heart attack, and reduced seizures.

In certain embodiments, the subject is selected from the group consisting of: i) a subject having Alzheimer's disease, ii) a subject with early-onset Alzheimer's disease, iii) a subject displaying one or more signs or symptoms or pathology indicative of Alzheimer's disease, iv) a subject suspected of having Alzheimer's disease, v) a subject suspected of displaying signs or symptoms or pathology indicative of Alzheimer's disease, vi) a subject at risk of Alzheimer's disease, vii) a subject at risk of displaying pathology indicative of Alzheimer's disease, viii) an animal model of Alzheimer's disease, and ix) a healthy subject wishing to reduce risk of Alzheimer's disease. In further embodiments, the treating the subject is under conditions such that one or more signs or symptoms of Alzheimer's disease is reduced or eliminated or that onset or progression of Alzheimer's disease is delayed or prevented. In further embodiments, the compound is co-administered with an antioxidant. In other embodiments, the compound is co-administered with an Alzheimer's therapeutic.

In some embodiments, the subject is selected from the group consisting of: i) a subject having a disease, ii) a subject displaying signs or symptoms or pathology indicative of the disease, iii) a subject suspected of having the disease, iv) a subject suspected of displaying signs or symptoms or pathology indicative of the disease, v) a subject at risk of the disease, vi) a subject at risk of displaying pathology indicative of the disease, vii) an animal model of the disease, and viii) a healthy subject wishing to reduce risk of the disease. In certain embodiments, the disease is selected from the group consisting of: diabetes, Parkinson disease, autonomic failure, benign prostatic hyperplasia, Multiple System Atrophy, amyotrophic lateral sclerosis (ALS), Huntington's disease, heart failure, cardiovascular disease, neurodegeneration, and Multiple Sclerosis.

In certain embodiments, the treating comprises administering between 0.05 mg-250 mg of the compound to the subject (e.g., 0.05 . . . 0.1 . . . 1 . . . 10 . . . 25 . . . 75 . . . 125 . . . 175 . . . or 250 mg). In other embodiments, the treating comprises administering between 0.5 mg-150 mg of the compound to the subject. In other embodiments, the treating comprises administering between 2.5 mg-80 mg of the compound to the subject.

In further embodiments, the treating comprises administering 0.005 mg per kg-5 mg per kg to the subject per day for at least two days (e.g., 0.005 . . . 0.01 . . . 0.05 . . . 0.10 . . . 0.5 . . . 1 . . . 2.5 . . . 5.0 mg per kg of subject per day). In certain embodiments, the treating comprises administering 0.01 mg per kg-1 mg per kg to the subject per day for at least two days. In other embodiments, the treating comprises administering 0.1 mg per kg-0.5 mg per kg to the subject per day for at least two days. In particular embodiments, the at least two days is at least 10 days . . . at least 50 days . . . at least 100 days . . . or at least 300 days.

In certain embodiments, the compound is co-administered with an Alzheimer's therapeutic selected from the group consisting of alkylated diphenylamines, N-alkylated phenylenediamines, phenyl-α-naphthylamine, alkylated phenyl-α-naphthylamine, dimethyl quinolines, trimethyldihydroquinolines, hindered phenolics, alkylated hydroquinones, hydroxylated thiodiphenyl ethers, alkylidenebisphenols, thiopropionates, metallic dithiocarbamates, 1,3,4-dimercaptothiadiazole, an oil soluble copper compound, NAUGALUBE 438, NAUGALUBE 438L, NAUGALUBE 640, NAUGALUBE 635, NAUGALUBE 680, NAUGALUBE AMS, NAUGALUBE APAN, Naugard PANA, NAUGALUBE TMQ, NAUGALUBE 531, NAUGALUBE 431, NAUGALUBE BHT, NAUGALUBE 403, NAUGALUBE 420, ascorbic acid, tocopherols, alpha-tocopherol, a sulfhydryl compound, sodium metabisulfite, N-acetyl-cysteine, lipoic acid, dihydrolipoic acid, resveratrol, lactoferrin, ascorbic acid, ascorbyl palmitate, ascorbyl polypeptide, butylated hydroxytoluene, retinoids, retinol, retinyl palmitate, tocotrienols, ubiquinone, a flavonoid, an isoflavonoid, genistein, diadzein, resveratrol, grape seed, green tea, pine bark, propolis, IRGANOX, Antigene P, SUMILIZER GA-80, beta-carotene, lycopene, vitamin C, vitamin E, and vitamin A.

In other embodiments, the compound is co-administered with a diabetes therapeutic. Multiple diabetes therapeutics find use with the compositions and methods of the present invention including, but not limited to, Vanadium, metformin, thiazolidinedione, TZD, intermediate-acting insulin, neutral protamine Hagedorn, NPH, a long-acting insulin, glargine, Lantus, insulin, insulin detemir, Levemir, Incretin mimetic, Exenatide, Byetta, Sulfonylurea agent, chlorpropamide, tolbutamide, tolazamide, acetohexamide, glyburide, glipizide, glimepiride, Meglitinides, Repaglinide, Prandin, Biguanides, Metformin, Glucophage, Alpha-glucosidase inhibitor, AGI, Acarbose, Precose, Miglitol, Glyset, thiazolidinedione, Pioglitazone, Actos, Rosiglitazone, Avandia, Amylin analog, Pramlintide acetate, and Symlin.

In some embodiments, the compound is co-administered with an ALS therapeutic. ALS therapeutics include, but are not limited to, Riluzole, Baclofen (Lioresal) and Tizanidine (Zanaflex). In other embodiments, the compound is co-administered with a Parkinson's disease (PD) therapeutic, such as dopamine prodrugs such as levadopa/PDI and levodopa/carbidopa (e.g., Sinemet, Sinemet CR), dopamine agonists such as apomorphine (e.g., Apokyn), bromocriptine (e.g., Parlodel), pergolide (e.g., Permax), pramipexole (e.g., Mirapex), and ropinirole (e.g., Requip), catechol-O-methyl-transferase (COMT) inhibitors such as tolcapone (e.g., Tasmar), and entacapone (e.g., Comtan), anticholinergics such as trihexyphenidyl (e.g., Artane, Trihexy), and benztropine mesylate (e.g., Cogentin), MAO-B inhibitors such as selegiline (e.g., Eldepryl), and amantadine (e.g., Symmetrel).

In further embodiments, the compound is co-administered with an MS therapeutic. Such agents include, but are not limited to: immunomodulators (e.g., Interferon beta-1a (Avonex), Interferon beta-1a (Rebif), Interferon beta-1b (Betaseron), Glatiramer acetate (Copaxone), and Natalizumab (Tysabri)), corticosteroids (e.g., methylprednisolone), and immunosuppressors (e.g., Mitoxantrone (Novantrone), Cyclophosphamide (Cytoxan, Neosar), Azathioprine (IMURAN), Methotrexate (Rheumatrex).

DESCRIPTION OF THE DRAWINGS

FIGS. 3A-B show: (A) binding isotherms showing an affinity of allosteric Compound 3 for the $\alpha_{1A}$-AR at 0.1 uM, with the orthosteric ligand phentolamine shown for comparison, N=4-5; (b) binding isotherm for Compound 3 in the absence of GTP in the binding buffer, indicating the presence of a high affinity site of 0.001 nM and a low affinity site of 100 nM.

FIGS. 4A-B shows binding isotherms showing no affinity of allosteric Compound 3 for the alpha$_{1D}$-AR (A) or alpha$_{1D}$-AR (B) subtypes. N=4-5.

FIGS. 5A-B show: (A) binding curve of NE competing off the radiolabel antagonist $^{125}$I-HEAT alone or in the presence of a $10^{-5}$M dose, $10^{-7}$M dose, or $10^{-9}$M dose of Compound 3 in alpha$_{1A}$-AR expressing cells, N=5-6; (B) competition binding curve of epinephrine at the alpha$_{1A}$-AR competing off the radiolabel antagonist $^{125}$I-HEAT with or without a $10^{-5}$M dose of Compound 3, N=4.

FIGS. 6A-B show: (A) competition binding curve of norepinephrine competing off the radiolabel antagonist $^{125}$I-HEAT at the alpha$_{1B}$-AR or alpha$_{1D}$-AR; (B) Compound 3 at $10^{-5}$M dose does not increase the affinity of norepinephrine at either AR subtype.

FIGS. 8A-D show: (A) Compound 3 at ($10^{-5}$M-$10^{-9}$M) potentiates the norepinephrine alone-mediated cAMP response at the alpha$_{1A}$-AR, maximizing at $10^{-8}$M, N=4-6; (B) Compound 3 has no effect on the NE-mediated inositol phosphate response at the alpha$_{1A}$-AR at $10^{-5}$M or $10^{-7}$M dose, N=3; (C) Compound 3 also has no effect on the Epi-mediated cAMP response (red) at the alpha$_{1A}$-AR at $10^{-5}$M through $10^{-7}$M dose, N=3; (D) Compound 3 also has no effect on the Epi-mediated inositol phosphate response at the alpha$_{1A}$-AR at $10^{-5}$M or $10^{-7}$M dose, N=3.

FIGS. 9A-B show that Compound 3 has no effect on the NE-mediated cAMP response at the alpha$_{1B}$-AR (A) or alpha$_{1D}$-AR (B) subtypes.

FIGS. 15A-B show the cAMP signaling response to either norepinephrine (A) or epinephrine (B) to increasing doses of RO115-1240 from $10^{-7}$M to $10^{-5}$M at the alpha$_{1A}$-AR subtype. High doses shift the curve to the right to lower potency (inhibition).

FIGS. 16A-B show the cAMP signaling response to either norepinephrine (A) or epinephrine (B) to increasing doses of cirazoline from $10^{-7}$M to $10^{-5}$M at the alpha$_{1A}$-AR subtype.

FIG. 17A-B show the ability of RO115-1240 alone, norepinephrine (A) or epinephrine alone (B) or with increasing doses of RO115-1240 ($10^{-5}$M to $10^{-7}$M) to stimulate inositol phosphate production at the alpha$_{1A}$-AR.

FIGS. 18A-B show the ability of cirazoline alone, norepinephrine (A) or epinephrine alone (B) or with increasing doses of cirazoline ($10^{-7}$M to $10^{-9}$M) to stimulate inositol phosphate production at the alpha$_{1A}$-AR. Cirazoline is such a strong agonist at the IP response that low amounts can only be added to NE or EPI in order to see competitive inhibition. Note in (A), the green line representing the highest dose used ($10^{-7}$M) will give a flat line because that dose is already at maximum effect.

FIGS. 20A-B show competition binding curves of norepinephrine (A) or epinephrine (B) competing off the radiolabel antagonist $^{125}$I-HEAT at the alpha$_{1A}$-AR subtype. Increasing doses of cirazoline (from $10^{-5}$ to $10^{-9}$M) totally inhibit the binding of either norepinephrine or epinephrine equally, showing noncompetitive behavior.

FIGS. 22A-B show Compound 3-treated 3×TG female mice have increased body weight compared to untreated mice.

FIGS. 25A-B show: (A) LTP in Compound 3-treated AD female mice (A) and untreated control AD female mice (B); (B)superimposed representative fEPSPs were recorded 15 min before and 50 min after LTP induction. These studies were performed in the CA1 (stratum radiatum) hippocampus.

FIG. 35 shows pharmacokinetic data for Compound 3.

DEFINITIONS

Figure 1:
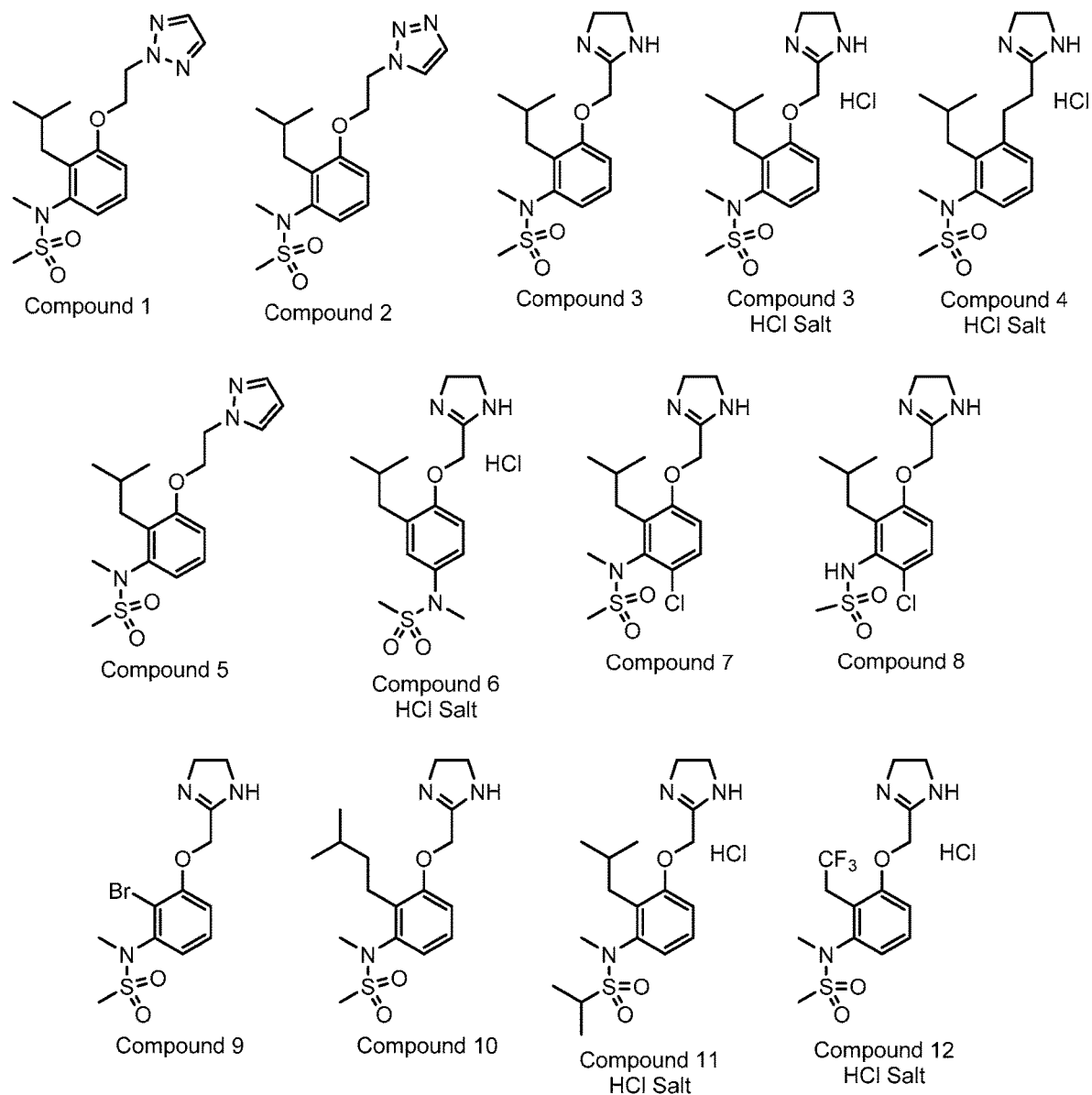
FIG. 1 shows structures of exemplary compounds of Formula (I).

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. The materials, methods, and examples disclosed herein are illustrative only and not intended to be limiting.

As used herein, the terms "host," "subject" and "patient" refer to any animal, including but not limited to, human and non-human animals (e.g., dogs, cats, cows, horses, sheep, poultry, fish, crustaceans, etc.) that is studied, analyzed, tested, diagnosed or treated. As used herein, the terms "host," "subject" and "patient" are used interchangeably, unless indicated otherwise.

As used herein, the terms "Alzheimer's disease" and "AD" refer to a neurodegenerative disorder and encompasses familial Alzheimer's disease and sporadic Alzheimer's disease. The term "familial Alzheimer's disease" refers to Alzheimer's disease associated with genetic factors (i.e., demonstrates inheritance) while "sporadic Alzheimer's disease" refers to Alzheimer's disease that is not associated with prior family history of the disease. Symptoms indicative of Alzheimer's disease in human subjects typically include, but are not limited to, mild to severe dementia, progressive impairment of memory (ranging from mild forgetfulness to disorientation and severe memory loss), poor visuo-spatial skills, personality changes, poor impulse control, poor judgement, distrust of others, increased stubbornness, restlessness, poor planning ability, poor decision making, and social withdrawal. In severe cases, patients lose the ability to use language and communicate, and require assistance in personal hygiene, eating and dressing, and are eventually bedridden. Hallmark pathologies within brain tissue include extracellular neuritic β-amyloid plaques, neurofibrillary tangles, neurofibrillary degeneration, granulovascular neuronal degeneration, synaptic loss, and extensive neuronal cell death.

As used herein, the term "early-onset Alzheimer's disease" refers to the classification used in Alzheimer's disease cases diagnosed as occurring before the age of 65. As used herein, the term "late-onset Alzheimer's disease" refers to the classification used in Alzheimer's disease cases diagnosed as occurring at or after the age of 65.

As used herein, the terms "subject having Alzheimer's disease" or "subject displaying signs or symptoms or pathology indicative of Alzheimer's disease" or "subjects suspected of displaying signs or symptoms or pathology indicative of Alzheimer's disease" refer to a subject that is identified as having or likely to have Alzheimer's disease based on known Alzheimer's signs, symptoms and pathology.

As used herein, the terms "subject at risk of displaying pathology indicative of Alzheimer's disease" and "subject at risk of Alzheimer's disease" refer to a subject identified as being at risk for developing Alzheimer's disease (e.g., due to age or familial inheritance pattern of Alzheimer's disease in the subject's family).

As used herein, the term "Alzheimer's therapeutic" refers to an agent used to treat or prevent Alzheimer's disease. Such agents include, but are not limited to, small molecules, drugs, antibodies, pharmaceuticals, and the like. For example, therapeutics used to treat Alzheimer's disease include, but are not limited to, NMDA antagonists (e.g., memantine), and AChE inhibitors (e.g., tacrine (Cognex), donepezil (Aricept), rivastigmine (Exelon), and galantamine (galanthamine, Reminyl)).

As used herein, the terms "subject having amyotrophic lateral sclerosis (ALS)" or "subject displaying signs or symptoms or pathology indicative of ALS" or "subjects suspected of displaying signs or symptoms or pathology indicative of ALS" refer to a subject that is identified as having or likely to have ALS based on known ALS signs, symptoms and pathology.

As used herein, the terms "subject at risk of displaying pathology indicative of ALS" and "subject at risk of ALS" refer to a subject identified as being at risk for developing ALS (e.g., due to age or familial inheritance pattern of ALS in the subject's family).

As used herein, the term "ALS therapeutic" refers to an agent used to treat or prevent ALS. Such agents include, but are not limited to, small molecules, drugs, antibodies, pharmaceuticals, and the like. For example, therapeutics used to treat ALS include, but are not limited to, Riluzole, Baclofen (Lioresal) and Tizanidine (Zanaflex).

As used herein, the terms "Huntington's Disease" and "HD" refer to a neurodegenerative disorder that is an adult-onset, autosomal dominant inherited disorder associated with cell loss within a specific subset of neurons in the basal ganglia and cortex. Characteristic features of HD include involuntary movements (e.g., chorea, a state of excessive, spontaneous movements, irregularly timed, randomly distributed, and abrupt, is a characteristic feature of HD), dementia, and behavioral changes. Neuropathology in HD occurs within the neostriatum, in which gross atrophy of the caudate nucleus and putamen is accompanied by selective neuronal loss and astrogliosis. Marked neuronal loss also is seen in deep layers of the cerebral cortex. Other regions, including the globus pallidus, thalamus, subthalamic nucleus, substantia nigra, and cerebellum, show varying degrees of atrophy depending on the pathologic grade.

As used herein, the terms "subject having HD" or "subject displaying signs or symptoms or pathology indicative of HD" or "subjects suspected of displaying signs or symptoms or pathology indicative of HD" refer to a subject that is identified as having or likely to have HD based on known HD signs, symptoms and pathology.

As used herein, the terms "subject at risk of displaying pathology indicative of HD" and "subject at risk of HD" refer to a subject identified as being at risk for developing HD (e.g., due to age or familial inheritance pattern of HD in the subject's family).

As used herein, the term "HD therapeutic" refers to an agent used to treat or prevent HD. Such agents include, but are not limited to, small molecules, drugs, antibodies, pharmaceuticals, and the like. For example, therapeutics used to treat HD include, but are not limited to, anticonvulsant medications including, but not limited to valproic acid (e.g., Depakote, Depakene, and Depacon) and benzodiazepines such as clonazepam (e.g., Klonopin), Antipsychotic medications (e.g., risperidone (e.g., Risperdal), and haloperidol (e.g., Haldol)), Rauwolfia alkoids (e.g., resperine), and antidepressants (e.g., paroxetine (e.g., Paxil)).

As used herein, the terms "Parkinson's disease" and "PD" refer to a neurodegenerative disorder that is a progressive neurodegenerative disorder associated with a loss of dopaminergic nigrostriatal neurons. Characteristic features of PD include loss of pigmented dopaminergic neurons in the substantia nigra and the presence of Lewy bodies.

As used herein, the terms "subject having PD" or "subject displaying signs or symptoms or pathology indicative of PD" or "subjects suspected of displaying signs or symptoms or pathology indicative of PD" refer to a subject that is identified as having or likely to have PD based on known PD signs, symptoms and pathology.

As used herein, the terms "subject at risk of displaying pathology indicative of PD" refer and "subject at risk of PD" refer to a subject identified as being at risk for developing PD (e.g., due to age or familial inheritance pattern of PD in the subject's family).

As used herein, the term "PD therapeutic" refers to an agent used to treat or prevent PD. Such agents include, but are not limited to, small molecules, drugs, antibodies, pharmaceuticals, and the like. For example, therapeutics used to treat PD include, but are not limited to, dopamine prodrugs such as levadopa/PDI and levodopa/carbidopa (e.g., Sinemet, Sinemet CR), dopamine agonists such as apomorphine (e.g., Apokyn), bromocriptine (e.g., Parlodel), pergolide (e.g., Permax), pramipexole (e.g., Mirapex), and ropinirole (e.g., Requip), catechol-O-methyltransferase (COMT) inhibitors such as tolcapone (e.g., Tasmar), and entacapone (e.g., Comtan), anticholinergics such as trihexyphenidyl (e.g., Artane, Trihexy), and benztropine mesylate (e.g., Cogentin), MAO-B inhibitors such as selegiline (e.g., Eldepryl), and amantadine (e.g., Symmetrel).

As used herein, the terms "Multiple sclerosis" and "MS" refer to a neurodegenerative disorder that is an inflammatory, demyelinating disease of the central nervous system (CNS). MS lesions, characterized by perivascular infiltration of monocytes and lymphocytes, appear as indurated areas in pathologic specimens; hence, the term "sclerosis in plaques." Characteristic features of MS include perivenular infiltration of lymphocytes and macrophages in the parenchyma of the brain, brain stem, optic nerves, and spinal cord, almost constant lesion formation and a progressive clinical course leading to physical disability.

As used herein, the terms "subject having MS" or "subject displaying signs or symptoms or pathology indicative of MS" or "subjects suspected of displaying signs or symptoms or pathology indicative of MS" refer to a subject that is identified as having or likely to have MS based on known MS signs, symptoms and pathology.

As used herein, the terms "subject at risk of displaying pathology indicative of MS" and "subject at risk of MS" refer to a subject identified as being at risk for developing MS.

As used herein, the term "MS therapeutic" refers to an agent used to treat or prevent MS. Such agents include, but are not limited to, small molecules, drugs, antibodies, pharmaceuticals, and the like. For example, therapeutics used to treat MS include, but are not limited to, immunomodulators (e.g., Interferon beta-1a (Avonex), Interferon beta-1a (Rebif), Interferon beta-1b (Betaseron), Glatiramer acetate (Copaxone), and Natalizumab (Tysabri)), corticosteroids (e.g., methylprednisolone), and immunosuppressors (e.g., Mitoxantrone (Novantrone), Cyclophosphamide (Cytoxan, Neosar), Azathioprine (IMURAN), Methotrexate (Rheumatrex).

As used herein, the term "diabetes" refers to an autoimmune disease characterized by necrosis of pancreatic islet cells and a lack of insulin secretion. For example, patients with type 1 diabetes are dependent on insulin. Characteristics traits of diabetes include peripheral insulin resistance with an insulin-secretory defect that varies in severity, and complications that include hypoglycemia and hyperglycemia, increased risk of infections, microvascular complications (e.g., retinopathy, nephropathy), neuropathic complications, and macrovascular disease.

As used herein, the terms "subject having diabetes" or "subject displaying signs or symptoms or pathology indicative of diabetes" or "subjects suspected of displaying signs or symptoms or pathology indicative of diabetes" refer to a subject that is identified as having or likely to have diabetes based on known diabetes signs, symptoms and pathology.

As used herein, the term "subject at risk of displaying pathology indicative of diabetes" and "subject at risk of diabetes" refer to a subject identified as being at risk for developing diabetes (e.g., due to age, weight, race, or familial inheritance pattern of diabetes in the subject's family).

As used herein, the term "diabetes therapeutic" refers to an agent used to treat or prevent diabetes. Such agents include, but are not limited to, small molecules, drugs, antibodies, pharmaceuticals, and the like. For example, therapeutics used to treat diabetes include, but are not limited to, oral medication to increase insulin sensitivity (e.g., metformin, a thiazolidinedione (TZD)), intermediate-acting insulin (e.g., neutral protamine Hagedorn (NPH)), a long-acting insulin (e.g., glargine (Lantus) insulin, insulin detemir (Levemir)), Incretin mimetics (e.g., Exenatide (Byetta)), Sulfonylurea agents (e.g., chlorpropamide, tolbutamide, tolazamide, acetohexamide, glyburide, glipizide, and glimepiride), Meglitinides (e.g., Repaglinide (Prandin)), Biguanides (e.g., Metformin (Glucophage)), Alpha-glucosidase inhibitors (AGIs) (e.g., Acarbose (Precose), Miglitol (Glyset)), thiazolidinediones (e.g., Pioglitazone (Actos), Rosiglitazone (Avandia)), and Amylin analogs (e.g., Pramlintide acetate (Symlin)).

As used herein, the term "cognitive function" generally refers to the ability to think, reason, concentrate, or remember. Accordingly, the term "decline in cognitive function" refers to the deterioration of lack of ability to think, reason, concentrate, or remember.

As used herein, the term "effective amount" refers to the amount of a composition (e.g., comprising a compound of Formula I or II (e.g., Compounds 1-6) sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., composition comprising a compound of Formula I or II, and one or more other agents—e.g., an Alzheimer's disease therapeutic, or, a second form of a compound of Formula I or II to a subject). In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "treatment" or grammatical equivalents encompasses the improvement and/or reversal of the symptoms of disease (e.g., neurodegenerative disease). A compound which causes an improvement in any parameter associated with disease when used in the screening methods of the instant invention may thereby be identified as a therapeutic compound. The term "treatment" refers to both therapeutic treatment and prophylactic or preventative measures. For example, those who may benefit from treatment with compositions and methods of the present invention include those already with a disease and/or disorder (e.g., neurodegenerative disease, diabetes or lack of or loss of cognitive function) as well as those in which a disease and/or disorder is to be prevented (e.g., using a prophylactic treatment of the present invention).

As used herein, the term "at risk for disease" refers to a subject (e.g., a human) that is predisposed to experiencing a particular disease. This predisposition may be genetic (e.g., a particular genetic tendency to experience the disease, such as heritable disorders), or due to other factors (e.g., age, weight, environmental conditions, exposures to detrimental compounds present in the environment, etc.). Thus, it is not intended that the present invention be limited to any particular risk, nor is it intended that the present invention be limited to any particular disease.

As used herein, the term "suffering from disease" refers to a subject (e.g., a human) that is experiencing a particular disease. It is not intended that the present invention be limited to any particular signs or symptoms, nor disease. Thus, it is intended that the present invention encompass subjects that are experiencing any range of disease (e.g., from sub-clinical manifestation to full-blown disease) wherein the subject exhibits at least some of the indicia (e.g., signs and symptoms) associated with the particular disease.

As used herein, the term "kit" is used in reference to a combination of reagents and other materials. It is contemplated that the kit may include reagents such as nutrients and drugs as well as administration means. It is not intended that the term "kit" be limited to a particular combination of reagents and/or other materials.

As used herein, the term "pharmaceutical composition" refers to the combination of an active agent (e.g., composition comprising a compound of Formula I or II) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., alveolar, buccal, lingual, masticatory, or nasal mucosa, and other tissues and cells that line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintegrants (e.g., potato starch or sodium starch glycolate), and the like. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts. Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like. Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, "benign prostatic hyperplasia (BPH)," which is also called prostate enlargement, is a noncancerous increase in size of the prostate. Symptoms may include frequent urination, trouble starting to urinate, weak stream, inability to urinate, or loss of bladder control. Complications can include urinary tract infections, bladder stones, and chronic kidney problems. Risk factors for BPH include a family history, obesity, type 2 diabetes, not enough exercise, and erectile dysfunction. The underlying mechanism involves the prostate pressing on the urethra. Diagnosis is typically based on symptoms and examination after ruling out other possible causes As used herein, the terms "subject having BPH" or "subject displaying signs or symptoms or pathology indicative of BPH" or "subjects suspected of displaying signs or symptoms or pathology indicative of BPH" refer to a subject that is identified as having or likely to have BPH based on known BPH signs, symptoms and pathology.

As used herein, the terms "subject at risk of displaying pathology indicative of BPH" and "subject at risk of BPH" refer to a subject identified as being at risk for developing BPH.

Definitions of specific functional groups and chemical terms are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Sorrell, Organic Chemistry, $2^{nd}$ edition, University Science Books, Sausalito, 2006; Smith, March's Advanced Organic Chemistry: Reactions, Mechanism, and Structure, $7^{th}$ Edition, John Wiley & Sons, Inc., New York, 2013; Larock, Comprehensive Organic Transformations, 3$^{rd}$ Edition, John Wiley & Sons, Inc., New York, 2018; and Carruthers, Some Modern Methods of Organic Synthesis, 3$^{rd}$ Edition, Cambridge University Press, Cambridge, 1987.

The term "alkyl," as used herein, means a straight or branched saturated hydrocarbon chain containing from 1 to 16 carbon atoms ($C_1$-$C_{16}$ alkyl), for example 1 to 14 carbon atoms ($C_1$-$C_{14}$ alkyl), 1 to 12 carbon atoms ($C_1$-$C_{12}$ alkyl), 1 to 10 carbon atoms ($C_1$-$C_{10}$ alkyl), 1 to 8 carbon atoms ($C_1$-$C_8$ alkyl), 1 to 6 carbon atoms ($C_1$-$C_6$ alkyl), or 1 to 4 carbon atoms ($C_1$-$C_4$ alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, and n-dodecyl.

The term "alkenyl," as used herein, refers to a straight or branched hydrocarbon chain containing from 2 to 16 carbon atoms and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl," as used herein, refers to a straight or branched hydrocarbon chain containing from 2 to 16 carbon atoms and containing at least one carbon-carbon triple bond. Representative examples of alkynyl include, but are not limited to, ethynyl, propynyl, and butynyl.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "aryl," as used herein, refers to a phenyl group, or a bicyclic or tricyclic aromatic fused ring system. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl and phenanthrenyl. The term "aryl" as used herein also encompasses aryl groups substituted with another aryl group (e.g., biphenyl).

The term "cycloalkyl" as used herein, refers to a saturated carbocyclic ring system containing three to ten carbon atoms and zero heteroatoms. The cycloalkyl may be monocyclic, bicyclic, bridged, fused, or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, bicyclo [1.1.1]pentanyl, bicyclo[2.2.1]heptanyl, bicyclo[3.2.1]octanyl, and bicyclo[5.2.0]nonanyl.

The term "halogen" or "halo," as used herein, means F, Cl, Br, or I.

The term "haloalkyl," as used herein, means an alkyl group, as defined herein, in which one or more hydrogen atoms are replaced by a halogen. For example, one, two, three, four, five, six, seven or eight hydrogen atoms can be replaced by a halogen, or all hydrogen atoms can be replaced by a halogen. Representative examples of haloalkyl include, but are not limited to, fluoromethyl, difluoromethyl, trifluoromethyl, chloromethyl, dichloromethyl, trichloromethyl, 2-fluoroethyl, 2,2-difluoroethyl, 2,2,2-trifluoroethyl, perfluoroethyl, 2-fluoro-2-methylpropyl, and 3,3,3-trifluoropropyl.

The term "haloalkoxy," as used herein, means at least one haloalkyl group, as defined herein, is appended to the parent molecular moiety through an oxygen atom.

The term "heteroaryl," as used herein, refers to an aromatic monocyclic ring or an aromatic bicyclic ring system or an aromatic tricyclic ring system having at least one heteroatom. The aromatic monocyclic rings are five or six membered rings containing at least one heteroatom independently selected from the group consisting of N, O, and S (e.g. 1, 2, 3, or 4 heteroatoms independently selected from O, S, and N). The five-membered aromatic monocyclic rings have two double bonds and the six membered six membered aromatic monocyclic rings have three double bonds. The bicyclic heteroaryl groups are exemplified by a monocyclic heteroaryl ring appended fused to a monocyclic aryl group, as defined herein, or a monocyclic heteroaryl group, as defined herein. The tricyclic heteroaryl groups are exemplified by a monocyclic heteroaryl ring fused to two rings independently selected from a monocyclic aryl group, as defined herein or a monocyclic heteroaryl group as defined herein. Representative examples of monocyclic heteroaryl include, but are not limited to, pyridinyl (including pyridin-2-yl, pyridin-3-yl, pyridin-4-yl), pyrimidinyl, pyrazinyl, pyridazinyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, furanyl, oxazolyl, isoxazolyl, 1,2,4-triazinyl, and 1,3,5-triazinyl. Representative examples of bicyclic heteroaryl include, but are not limited to, benzimidazolyl, benzodioxolyl, benzofuranyl, benzooxadiazolyl, benzopyrazolyl, benzothiazolyl, benzothienyl, benzotriazolyl, benzoxadiazolyl, benzoxazolyl, chromenyl, imidazopyridine, imidazothiazolyl, indazolyl, indolyl, isobenzofuranyl, isoindolyl, isoquinolinyl, naphthyridinyl, purinyl, pyridoimidazolyl, quinazolinyl, quinolinyl, quinoxalinyl, thiazolopyridinyl, thiazolopyrimidinyl, thienopyrrolyl, and thienothienyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3] heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings.

The term "hydroxy," as used herein, means an —OH group.

The term "hydroxyalkyl," as used herein, refers to an alkyl group, as defined herein, substituted with at least one hydroxy group. Representative examples of hydroxyalkyl include, but are not limited to, hydroxymethyl, 2-hydroxyethyl, 3-hydroxypropyl, 2,3-dihydroxypropyl, 2,3-dihydroxypentyl, 4-hydroxybutyl, 2-ethyl-4-hydroxyheptyl, 3,4-dihydroxybutyl, and 5-hydroxypentyl.

The term "hydroxyhaloalkyl," as used herein, refers to a haloalkyl group, as defined herein, substituted with at least one hydroxy group.

The term "hydrophobic amino acid," as used herein, refers to an amino acid having a side chain that is uncharged at physiological pH, is not polar, and is generally repelled by aqueous solution. Exemplary hydrophobic amino acids include glycine, alanine, valine, leucine, isoleucine, proline, phenylalanine, methionine, and tryptophan.

In some instances, the number of carbon atoms in a group (e.g., alkyl, alkoxy, or cycloalkyl) is indicated by the prefix "$C_{x-}C_{y-}$", wherein x is the minimum and y is the maximum number of carbon atoms in the group. Thus, for example, "$C_1$-$C_3$-alkyl" refers to an alkyl group containing from 1 to 3 carbon atoms.

The term "substituent" refers to a group substituted on an atom of the indicated group. When a group or moiety can be substituted, the term "substituted" indicates that one or more (e.g., 1, 2, 3, 4, 5, or 6; in some embodiments 1, 2, or 3; and in other embodiments 1 or 2) hydrogens on the group indicated in the expression using "substituted" can be replaced with a selection of recited indicated groups or with a suitable group known to those of skill in the art (e.g., one or more of the groups recited below). In some embodiments, the substitutable group may be a heteroatom; for example, a sulfur atom can be substituted with one or two oxo groups. Substituent groups include, but are not limited to, halo, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of," and "consisting essentially of" the embodiments or elements presented herein, whether explicitly set forth or not.

The singular forms "a," "and" and "the" include plural references unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

DETAILED DESCRIPTION OF THE INVENTION

The present invention relates to compounds that are activators of the Alpha$_{1A}$-Adrenergic Receptor ($\alpha_{1A}$-AR) and methods of using such compounds: for treating neurological conditions, for cardio-protection, and for treating other conditions. In certain embodiments, the $\alpha_{1A}$-AR activator compound is within Formula I. In certain embodiments, the neurological condition is Alzheimer's disease, neurodegeneration, benign prostatic hyperplasia, memory loss, depression, or Parkinson's disease.

The compounds include compounds of formula (I):

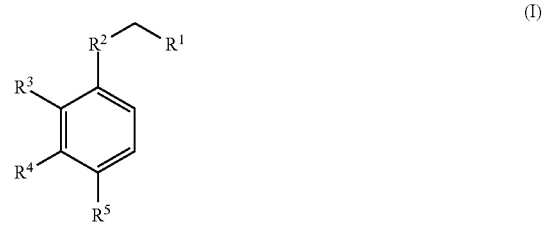

or a pharmaceutically acceptable salt thereof, wherein:

R¹ is a 5- or 6-membered heteroaryl ring having 1, 2, or 3 nitrogen atoms, a 5- or 6-membered heterocyclyl ring having 1, 2, or 3 nitrogen atoms, or a guanidinyl group;

R² is —X—(CH$_2$)$_m$—, wherein X is selected from —O—, —NH—, —S—, and —CH$_2$—, and wherein m is 0, 1, or 2;

R³ is selected from $C_2$-$C_6$ alkyl, $C_2$-$C_6$ alkenyl, $C_2$-$C_6$ alkynyl, $C_2$-$C_6$ hydroxyalkyl, $C_2$-$C_6$ haloalkyl, $C_2$-$C_6$ hydroxyhaloalkyl, $C_3$-$C_6$ cycloalkyl, aryl, halo, a hydrophobic amino acid moiety, and —(CHR$^a$)$_n$—R⁶, wherein:

R$^a$ is selected from hydrogen and hydroxy;

n is 1 or 2; and

R⁶ is selected from aryl, $C_3$-$C_6$ cycloalkyl, a 3- to 6-membered heterocyclic ring having 1, 2, or 3 heteroatoms selected from O, N, and S;

R⁴ is selected from —NR$^b$—SO$_2$—R⁷, —(CR$^c$R$^d$)—SO$_2$—R⁷, and —(CR$^e$R$^f$)$_p$—R⁸, wherein:

R$^b$ is selected from hydrogen, $C_1$-$C_3$ alkyl and $C_1$-$C_3$ haloalkyl;

R$^c$ and R$^d$ are each independently selected from hydrogen and methyl, or R$^c$ and R$^d$ are taken together with the carbon atom to which they are attached to form a $C_3$-$C_4$ cycloalkyl group;

R$^e$ and R$^f$ are each independently selected from hydrogen and halo;

p is 0 or 1;

R⁷ is selected from hydrogen, $C_1$-$C_3$ alkyl, $C_1$-$C_3$ haloalkyl, and $C_3$-$C_6$ cycloalkyl; and R⁸ is selected from $C_1$-$C_4$ alkoxy, $C_1$-$C_4$ haloalkoxy, hydroxy, —COOH, —CONH$_2$, and a 5-membered heteroaryl having 1, 2, or 3 nitrogen atoms; and R⁵ is selected from hydrogen, halo, and any of the groups indicated for R³ and R⁴; wherein each aryl, heteroaryl, cycloalkyl, and heterocyclyl can be independently unsubstituted or substituted with 1, 2, or 3 substituents independently selected from hydroxy, halo, $C_1$-$C_3$ alkyl, $C_1$-$C_3$ haloalkyl, and oxo.

In some embodiments, R¹ is selected from imidazolinyl, imidazolyl, triazolyl, pyrrolyl, pyrazolyl, imidazolidinyl, and tetrahydropyrimidinyl. In some embodiments, R¹ is selected from 4,5-dihydroimidazol-2-yl, imidazol-2-yl, pyrazol-1-yl, 1,2,3-triazol-2-yl, 1,2,3-triazol-1-yl, and 1,4,5,6-tetrahydropyrimidin-2-yl. In some embodiments, R¹ is selected from the following:

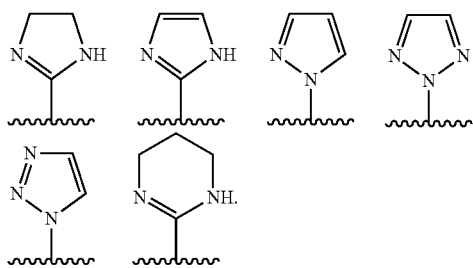

In some embodiments, R² is selected from —O— and —CH$_2$—. In some embodiments, R² is —O—. In some embodiments, R² is —CH$_2$—.

In some embodiments, the compound has formula (Ia):

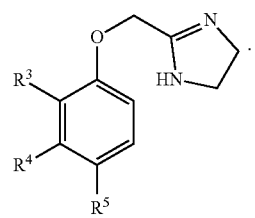

(Ia)

In some embodiments, R³ is selected from $C_2$-$C_6$ alkyl, $C_2$-$C_6$ hydroxyalkyl, $C_2$-$C_6$ haloalkyl, $C_2$-$C_6$ hydroxyhaloalkyl, halo, and —(CHR$^a$)$_n$—R⁶. In some embodiments, R³ is $C_2$-$C_6$ alkyl. In some embodiments, R³ is $C_3$-$C_6$ alkyl. In some embodiments, R³ is $C_4$-$C_6$ alkyl. In some embodiments, R³ is isobutyl. In some embodiments, R³ is isopentyl. In some embodiments, R³ is halo (e.g., bromo).

In some embodiments, R⁴ is —NR$^b$—SO$_2$—R⁷ or —(CR$^c$R$^d$)—SO$_2$—R⁷. In some embodiments, R⁴ is —NR$^b$—SO$_2$—R⁷, R$^b$ is $C_1$-$C_3$ alkyl, and R⁷ is hydrogen or $C_1$-$C_3$ alkyl. In some embodiments, R⁴ is —NR$^b$—SO$_2$—R⁷, R$^b$ is $C_1$-$C_3$ alkyl, and R⁷ is $C_1$-$C_3$ alkyl. In some embodiments, R⁴ is —N(CH$_3$)—SO$_2$—CH$_3$.

In some embodiments, R⁵ is selected from hydrogen and halo. In some embodiments, R⁵ is hydrogen. In some embodiments, R⁵ is halo (e.g., fluoro or chloro). In some embodiments, R⁵ has the same definition as R⁴; for example, in some embodiments, R⁵ is —NR$^b$—SO$_2$—R⁷, wherein R$^b$ is $C_1$-$C_3$ alkyl, and R⁷ is $C_1$-$C_3$ alkyl (e.g., R⁵ is —N(CH$_3$)—SO$_2$—CH$_3$).

In some embodiments, the compound is selected from:

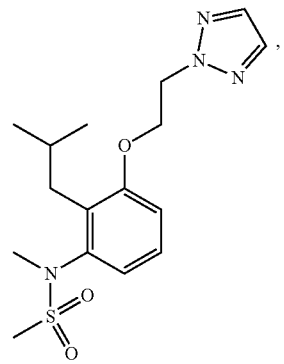

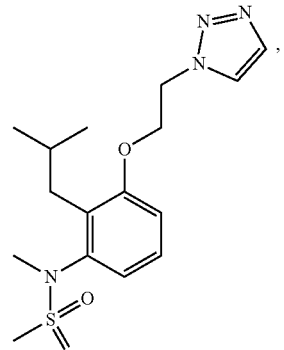

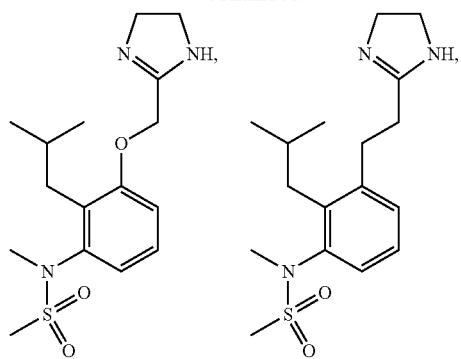
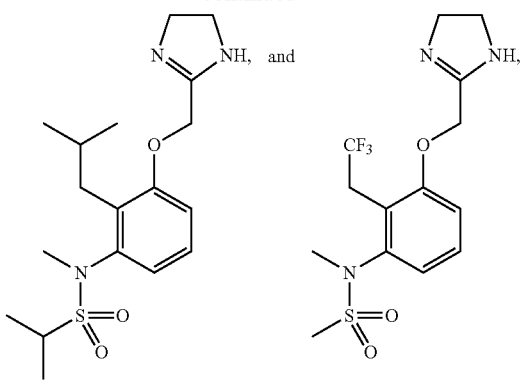
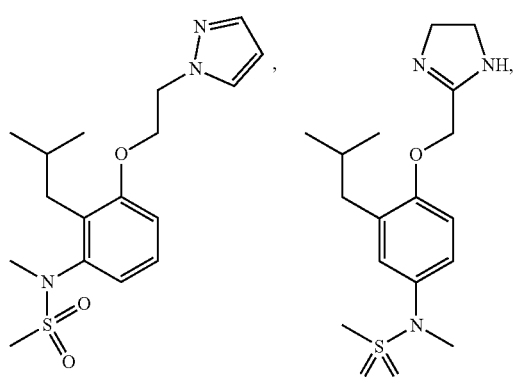
or a pharmaceutically acceptable salt thereof.
In some embodiments, the compound is selected from:
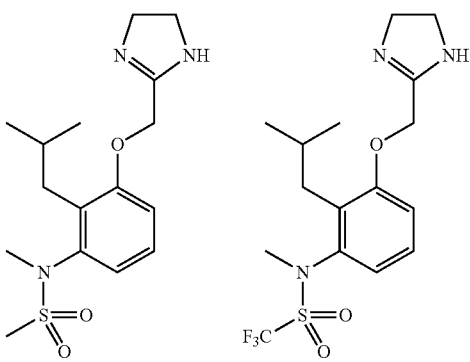
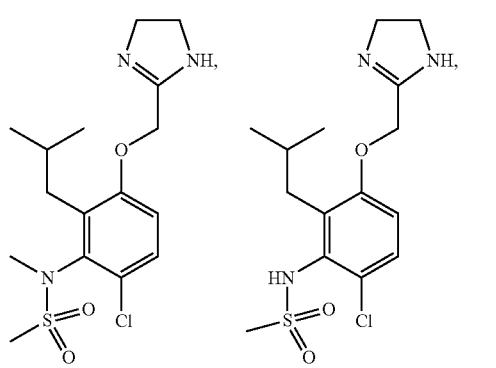
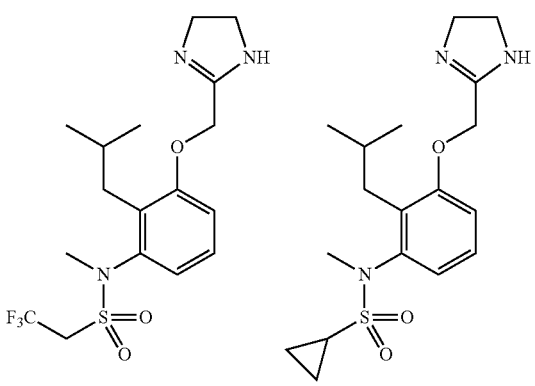
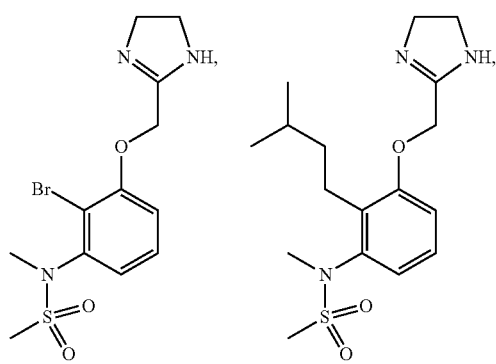
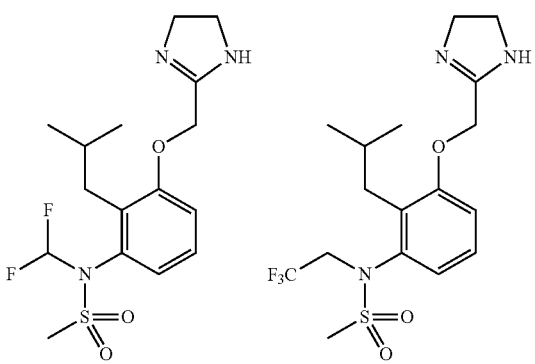

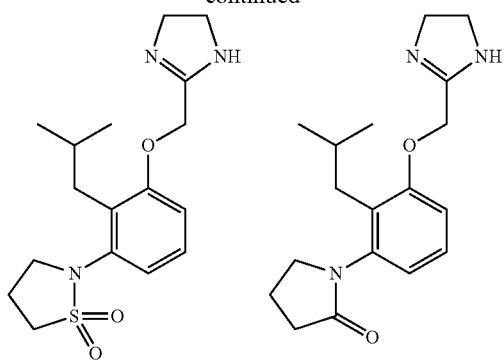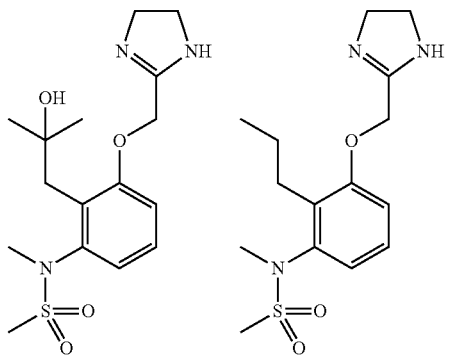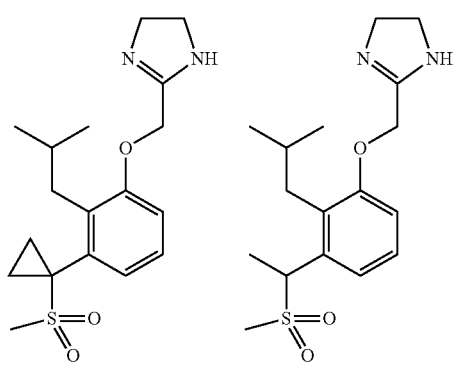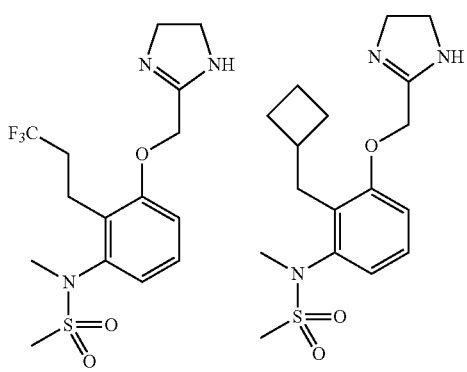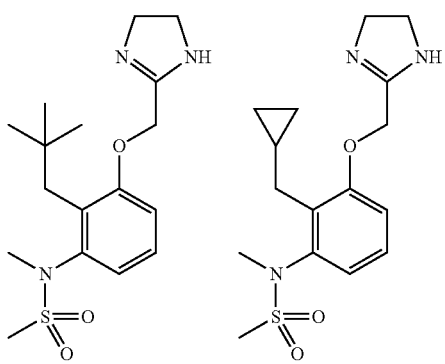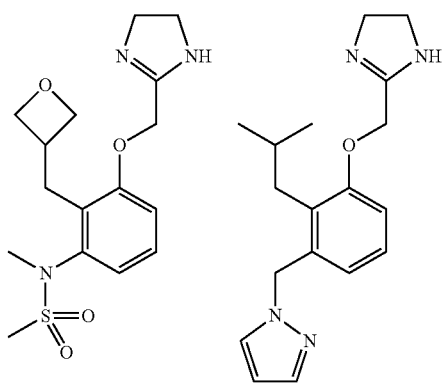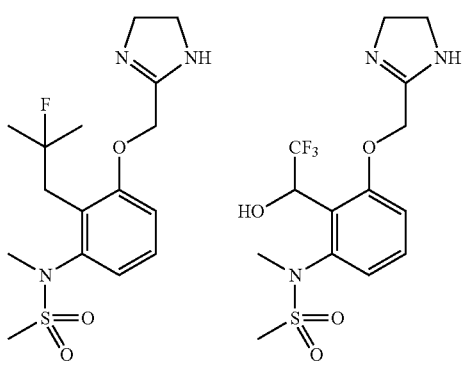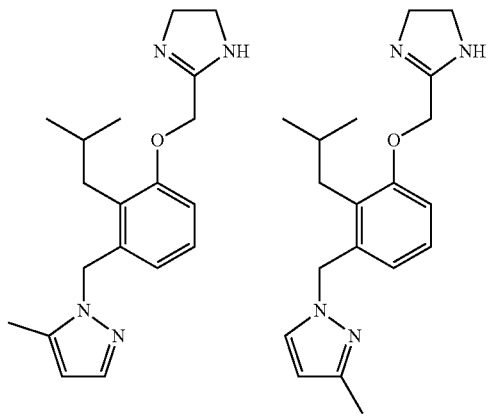

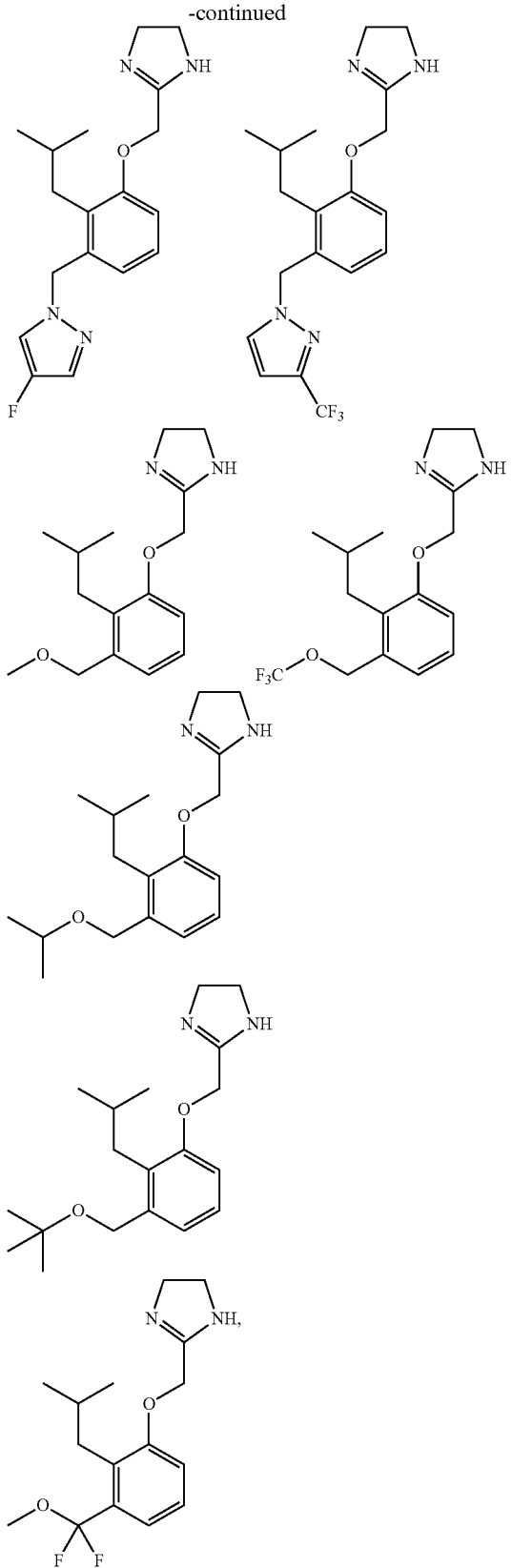

or a pharmaceutically acceptable salt thereof.

The disclosed compounds may exist as pharmaceutically acceptable salts. The salts may be prepared during the final isolation and purification of the compounds or separately by reacting the compounds with a suitable acid or base. For example, a compound may be dissolved in a suitable solvent and treated with at least one equivalent of an acid, such as hydrochloric acid. Alternatively, an amino group also be quaternized with alkyl chlorides, bromides and iodides such as methyl, ethyl, propyl, isopropyl, butyl, lauryl, myristyl, stearyl and the like. The resulting salt may precipitate out and be isolated by filtration and dried under reduced pressure. Alternatively, the solvent and excess acid may be removed under reduced pressure to provide a salt.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethyl aniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

In some embodiments, the compound is not in a salt form. In some embodiments, the compound is in the form of a pharmaceutically acceptable salt. In some embodiments, compound is in the form of a hydrochloride salt.

Some of the compounds of the disclosure have at least one asymmetric center. Additional asymmetric centers may be present depending upon the nature of the various substituents. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this disclosure. The present disclosure is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. The absolute stereochemistry of a compound may be determined by X-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art. Alternatively, any enantiomer of a compound may be obtained by stereoselective synthesis using optically pure starting materials or reagents of known configuration by methods well known in the art.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds are hydrogen, carbon, nitrogen, oxygen, phosphorus, sulfur, fluorine, and chlorine, such as, but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e. $^2$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

Several methods for preparing the compounds are illustrated in the Schemes and Examples herein. Starting materials are made according to procedures known in the art or as illustrated herein. The following examples are illustrative only and should not be construed as limiting the disclosure in any way. Abbreviations used in the following schemes include the following: AIBN is azobisisobutyronitrile; BuLi is n-butyllithium; CPhos is 2-dicyclohexylphosphino-2',6'-bis(N,N-dimethylamino)biphenyl; DCM is dichloromethane; IPA is isopropyl alcohol; MeOH is methanol; MsCl is methanesulfonyl chloride; NBS is N-bromosuccinimide; and THF is tetrahydrofuran.

The introduction of alkyl-linked groups into the R$^3$ position can be prepared according to Scheme 1, starting from bromination of the tolyl-derivative, which is then hydrolyzed, oxidized and undergoes a Wittig reaction to install the desired functionality. Hydrogenation of the resulting alkene affords the saturated R$^3$ group. Intermediates of this type are then used to furnish the final compounds. Compounds in Scheme 1 are represented in generic form, with substituents as noted in compound descriptions elsewhere herein. A more specific example leading to Compound 3 is outlined in Scheme 2.

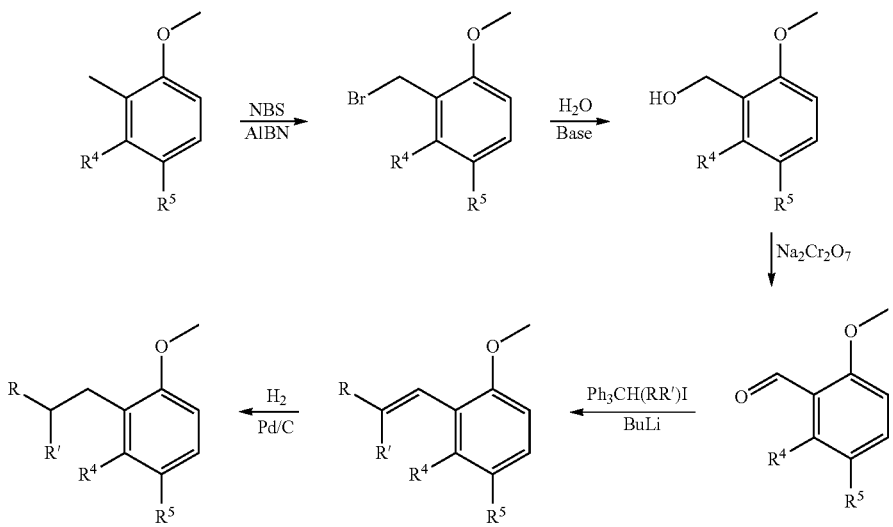

Scheme 1. Exemplary installation of certain R$^3$ groups

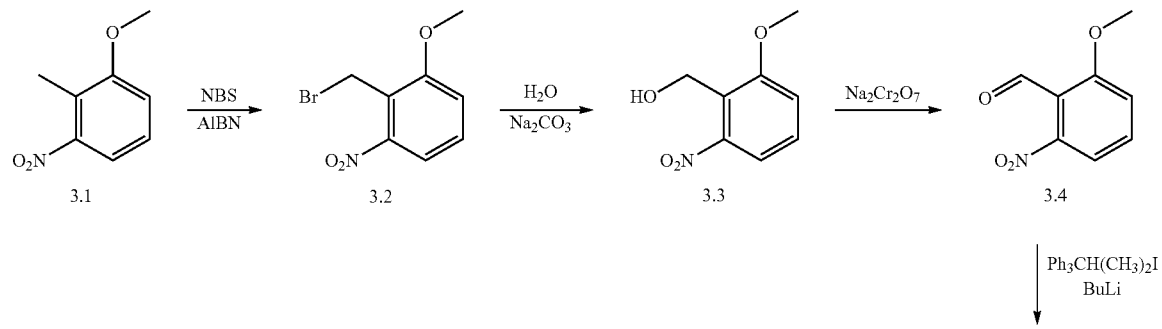

Scheme 2. Exemplary Synthesis of Compound 3

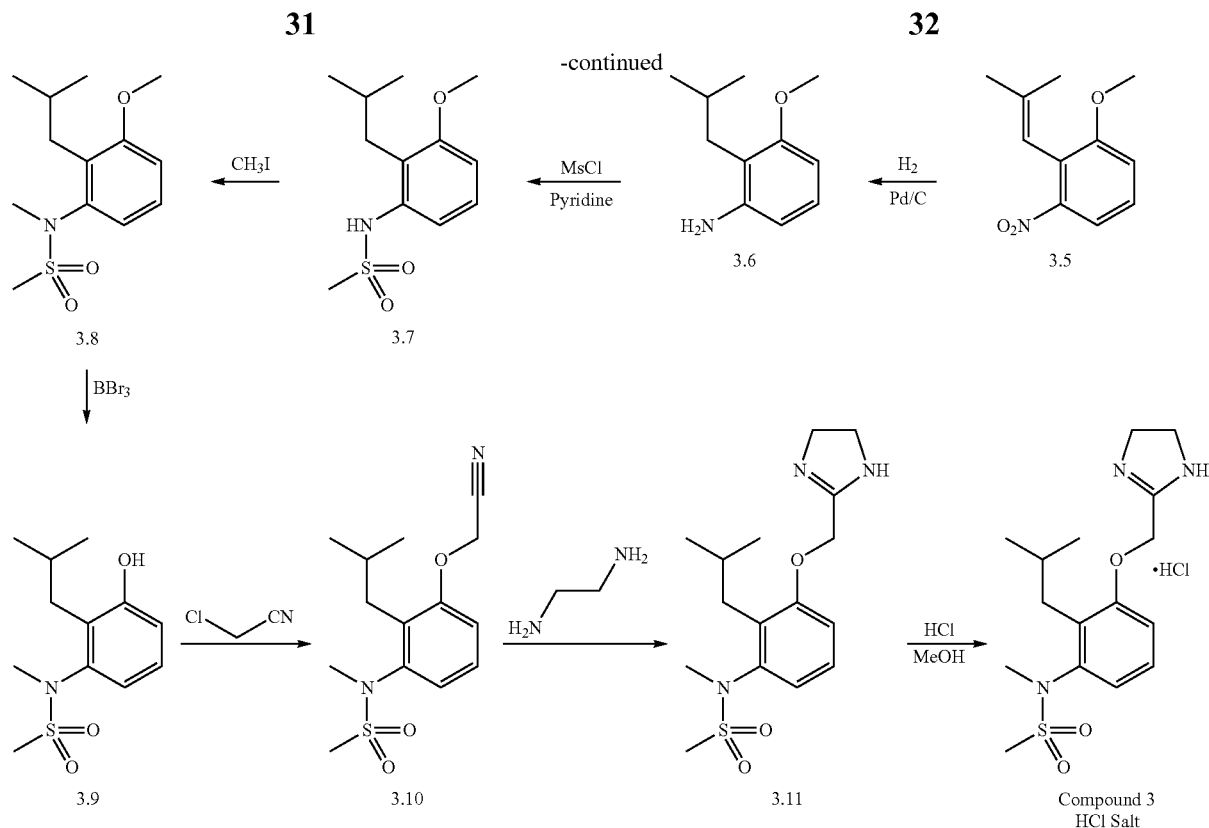
In another embodiment set forth in Scheme 3, treatment of the aryl bromide with an alkyl zinc bromide salt under Negishi conditions affords the corresponding alkyl-substituted intermediate.
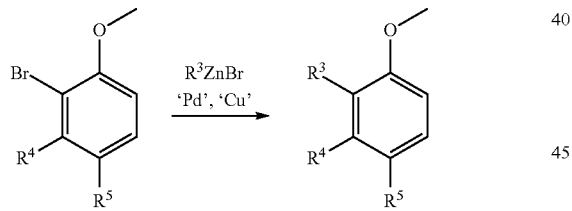
Scheme 4 demonstrates how this alternative synthesis can be incorporated into a route used to furnish Compound 3.
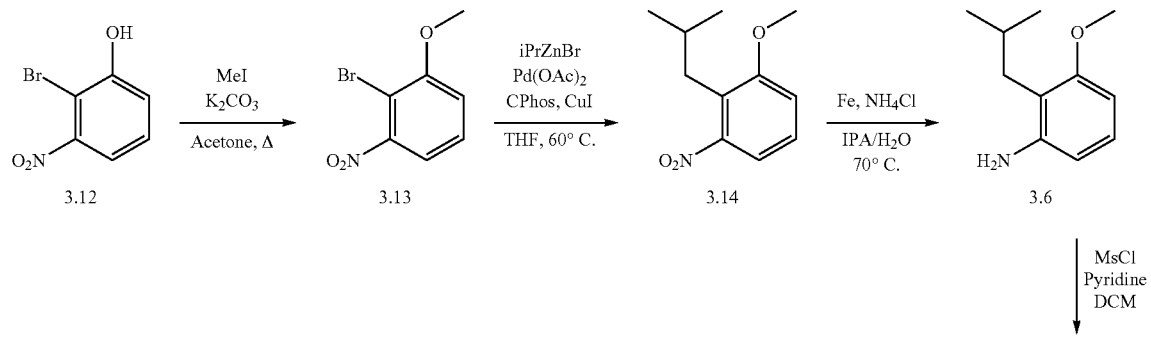

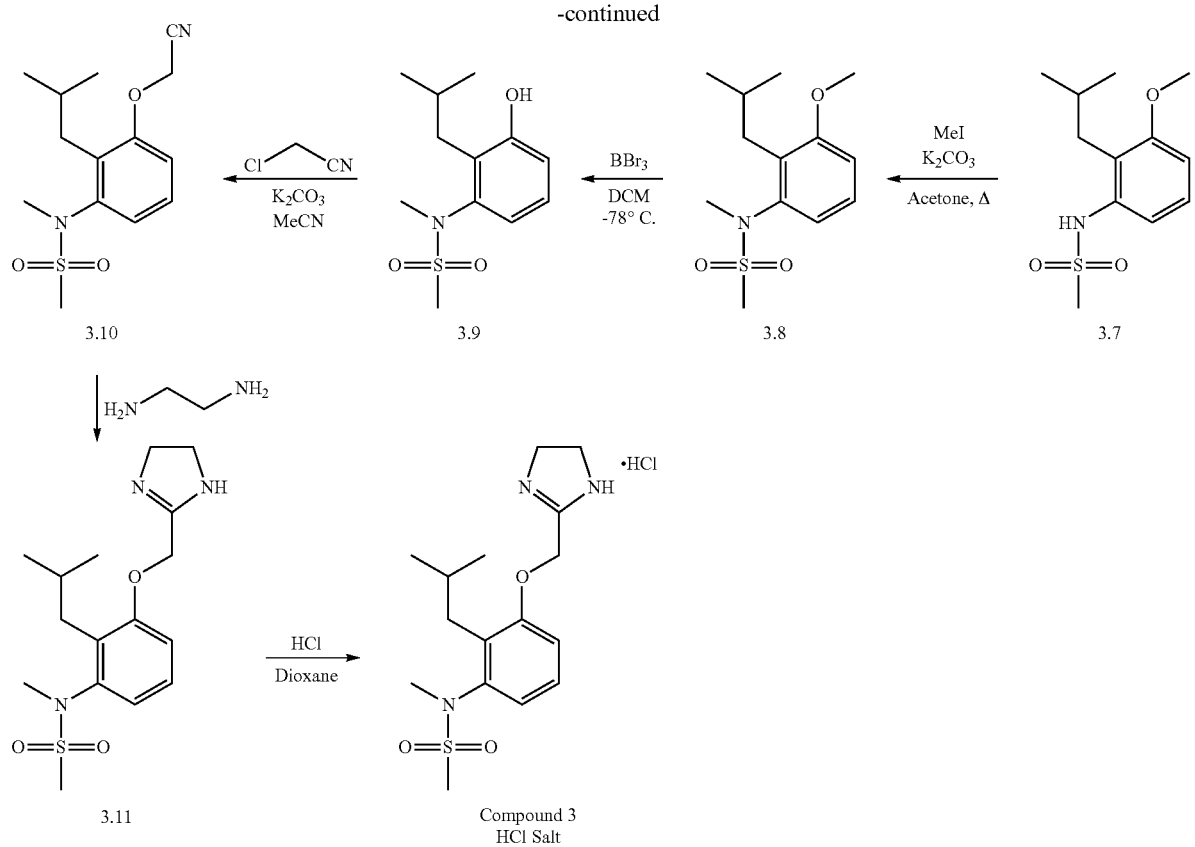

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

Reaction conditions and reaction times for each individual step can vary depending on the particular reactants employed and substituents present in the reactants used. Specific procedures are provided in the Examples section. Reactions can be worked up in the conventional manner, e.g., by eliminating the solvent from the residue and further purifying the compound according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis ($4^{th}$ ed.), John Wiley & Sons, NY (2006). Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

The compounds provided herein may be activators of Alpha$_{1A}$-Adrenergic Receptor ($\alpha_{1A}$-AR). In certain embodiments, the compounds may be brain-targeted PAMs (positive allosteric modulator) for a receptor system that is not solely localized in the brain. In certain embodiments, the compounds may be brain-targeted modulators since norepinephrine is mainly produced in the brain and there is no effect on the hormone, epinephrine, which circulates mainly in the periphery. In particular embodiments, the compounds may selectively increase the activation of the $\alpha_{1A}$-AR and target the brain, affecting the cognitive centers with no or limited side effects due to $\alpha_{1B}$- or $\alpha_{1D}$-AR activation. In particular embodiments, the compound may not increase IP by itself, and it therefore may have no effect in the periphery to increase blood pressure. In certain embodiments, the compounds herein have at least a 20-fold . . . 35-fold . . . or 50-fold selectivity for $\alpha_{1A}$-AR compared to other sub-types (e.g., $\alpha_1$, $\alpha_{1D}$-AR, and/or crossover, $\beta$-AR, and/or $\alpha_2$-ARs).

While not limited to any particular mechanism, and an understanding of the mechanism is not necessary to practice the invention, the $\alpha_{1A}$-AR activating compounds described herein are believed to useful for treating Alzheimer's disease, improving cognition, and for long-term potentiation (LTP), neurogenesis, and neurotransmission/memory, for a number of reasons. It has been shown that the $\alpha_{1A}$-AR mRNA subtype was significantly reduced in specific layers of the prefrontal cortex in patients with AD (29, herein incorporated by reference). Also, the $\alpha_1$-AR receptor density in AD is also reduced by 25% (30, herein incorporated by reference). An $\alpha_{1A}$-AR polymorphism is also associated with AD (31, herein incorporated by reference). The $\alpha_{1A}$-AR subtype is also highly expressed in the hippocampus in both mouse and humans (32, herein incorporated by reference). $\alpha_1$-ARs play a role in learning and memory (33). Some limited early studies using non-selective ligands have suggested that $\alpha_1$-ARs inhibit spatial memory and consolidation (34-35), while most other studies imply that $\alpha_1$-ARs facilitate memory (36), motor and motivational behavior (37), and memory retention and storage (38-44). Further, $\alpha_1$-ARs can modulate NMDA receptor activation in the hippocampus (45-46) that can have consequences on LTP (47-48). There is also a direct role for $\alpha_1$-ARs in promoting LTP and synaptic plasticity in the hippocampus (49-51) as well as long-term depression (52-53). The hippocampus displays distinct patterns of network activity that are synchronized in order to form memories. $\alpha_1$-AR activation can slow or stop the normal spontaneous discharges of the CA3 pyramidal neurons to the hippocampal CA1 subfield (54-55). Stimulation of $\alpha_1$-ARs can also abruptly suppress the generation of sharp wave-ripple complexes in hippocampal slices allowing for rapid interruption of activity, such as those needed when switching synchronized hippocampal activity into attention-related network states for encoding new information (56) and are needed for synaptic plasticity (57). Studies using several training tasks suggest that norepinephrine infused into the basolateral nucleus of the amygdala (BLA) immediately after training enhances memory by binding to both $\beta$- and $\alpha_1$-ARs at postsynaptic sites (58-63) through $\beta$-AR-mediated adenosine 3',5'-cyclic monophosphate (cAMP) and cAMP-dependent protein kinase (PKA) formation. Infusion of 8-Br-cAMP also enhanced memory consolidation in a dose-dependent manner (60, 62). While $\beta$-AR density is moderate in the BLA, $\alpha_{1A}$-AR density is very high (25). Activation of $\beta$-adrenoceptors affects adenylate cyclase and stimulates the cAMP/PKA signal transduction pathway. In contrast, $\alpha_1$-ARs were previously thought to play only a modulatory role in potentiating the response induced by $\beta$-adrenoceptor stimulation and, thus, activate cAMP only indirectly (64-67). However, $\alpha_1$-AR have been shown to mediate directly their own cAMP response (68-70) and particularly in the brain during learning and memory function even when $\beta$-ARs are inactivated (67, 71).

The compounds described herein may be used to treat neurodegenerative disease and other conditions, such as: cognitive decline as reviewed in (20), improve depression, mood (24), metabolism, diabetes (e.g., by increasing fatty acid oxidation, increasing glucose uptake and glucose tolerance (72)), prolong lifespan (73), arousal (74), satiety, reproduction (75-76), seizures (22), neurodegenerative diseases, such as Parkinson disease, autonomic failure, and Multiple System Atrophy (20-21, 25-26), and ischemia (heart attack damage) (27), reverse heart failure (77), and provide a cardio-protective effect.

In some embodiments, the compounds herein may be antagonists for the inositol phosphate release. In particular embodiments, the compounds may be used to treat benign prostatic hypertrophy.

The present invention provides pharmaceutical compositions which may comprise one or more forms of a compound of Formula I, alone or in combination with at least one other agent, such as a stabilizing compound, or Alzheimer's therapeutic, and may be administered in any sterile, biocompatible pharmaceutical carrier, including, but not limited to, saline, buffered saline, dextrose, and water.

The methods of the present invention find use in treating (e.g., prophylactically or therapeutically) diseases or altering physiological states. A compound of Formula I (can be administered to a subject (e.g., a patient) intravenously in a pharmaceutically acceptable carrier such as physiological saline. Standard methods for intracellular delivery of compounds can be used (e.g., delivery via liposome). Such methods are well known to those of ordinary skill in the art. The formulations of this invention are useful for parenteral administration, such as intravenous, subcutaneous, intramuscular, and intraperitoneal.

As is well known in the medical arts, dosages for any one subject may depend upon many factors, including the patient's size, body surface area, age, the particular compound to be administered, sex, time and route of administration, general health, and interaction with other drugs being concurrently administered.

Accordingly, in some embodiments of the present invention, compositions and/or formulations comprising a compound of Formula I can be administered to a subject alone, or in combination with other forms of a compound of Formula I, drugs, small molecules, or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, compositions comprising a compound of Formula I may be administered alone to individuals subject to or suffering from a disease or condition (e.g., Alzheimer's disease, Parkinson's disease, diabetes, etc.). Compositions comprising a compound of Formula I may be added to a nutritional drink or food (e.g., ENSURE, POWERBAR, or the like), a multi-vitamin, nutritional products, food products, etc. for daily consumption.

Depending on the target sought to be altered by treatment, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of the pharmaceutical agent may be that amount that alters the expression of a specific gene. Determination of effective amounts is well within the capability of those skilled in the art, especially in light of the disclosure provided herein. In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes). Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc.; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations which can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For compositions or formulations comprising a compound of Formula I, conditions indicated on the label may include treatment of condition related to prophylactic or therapeutic treatment of neurodegenerative disease or cognitive function.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the methods of the invention, the therapeutically effective dose can be estimated initially from cell culture assays. Then, preferably, dosage can be formulated in animal models (particularly murine models) to achieve a desirable circulating concentration range. A therapeutically effective dose refers to that amount of which ameliorates or prevents symptoms of a disease state or condition (e.g., through altering gene expression) Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds which exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage may be chosen by a subject or by a physician in view of the patient to be treated. Dosage and administration are adjusted to provide sufficient levels of the active moiety or to maintain the desired effect (e.g., alteration of gene expression in a subject). Additional factors that may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation. In some embodiments, a compound of Formula I is administered at a daily dose of between 0.05 and 250 mg per day (e.g., administered to a subject in such a way so as to provide between 0.05 and 250 mg of a compound of Formula Ito the subject each day). Doses outside of 0.05 and 250 mg may be used. In some embodiments, a single dose of a compound of Formula I is administered once daily. In other embodiments, 2, 3, 4, or more doses may be administered each day (e.g., once in the morning and once at night, or once every 4 to 6 hours). For example, in some embodiments, a compound of Formula I is administered to a subject in three separate, more than three separate, two separate, or less than two separate doses. In some embodiments, the daily dose is administered in a time release capsule.

The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable. Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Thus, in some embodiments, pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semi-solids. The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product. Thus, in some embodiments, the compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

In some embodiments, the invention provide pharmaceutical compositions containing (a) one or more forms of a compound of Formula I and (b) one or more other agents (e.g., Alzheimer's therapeutic). Examples of such Alzheimer's therapeutic agents are described above. In some embodiments, two or more combined agents (e.g., Alzheimer's therapeutics) may be used together or sequentially.

The present invention also includes methods involving co-administration of compounds comprising a compound of Formula I described herein with one or more additional active agents (e.g., an Alzheimer's therapeutic, anti-oxidant, etc.). Indeed, it is a further aspect of this invention to provide methods for enhancing prior art therapies and/or pharmaceutical compositions by co-administering a composition comprising a compound of Formula I of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered agents may each be administered using different modes or different formulations.

The agent or agents to be co-administered depends on the type of condition being treated. For example, when the condition being treated is a neurodegenerative disease, the additional agent can be, for example, an Alzheimer's therapeutic, an ALS therapeutic, a Huntington's therapeutic, a benign prostatic hyperplasia therapeutic, or the like. When the condition being treated is diabetes, the additional agent can be a diabetes therapeutic. When the condition being treated is cognitive function, the additional agent can be an antioxidant. The additional agents to be co-administered, such as Alzheimer's therapeutics, diabetes therapeutics, or antioxidants, can be any of the well-known agents in the art, including, but not limited to, those that are currently in clinical use.

EXAMPLES

The following examples are provided in order to demonstrate and further illustrate certain preferred embodiments and aspects of the present invention and are not to be construed as limiting the scope thereof.

Example 1

Synthesis of Compound 3

General Procedures. Chemical shift values are reported in δ values (parts per million, ppm) relative to the standard chemical shift for the hydrogen residue peak in the deuterated solvent, $CDCl_3$ or DMSO-$d_6$. The coupling constant (J) values are expressed in hertz (Hz). Thin-layer chromatography (TLC) was performed on silica gel plates. Compounds on TLC were visualized by illumination under UV light (254 nm), or dipped into 10% phosphomolybdic acid in ethanol, followed by charring on a hot plate. Solvent systems are expressed as a percentage of the more polar component with respect to total volume (v/v %). Silica gel (300-400 mesh) was used for flash column chromatography. Evaporations were carried out under reduced pressure (vacuum pump) with the bath temperature below 50° C. unless specified otherwise. Materials obtained from commercial suppliers were used without further purification.

All operations with air sensitive compounds were carried out under dry nitrogen or argon using Schlenk techniques. HPLC measurements were Agilent 1100 and MS measurements were Agilent 6110, NMR spectra were recorded on Switzerland Bruker Avance III 400 400 MHz superconducting Fourier nuclear magnetic resonance (NMR) spectrometer.

Abbreviations used in this Example include the following: AIBN is azobisisobutyronitrile; BuLi is n-butyllithium; DCM is dichloromethane; DMF is N,N-dimethylformamide; DMSO is dimethylsulfoxide; EtOAc is ethyl acetate; EtOH is ethanol; MeOH is methanol; MsCl is methanesulfonyl chloride; NBS is N-bromosuccinimide; and THF is tetrahydrofuran.

A synthetic scheme with compound numbers can be found in Scheme 2 in the Detailed Description.

2-Bromomethyl-1-methoxy-3-nitro-benzene (3.2): 1-Methoxy-2-methyl-3-nitro-benzene (3 g, 17.9 mmol) was dissolved in $CCl_4$ (30 mL), then AIBN (0.589 g, 3.59 mmol) and NBS (3.36 g, 18.8 mmol) were added to the solution. The reaction mixture was stirred at room temperature for 10 min, then it was heated to reflux overnight under $N_2$. When the reaction was complete, it was concentrated and purified on silica gel column chromatography using EtOAc/Petroether (v/v 1:8) as eluent to give 2-bromomethyl-1-methoxy-3-nitro-benzene (3.2) as a yellow powder (4.3 g, 97% yield). [MS m/z: 246 and 248 (M+1)].

(2-Methoxy-6-nitro-phenyl)-methanol (3.3): 2-Bromomethyl-1-methoxy-3-nitro-benzene (3.2) (4.3 g, 17.49 mmol) was dissolved in $Na_2CO_3$ solution (3.7 g, 34.9 mmol in 50 mL water), the reaction mixture was heated at 100° C. for 3 h. After cooling to room temperature, it was diluted and extracted with EtOAc (3×50 mL), the organic phase was combined, dried over anhydrous sodium sulfate, then concentrated to give (2-methoxy-6-nitro-phenyl)-methanol (3.3) (2.8 g, 88% yield) as a pale yellow oil. [MS m/z: 184 (M+1)]. The crude product was directly used in next step.

2-Methoxy-6-nitro-benzaldehyde (3.4): To a solution of (2-methoxy-6-nitro-phenyl)-methanol (3.3) (2.8 g, 15.3 mmol) in water (30 mL) $Na_2Cr_2O_7$ (5 g, 15.3 mmol) was added slowly in 30 min. The reaction mixture was heated to 100° C. for 2 h, and the reaction was monitored by LC-MS. After the reaction was complete, it was cooled to room temperature, then diluted and extracted with EtOAc (3×50 mL), the organic phase was combined, dried over anhydrous sodium sulfate, then concentrated and purified on silica gel column chromatography using EtOAc/Petroether (v/v 1:6) to provide 2-methoxy-6-nitro-benzaldehyde (3.4) (2.3 g, 83% yield) as a yellow oil. [MS m/z:182 (M+1)].

1-Methoxy-2-(2-methyl-propenyl)-3-nitro-benzene (3.5): (2-Propyl)triphenylphosphonium iodide (1.55 g, 3.59 mmol) was dissolved in dry THF (20 mL), then it was cooled to −78° C. under $N_2$ and n-BuLi (1.5 mL, 3.82 mmol, 2.5 mol/L in THF) was added dropwise to the reaction system in 10 min. Then the temperature was allowed to reach 0° C. slowly. Then it was cooled to −78° C. again, 2-methoxy-6-nitro-benzaldehyde (3.4) (0.49 g, 2.7 mmol) in THF was added dropwise in 30 min. After the addition, the reaction was monitored by TLC. Then it was quenched with water (20 mL), extracted with EtOAc (3×30 mL). The organic phase was combined, dried over anhydrous sodium sulfate, then concentrated and purified on silica gel column chromatography using EtOAc/Petroether (v/v 1:5) as eluent to provide 1-methoxy-2-(2-methyl-propenyl)-3-nitro-benzene (3.5) (400 mg, 70% yield) as a yellow oil. [MS m/z: 208 (M+1)].

2-Isobutyl-3-methoxy-phenylamine (3.6): 1-Methoxy-2-(2-methyl-propenyl)-3-nitro-benzene (3.5) (400 mg, 1.93 mmol) was dissolved in EtOH (30 mL), then 10% Pd/C (205 mg, 0.193 mmol) was added. The reaction mixture was stirred under $H_2$ (60 psi) for 6 h. LC-MS showed reaction was complete. It was filtered and concentrated to give 2-isobutyl-3-methoxy-phenylamine (3.6) (340 mg, 98% yield) as a colorless oil. [MS m/z: 180 (M+1)].

N-(2-Isobutyl-3-methoxy-phenyl)-methanesulfonamide (3.7): 2-Isobutyl-3-methoxy-phenylamine (3.6) (340 mg, 1.89 mmol) was dissolved in DCM (30 mL), then pyridine (300 mg, 3.799 mol) was added. The reaction mixture was cooled to 0° C. and MsCl (215 mg, 1.89 mmol) was added dropwise. After 1 h the reaction was complete and it was extracted with DCM (3×30 mL), the organic phase was combined, dried over anhydrous sodium sulfate, then concentrated to give N-(2-isobutyl-3-methoxy-phenyl)-methanesulfonamide (3.7) (460 mg, 94% yield) as a white solid. [MS m/z: 280 (M+Na)].

N-(2-Isobutyl-3-methoxy-phenyl)-N-methyl-methanesulfonamide (3.8): To a solution of N-(2-isobutyl-3-methoxy-phenyl)-methanesulfonamide (3.7) (460 mg, 1.79 mmol) in DMF (20 mL) was added $K_2CO_3$ (494 mg, 3.58 mmol) and $CH_3I$ (508 mg, 3.58 mmol). The reaction mixture was stirred at rt overnight then water (50 mL) was added, it was extracted with DCM (3×40 mL). The combined organic phase was dried over anhydrous sodium sulfate and concentrated to give N-(2-isobutyl-3-methoxy-phenyl)-N-methyl-methanesulfonamide (3.8) (470 mg, 97% yield) as a white solid. [MS m/z: 272 (M+1)].

N-(3-Hydroxy-2-isobutyl-phenyl)-N-methyl-methanesulfonamide (3.9): To a solution of N-(2-isobutyl-3-methoxy-phenyl)-N-methyl-methanesulfonamide (3.8) (470 mg, 1.73 mmol) in DCM (30 mL) at 0° C. BBr$_3$ (867 mg, 3.47 mmol) was added dropwise. After 1 h the reaction was complete. It was quenched with 20% NaHCO$_3$ aq. solution (20 mL), and extracted with DCM (3×30 mL). The combined organic phase was dried over anhydrous sodium sulfate, then concentrated and purified on silica gel column chromatography using EtOAc/Petroether (v/v 1:1) to provide N-(3-hydroxy-2-isobutyl-phenyl)-N-methyl-methanesulfonamide (3.9) (410 mg, 92% yield) as a pale yellow solid. [MS m/z: 258 (M+1)].

N-(3-Cyanomethoxy-2-isobutyl-phenyl)-N-methyl-methanesulfonamide (3.10): To a solution of N-(3-hydroxy-2-isobutyl-phenyl)-N-methyl-methanesulfonamide (3.9) (410 mg, 1.59 mmol) in acetone (30 mL) was added chloroacetonitrile (235 mg, 3.18 mmol) and potassium carbonate (439 mg 3.18 mmol). The reaction mixture was stirred at room temperature overnight, then water (50 mL) was added, it was extracted with EtOAc (3×50 mL). The organic phase was combined, dried over anhydrous sodium sulfate, then concentrated and purified on silica gel column chromatography using EtOAc/Petroether (v/v 1:3) as eluent to give N-(3-cyanomethoxy-2-isobutyl-phenyl)-N-methyl-methanesulfonamide (3.10) (400 mg, 85% yield) as a white solid. [MS m/z: 319 (M+Na)].

N-[3-(4,5-Dihydro-1H-imidazol-2-ylmethoxy)-2-isobutyl-phenyl]-N-methyl-methanesulfonamide (3.11): The solution of N-(3-cyanomethoxy-2-isobutyl-phenyl)-N-methyl-methanesulfonamide (3.10) (400 mg, 1.35 mmol) in ethylenediamine (20 mL) was heated to 100° C. After 2 h water was added and extracted with EtOAc (3×50 mL). The combined organic phase was dried over anhydrous sodium sulfate, then concentrated and purified on silica gel column chromatography using MeOH/DCM (v/v 1:20) as eluent to give N-[3-(4,5-dihydro-1H-imidazol-2-ylmethoxy)-2-isobutyl-phenyl]-N-methyl-methanesulfonamide (3.11) (256 mg, 56% yield) as a colorless oil. [MS m/z: 340 (M+1)].

N-[3-(4,5-Dihydro-1H-imidazol-2-ylmethoxy)-2-isobutyl-phenyl]-N-methyl-methanesulfonamide (Compound 3) HCl Salt: N-[3-4,5-dihydro-1H-imidazol-2-ylmethoxy)-2-isobutyl-phenyl]-N-methyl-methanesulfonamide (3.11) (256 mg, 0.775 mmol) was dissolved in HCl in MeOH (1 mol/L, 20 mL). It was stirred at room temperature for 30 min, after removing solvent under vacuo N-[3-(4,5-dihydro-1H-imidazol-2-ylmethoxy)-2-isobutyl-phenyl]-N-methyl-methanesulfonamide (Compound 3) as the HCl salt (280 mg, 99% yield) was collected as a white powder. [MS m/z: 340 (M+1)]. $^1$H-NMR (400 MHz, DMSO-d$_6$) δ 10.30 (s, 2H), 7.29-7.26 (t, J=12.0 Hz, 1H), 7.19-7.17 (d, J=8.0 Hz, 1H), 7.00-6.98 (d, J=8.0 Hz, 1H), 5.11-5.03 (dd, J=16.0 Hz, 2H), 3.90 (s, 4H), 3.11 (s, 3H), 3.01 (s, 3H), 2.74-2.63 (m, 4H), 1.86-1.82 (m, 1H), 0.86-0.84 (d, J=8.0 Hz, 3H), 0.78-0.77 (d, J=4.0 Hz, 3H).

Example 2

Characterization Data for Compounds 1-2 and 4-10

Compounds 1-2 and 4-10 (structures shown in FIG. 1) were synthesized by methods similar to those illustrated herein for Compound 3. Characterization data is as follows.

Compound 1. MS: m/z=353.2 [M+H]$^+$. $^1$H NMR spectrum shown in FIG. 2A.

Compound 2. MS: m/z=353.2 [M+H]$^+$. $^1$H NMR spectrum shown in FIG. 2A. Note: Compounds 1 and 2 are regioisomers isolated from a single reaction mixture.

Compound 4. MS: m/z=338.2 [M+H]$^+$. $^1$H NMR spectrum shown in FIG. 2B.

Compound 5. MS: m/z=352.1 [M+H]$^+$. $^1$H NMR spectrum shown in FIG. 2C.

Compound 6. MS: m/z=340.1 [M+H]$^+$. $^1$H NMR spectrum shown in FIG. 2D.

Compound 7. MS: m/z=374.1 [M+H]$^+$. $^1$H NMR spectrum shown in FIG. 2E.

Compound 8. MS: m/z=359.9 [M+H]$^+$. $^1$H NMR spectrum shown in FIG. 2F.

Compound 9. MS: m/z=361.9, 363.9 [M+H]$^+$. $^1$HNMR spectrum shown in FIG. 2G.

Compound 10. MS: m/z=354.1 [M+H]$^+$. $^1$H NMR spectrum shown in FIG. 2H.

Example 3

Assay Data for Compounds 1-10

Materials and Methods:

Competition binding assays: These compounds were characterized for their ligand binding properties at the $\alpha_1$-AR subtypes. The binding affinities of Compounds 1-10 were determined in a series of competition-binding experiments with the $\alpha_1$-AR-selective antagonist [$^{125}$I]HEAT as the radioligand. Assays were performed in duplicate in HEM buffer, in a total assay volume of 1000 μl. Radioligand binding assays are composed of 5 ug of membranes, harvested from Rat-1 fibroblast cells expressing only one of the alpha1-AR subtypes, HEM buffer containing GTP (composed of 20 mM HEPES, pH 7.4, 1.4 mM EGTA, 12.5 mM MgCl$_2$, pH to 7.4), 0.5 mM GTP, 35-80 pM$^{125}$I-HEAT, and various doses of norepinephrine or epinephrine and incubated with shaking at 25° C. for 1-2 hours. The above conditions will convert all the conformations of the receptor into a single low affinity site. To show both high and low affinity sites of the receptor (typically seen with GPCR agonists), the GTP is removed from the binding buffer. Nonspecific binding was determined experimentally in the presence of $10^{-4}$ M phentolamine. Unbound radioactivity was separated from membrane-bound radioactivity by filtration through Whatman GF/C filter paper. Filters are washed five times with 5 ml of cold HEM buffer containing 0.5 mMGTP (if added to the binding buffer but not if it was not added to the binding buffer). Bound radioactivity remaining on the filters was counted on an ICN gamma counter operating at 79.8% efficiency. Data are analyzed using Graphpad Prism.

To determine the effects of compounds 1-10 on the binding affinity of norepinephrine or epinephrine, the competition binding assay was repeated as above with one dose of each individual compound (i.e. $10^{-5}$M) added to each concentration point. Data are normalized to the norepinephrine or epinephrine binding curve alone without the addition of the compound to measure its effect on binding.

cAMP assay: Cells expressing a single $\alpha_1$-adrenergic receptor subtype are washed and re-plated into 24-well plates in DMEM media without serum at approximately $2.4\times10^4$ cells/well. Cells are allowed to rest till the next day in a CO$_2$ incubator at 37° C. The cells are washed twice with DMEM (no serum), then 1 ml of DMEM is added to each well. Cells are pre-incubated for 45 mins-1 hour at 37° C. in a CO$_2$ incubator with 10 uM propranolol, followed by 100 uM IBMX for 30 minutes. Final DMSO concentration is at 0.05%. Norepinephrine or epinephrine is added in a dose response (1 dose per well) in addition to one of the Compounds 1-10 at one concentration (i.e. $10^{-5}$M). Cells are incubated for another 30 mins at 37° C. in a $CO_2$ incubator. The reaction is concluded by aspirating the media and adding 0.1M HCL. The mixture is incubated for 20 mins at room temperature. The cells are scraped and suspended until homogenous. The mixture is centrifuged at 1000 g for 10 mins and the supernatant assayed the same day according to a manufacturer's cAMP kit (Cayman Select Cyclic AMP EIA kit #501040). In a rapid cAMP screening assay for PAM effects, the above assay is modified by keeping the concentration of norepinephrine or epinephrine constant at its 100% Emax value ($10^{-4}$M) (for type I PAMs), followed by increasing concentrations of the test compounds; thereby demonstrating a dose-response curve and obtaining an Emax and potency (EC50) value for the test compound.

Total Inositol Phosphate assay: Cells expressing a single α1-adrenergic receptor subtypes are washed and re-plated into 6-well plates containing DMEM media at approximately $5\times10^5$ cells/well. Cells are allowed to rest till the next day in a $CO_2$ incubator at 37° C. The cells are washed twice with DMEM (no serum), then 2 ml of DMEM is added to each well. 2 ul of $^3$H-inositol (at 1 uCi/mL, Perkin-Elmer NET 114 005MC) and 10 mM LiCl is added to each well. The cells are incubated for 1 hour at 37° C. in a $CO_2$ incubator. Norepinephrine or epinephrine is added in a dose response (1 dose per well) in addition to one of the Compounds 1-10 at one concentration (i.e. $10^{-5}$M). The cells are incubated again for 1 hour at 37° C. in a $CO_2$ incubator. The media is aspirated and 1 mL of ice-cold 0.4M perchloric acid is added. The cells are scraped, transferred to a vial, then 1 mL 0.72M KOH/0.6M $KHCO_3$ is added, the tube vortexed and the contents centrifuged at 2000 rpm for 10 mins. The supernatant is removed and applied to BioRad polyprep columns packed with 1 mL of AG1-X8 resin (BioRad AG1-X8 resin 100-200 mesh #140-1444) in 0.1M formic acid in a holding tray which is over a plastic catch tray. The supernatant is allowed to naturally drip through the column then washed with 8 ml of 0.1M formic acid (2 ml at a time). The columns are transferred via the holding tray to a box of 20 ml scintillation vials so that the columns drip directly into the vials. Total inositol phosphates are eluted off the column with 2 ml of 0.1M formic acid/1M ammonium formate. The columns are eluted a second time into a new scintillation vial with another 2 ml of 0.1M formic acid/1M ammonium formate. 18 ml of Ecoscint A is added to each scintillation vial and vortexed. The vials are allowed to dark adapt overnight at room temperature to reduce autofluorescence. The vials are counted in a scintillation counter on the tritium channel and the cpms from the first and second fractions eluted off the columns are added together.

Figure 7:
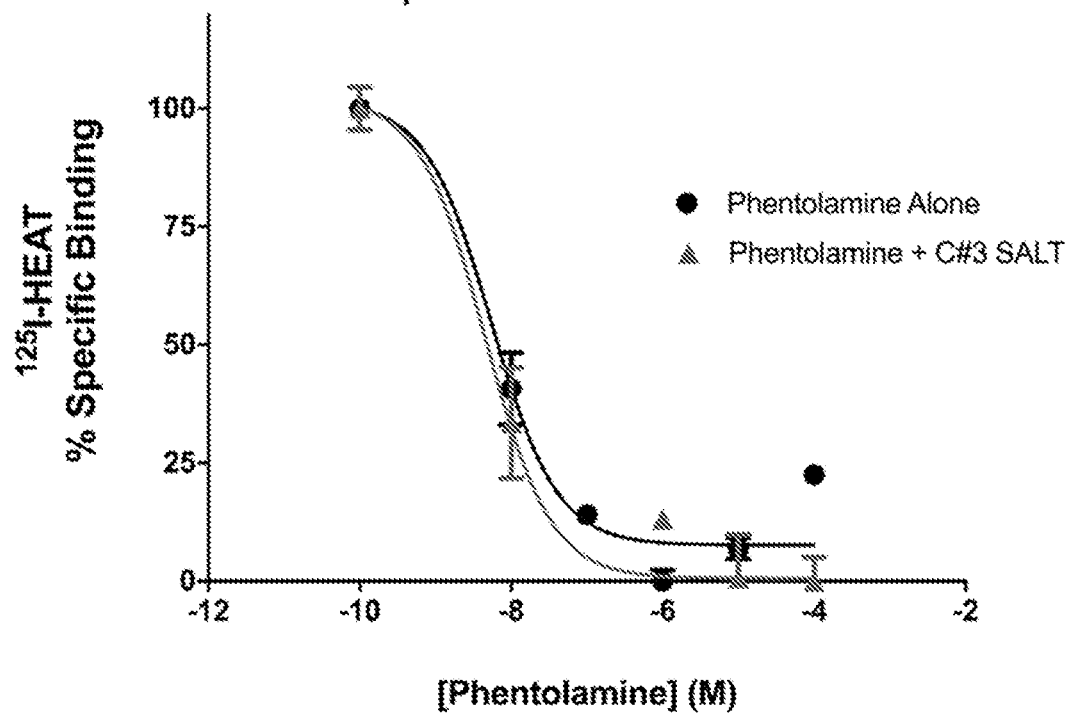
FIG. 7 shows competition binding curve of phentolamine competing off the radiolabel antagonist $^{125}$I-HEAT at the alpha$_{1A}$-AR. Adding Compound 3 at $10^{-5}$M dose does not change the affinity.

Results:

One compound showed a >500 fold difference in selectivity between the subtypes (versus $\alpha_{1B}$, $\alpha_{1D}$). Compound #3 (salt) binds the $\alpha_{1A}$-AR subtype with an approximate affinity of 0.1 uM when 0.5 mM GTP is added to the buffer and cannot fully inhibit the binding of the radiolabeled antagonist, $^{125}$I-HEAT (FIG. 3A). The $\alpha_1$-AR orthosteric antagonist, phentolamine is shown for comparison. The inability of Compound 3 to fully inhibit the radioligand $I^{125}$-HEAT suggested that this compound could be an allosteric modulator. When GTP is removed from the binding buffer, the affinity of Compound 3 indicates there are two sites for binding, typically seen with GPCR agonists, a high affinity site of 0.001 nM and a low affinity site of 100 nM or 0.1 uM (FIG. 3B). The high affinity site is believed to be the allosteric site for Compound 3, while the low affinity site is believed to be the orthosteric binding site. Compound 3 essentially has little, if any, specific binding at the other two subtypes, the $\alpha_{1B}$- and $\alpha_{1D}$-AR (FIG. 4). Compound 3 was tested for the ability to affect the binding affinity of norepinephrine (full agonist), epinephrine (full agonist), and phentolamine (antagonist) at the $\alpha_{1A}$-AR. It was discovered that Compound 3 is a positive allosteric modulator (PAM) with the neurotransmitter norepinephrine (FIG. 5) by apparently increasing the affinity of norepinephrine in a dose-specific manner for the $\alpha_{1A}$-AR. A single dose of Compound 3 can shift the binding curve to the left. There was no effect of Compound 3 at the highest dose tested ($10^{-5}$M) on the binding affinity of epinephrine (FIG. 5). Compound 3 also appears specific to the norepinephrine-bound $\alpha_{1A}$-AR subtype. There is no effect of the highest dose of Compound 3 ($10^{-5}$M) on the affinity of norepinephrine at the $\alpha_{1B}$- or $\alpha_{1D}$-AR subtypes (FIG. 6). There is also no effect of the highest dose of Compound 3 ($10^{-5}$M) on the binding of phentolamine, an $\alpha_1$-AR antagonist (FIG. 7). This demonstrates that there is conformational-selectivity of Compound 3 for only norepinephrine and then only at the $\alpha_{1A}$-AR subtype. The $\alpha_{1A}$-AR adopts a unique conformation when bound to norepinephrine that Compound 3 recognizes and then allosterically alters the shape of the receptor to increase its affinity for norepinephrine. Compound 3 would allow the $\alpha_{1A}$-AR receptor to become activated by norepinephrine and increase neurotransmission when lower amounts of norepinephrine are released at the nerve endings to such as what occurs during neurodegenerative diseases, such as Alzheimer's Disease.

A very common property of allosteric modulators is not only are they are specific for a receptor and ligand, but they can also be signaling-specific. This is also the case for Compound 3. Compound 3 is not an agonist. It cannot stimulate inositol phosphate or cAMP second messengers by itself (FIG. 8A-D, Compound 3 alone). However, Compound 3 is also signaling-specific. Compound 3 in a dose-response can potentiate the cAMP response of norepinephrine by 50% (FIG. 8A) but does not have any effect on inositol phosphate (IP) production of norepinephrine (FIG. 8B). Confirming Compound 3's conformational-selectivity to norepinephrine, there was no effect of Compound 3 on the cAMP (FIG. 8C) or the IP response (FIG. 8D) of epinephrine. Also confirming Compound 3's specificity for the $\alpha_{1A}$-AR subtype only, there was no effect of Compound 3 on norepinephrine's cAMP response on either the $\alpha_{1B}$- or $\alpha_{1D}$-AR subtype (FIG. 9). This confirms that Compound 3 can potentiate the only the cAMP signaling, only with norepinephrine bound to the receptor, and only at the $\alpha_{1A}$-AR subtype. It is thought that the IP response is the main second messenger activated by the $\alpha_1$-AR while the cAMP response is responsible for $\alpha_{1A}$-AR's cognitive effects in the brain (58-63).

Figure 10:
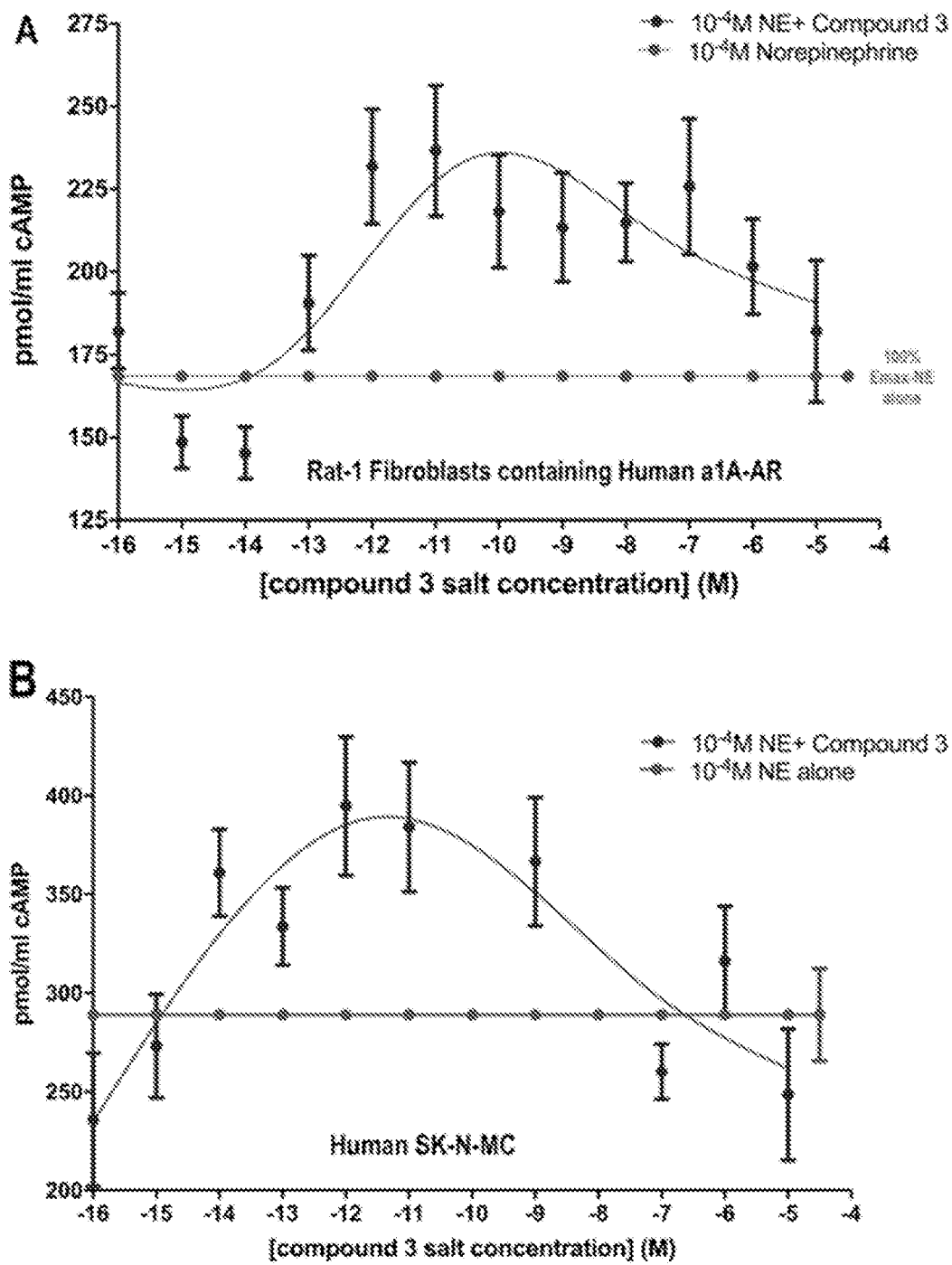
FIGS. 10A-B show data for PAM potentiation of Compound 3 in several different cell lines: from overexpressed rat fibroblasts (A), transformed human neuroblastoma cells (B), and primary adult mouse cardiomyocytes (C).
Figure 10:
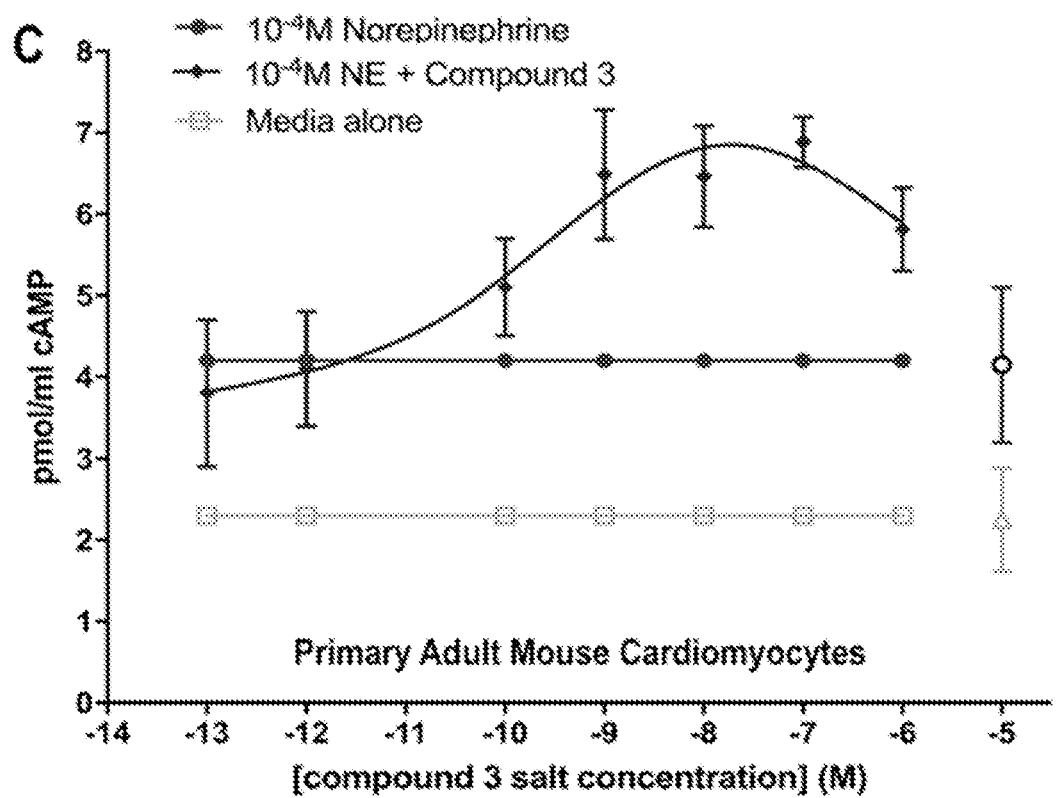

An assay has been developed that shows the dose-dependency, Emax, and potency (EC50) of Compound 3's PAM response to norepinephrine-mediated cAMP potentiation (FIG. 10). In this assay, the concentration of norepinephrine is held constant at its Emax ($10^{-4}$M) (FIG. 10, red line). Compound 3 is then added in a dose-response (FIG. 10, blue line). Any signal above the red line is potentiation. For Compound 3, the Emax ranges from 35-60% of the norepinephrine's maximum response, then the signal stays elevated (i.e. ceiling effect), common with PAMs, then begins to wane when Compound 3 begins to bind to the orthosteric site. The potency of Compound 3 to potentiate norepinephrine's cAMP response ranges from $10^{-13}$-$10^-$ 10M, consistent with the high affinity binding site of Compound 3 (FIG. 3B). The different values for Emax and EC50 depend upon the cell line used and the amount of receptor reserve, where low receptor reserve shift the curve to the right as with primary adult cardiomyocytes (FIG. 10C). The PAM potentiation of Compound 3 is also reproducible is several different cell lines, from overexpressed fibroblasts (FIG. 10A), transformed neuroblastoma cells (FIG. 10B), and primary cardiomyocytes (FIG. 10C) and across species, human $\alpha_{1A}$-ARs (FIG. 10A-B) and mouse $\alpha_{1A}$-AR (FIG. 10C).

The above results are also important because the allosteric properties of Compound 3 would reduce the potential for negative side effects. It is the IP production that leads to the increased blood pressure response via calcium release, resulting in vasoconstriction in the blood vessels that one wants to generally avoid (78-80). Therefore, Compound 3 would potentiate the cognitive-enhancing cAMP signals of norepinephrine but not activate the inositol phosphate-inducing signals to increase blood pressure.

Differences of Compound 3 to Other Compounds

Figure 11:
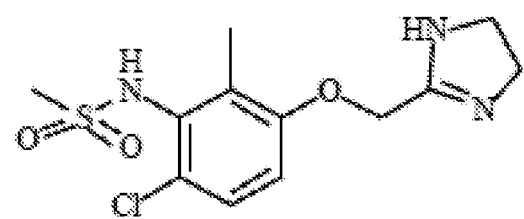
FIG. 11 shows the structure of RO115-1240.
Figure 12:
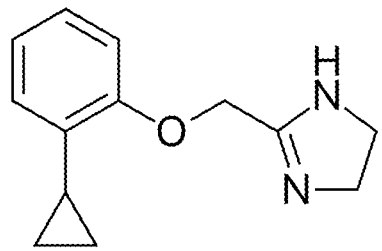
FIG. 12 shows the structure of cirazoline.

Compound RO-115-1240 (FIG. 11) and related compounds have been reported (see, e.g., U.S. Pat. No. 5,952,362). Cirazoline (FIG. 12) is a commercially available $\alpha_{1A}$-AR agonist. Compound 3 has certain unique and superior properties compared to RO115-1240 and cirazoline that cannot be inferred by structural comparison. The below data shows that RO115-1240 behaves very differently than Compound 3 in both binding and signaling, displaying all properties consistent with an antagonist at cAMP to a weak partial agonist (at IP) but with some noncompetitive behavior. There is no evidence of PAM activity at RO115-1240 or cirazoline and no differences in how it interacts with norepinephrine vs. epinephrine.

Figure 13:
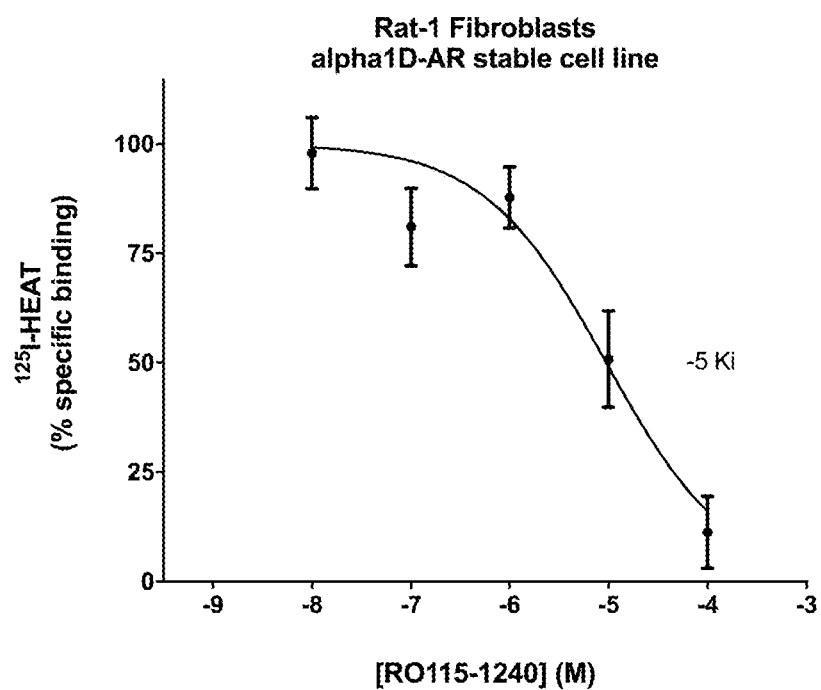
FIGS. 13A-C show competition binding of RO115-1240 with the radiolabel antagonist $^{125}$I-HEAT at the alpha$_{1A}$-AR (A), the alpha$_{1B}$-AR (B), or the alpha$_{1D}$-AR (C).
Figure 14:
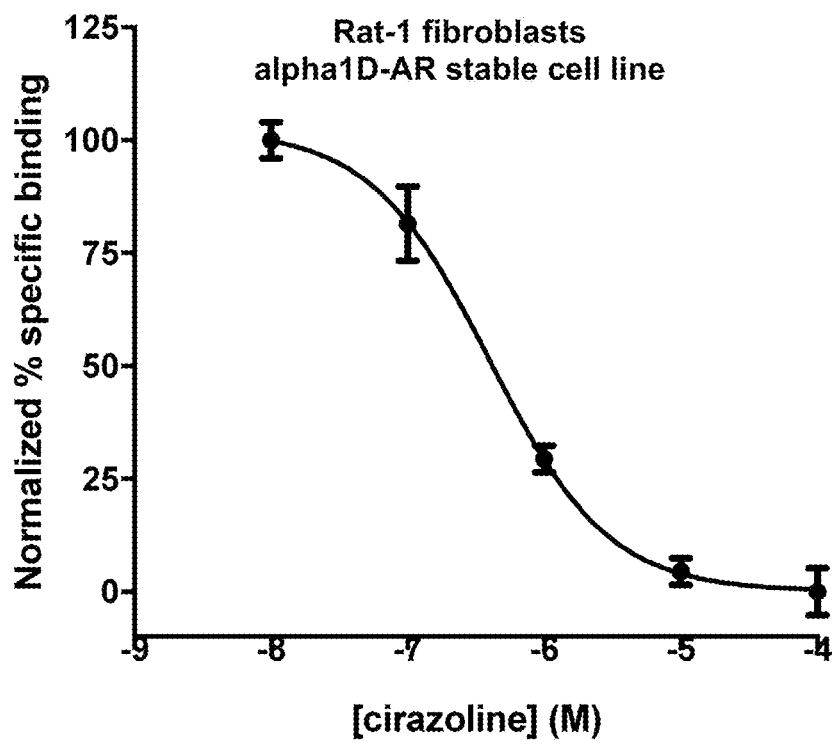
FIGS. 14A-C show competition binding of cirazoline with the radiolabel antagonist $^{125}$I-HEAT at the alpha$_{1A}$-AR (A), the alpha$_{1B}$-AR (B), or the alpha$_{1D}$-AR (C).

RO115-1240 is selective for the $\alpha_{1A}$-AR by 100-fold over the $\alpha_{1B}$-AR or $\alpha_{1D}$-AR subtypes and shows competitive not allosteric behavior (FIG. 13). The Binding data for RO115-1240 is similar to cirazoline (FIG. 14) with cirazoline showing even less selectivity between the $\alpha_1$-AR subtypes.

RO115-1240 displays no difference in the norepinephrine or epinephrine-mediated cAMP response and displays competitive, not PAM behavior (FIG. 15). This would indicate that using RO115-1240 would not be a viable candidate to treat cognitive behavior as it inhibits not potentiates the cAMP response. RO115-1240 lack of specificity for the norepinephrine-bound form of the $\alpha_{1A}$-AR could also cause many negative side effects in the body as RO11-1240's effects would not be targeted to the brain. These signaling results of RO115-1240 are similar to cirazoline which displays no difference in the norepinephrine or epinephrine-mediated cAMP response and displays competitive, not PAM behavior (FIG. 16).

RO115-1240 also displays no difference in the norepinephrine or epinephrine-mediated IP response and displays competitive/noncompetitive partial agonism, not PAM behavior (FIG. 17). RO115-1240 is also an agonist and displays a significant IP response on its own. RO115-1240 would cause significant increase in blood pressure if attempted use in cognitive studies. These signaling results of RO115-1240 are similar to cirazoline which displays no difference in the norepinephrine or epinephrine-mediated IP response and displays competitive/noncompetitive partial agonism, not PAM behavior (FIG. 18). Cirazoline is actually a full agonist at the IP response and could cause significant increases in blood pressure if used in vivo (FIG. 18).

Figure 19:
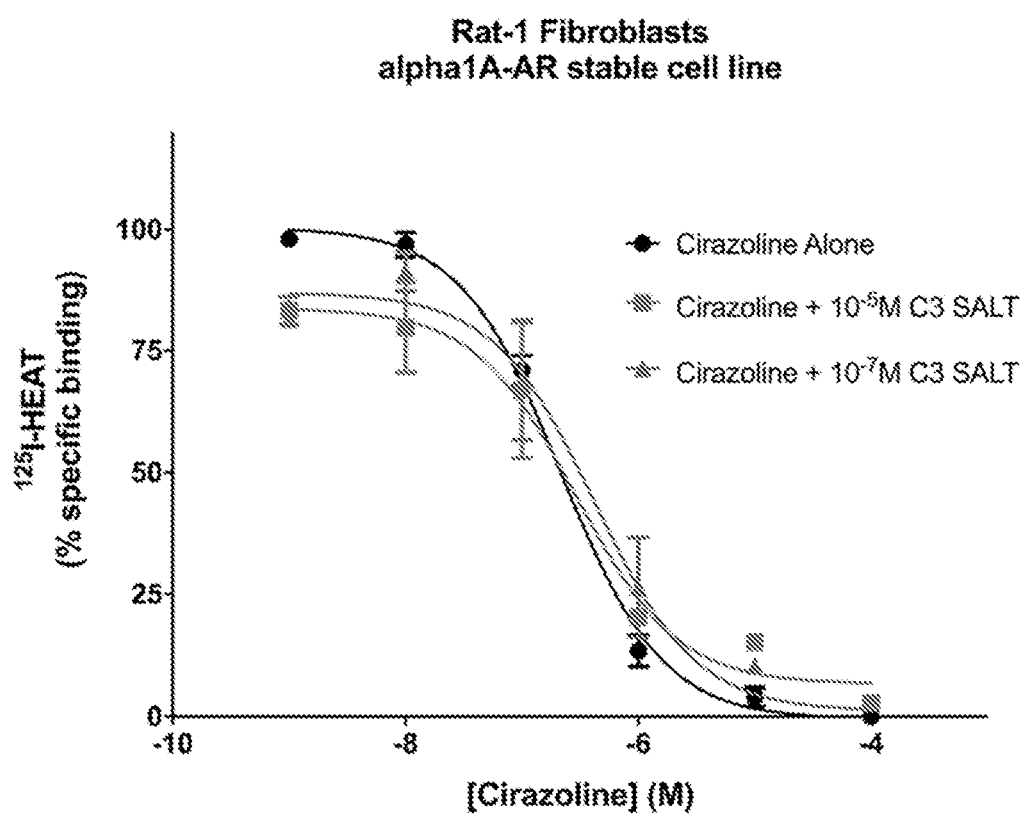
FIG. 19 shows competition binding curves of cirazoline competing off the radiolabel antagonist $^{125}$I-HEAT at the alpha$_{1A}$-AR subtype. There is no effect of Compound 3 at either the $10^{-5}$M or $1^{0-7}$M dose on the binding affinity of cirazoline alone.

In additional studies, it can be shown that Compound 3 does not bind at the same site on the $\alpha_{1A}$-AR as cirazoline, confirming its allosteric binding site that is separate from cirazoline orthosteric binding site. Compound 3 at high doses ($10^{-5}$M and $10^{-7}$M) does not affect the way cirazoline binds to the $\alpha_{1A}$-AR when competing off the radiolabeled antagonist, $^{125}$I-HEAT (FIG. 19). Cirazoline also does not increase the affinity of norepinephrine at the $\alpha_{1A}$-AR but can fully inhibit its binding or that of epinephrine at high doses (FIG. 20). These results demonstrate that cirazoline behaves as a non-competitive inhibitor at the $\alpha_{1A}$-AR at either norepinephrine or epinephrine and is not a PAM.

In summary, there are several major and unique differences in properties of Compound 3 compared to RO115-1240 and cirazoline. Both RO115-1240 and cirazoline are not PAMs but display competitive/noncompetitive partial agonist activity. This could allow RO115-1240 and cirazoline to generate many potential side effects since it can interact with several different receptors and cause signaling on its own. Both RO115-1240 and cirazoline do not show conformational-selectivity to norepinephrine. This property would likely not allow brain-targeting to occur and could increase the likelihood of generating side effects when the drug is circulating in the body. Both RO115-1240 and cirazoline do not show signaling-selectivity towards cAMP which could lead to more side effects such as IP-generated blood pressure increase. Both RO115-1240 and cirazoline show significant IP signaling on their own due to their agonist activity, which could cause an increase in blood pressure at all times when the drug is in the body. This is contrasted to Compound 3 which is only active when norepinephrine is naturally released in the brain and can also potentiate the natural cAMP signaling of norepinephrine.

Other Advantages of Compound 3

There are two types of PAMs currently described (type I & type II) (81-83). Type I PAMs can enhance maximum activity without altering $EC_{50}$ (i.e. effective concentration at 50% of the signal response) while type II PAMs act by shifting the agonist $EC_{50}$ to lower values. There are also mixed type I/II PAMs. Compound 3 is a Type I PAM because it potentiates the NE-mediated cAMP response without changing the $EC_{50}$. It is signaling-selective because it only potentiates the cAMP signal without altering the IP signal. It is ligand-induced conformational selective because Compound 3 only has effect on the norepinephrine-bound receptor and not the epinephrine-bound receptor. All of the commercially available drugs for the $\alpha_{1A}$-AR (including RO115-1240 and cirazoline) have the potential to interact with the $\alpha_{1B}$ or $\alpha_{1D}$-AR and/or crossover to β-AR or $\alpha_2$-ARs. There are also no existing agonists that demonstrate more than 100-fold selectivity over the other $\alpha_1$-AR subtypes, including RO-115-1240 and cirazoline. There are three reports of allosteric modulation at $\alpha_1$-ARs and all are described as negative allosteric modulators (NAMs) (84-86). Compound 3 is the first report of a PAM for the $\alpha_1$-AR.

Another advantage of PAMs is that they are saturating; once the allosteric sites are fully occupied, there is no further observed allosteric effect. In contrast, orthosteric sites where cirazoline and RO-115-1240 bind can be infinite, as it depends only on the relative concentrations of the competing species. So, there is a limit to the potential effects of an PAM and the drug can be given in relatively high doses without fear of overstimulating the system and causing a greater number of side effects.

Another advantage of PAMs relates to their ability to selectively tune responses only in tissues in which the endogenous agonist (norepinephrine or epinephrine) exerts its physiological effects. Normal neurohumoral signaling involves variations in the activity of nerves that release neurotransmitters; a PAM would be expected to exert its effects only when the endogenous agonist is present since it has no basal activity on its own. If nerve activity is reduced, the modulator would have minimal effects and side effects, despite its continued presence in the body. i.e. Compound 3 has no basal activity on its own and can selectively tune into norepinephrine-mediated cAMP signaling. Because norepinephrine is dominantly present in the brain, Compound 3 would be brain-targeted, which is something that either RO-115-1240 or cirazoline cannot do.

Another advantage of PAMs is the potential for greater receptor selectivity. The amino acids that contribute to allosteric binding sites are structurally distinct from those that comprise the orthosteric binding site, which are the also the most conserved regions between receptor subtypes. While a PAM may have low affinity binding at other receptors, the conformational-selectivity is tuned to only the $\alpha_{1A}$-AR subtype. Signaling was not altered in either the $\alpha_{1B}$-AR or $\alpha_{1D}$-AR subtypes because the conformational-selectivity depends upon several residues only found in the $\alpha_{1A}$-AR.

Furthermore, type I PAMs may enhance signaling when receptors are degenerating. This is not possible with orthosteric drugs, which will continuously affect receptor function as long as they are present. If a neuron is degenerating and decreases the number of receptors on its surface, orthosteric drugs such as cirazoline or RO-115-1240 cannot act upon it. Type 1 PAMs can enhance the signaling of the remaining receptors left on a degenerating neuron such as what occurs in Alzheimer's Disease and restore near-normal function.

In Vivo Characterization of Compound 3

A 10 month continuous dose study was performed in the 3×TG Alzheimer's Disease (AD) mouse model containing the triple mutations (APP(swe), PS1(M146V), tau(P301L)) from Jackson labs. Synaptic dysfunction and LTP deficits manifests in an age-related manner beginning from 2-6 months that occurs prior to Aβ pathology (87, herein incorporated by reference). Hippocampal-dependent cognitive impairments begin at 4-6 months depending upon the strain (88-89, herein incorporated by reference). 3×Tg mice have documented cognitive deficits in the Morris water maze (88) and Barnes maze (9, 90). Deficits in long-term synaptic plasticity correlate with the accumulation of intraneuronal Aβ (88). 3×Tg have decreased neurogenesis in both SGZ and SVZ before Aβ pathology and treatments that increased neurogenesis improved memory in 3×TG mice (18-19, herein incorporated by reference).

AD mice were first randomized and sorted into control or treatment groups. There were two treatment groups age and sex-matched and two age and sex-matched control groups which do not receive the drug in the water. 14 AD mice from each treatment group received Compound 3 in the drinking water (2.611 mg/kg/bw) to deliver a daily dose near the peak potentiation of the cAMP response in the brain at $10^{-8}$M based upon the PAM assay and pharmacokinetics. This was achieved by adding Compound 3 to the drinking water at 32 uM, assuming the mice drink 6 ml/day, with only 10% of bioavailable drug reaching the brain. The drug was administered in the drinking water for 10 months, starting at age 2 months, then subjected to either different cognitive behavioral tests or electrophysiology at age 12 months to maximize the manifestations of AD symptoms in these mice. Mice are maintained on the drug for the duration of the studies and blinded to the operator. There was no differences in the death rates between the groups during the course of the studies.

Figure 21:
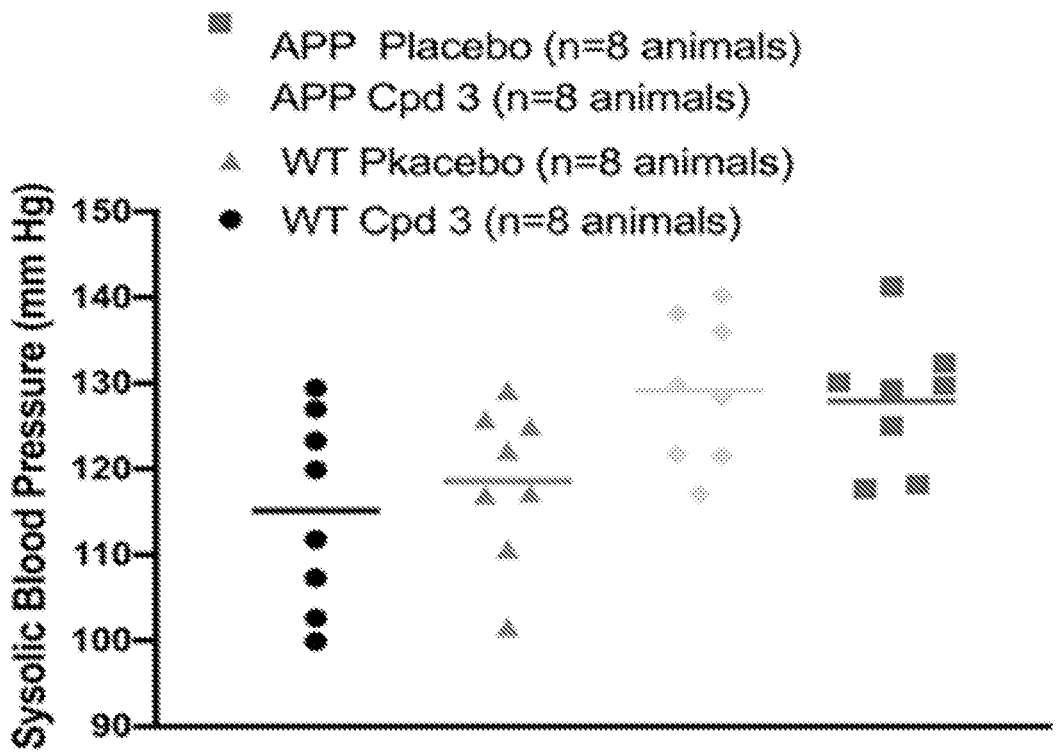
FIGS. 21A-C show Compound 3 does not affect blood pressure in 3×TG mice after 2 months or 6 months of dosing.
Figure 23:
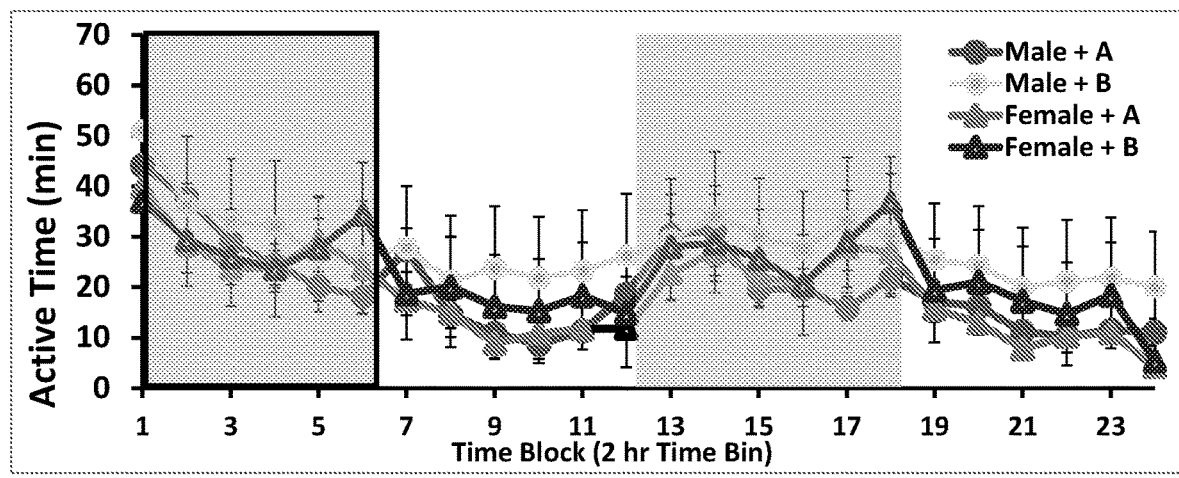
FIG. 23 shows Smart Cage analysis of locomotor activity on Compound 3-treated AD mice (A) and untreated AD control mice (B) as assessed as active time on mice that are free to roam for 48 hours with free access to food and water.
Figure 24:
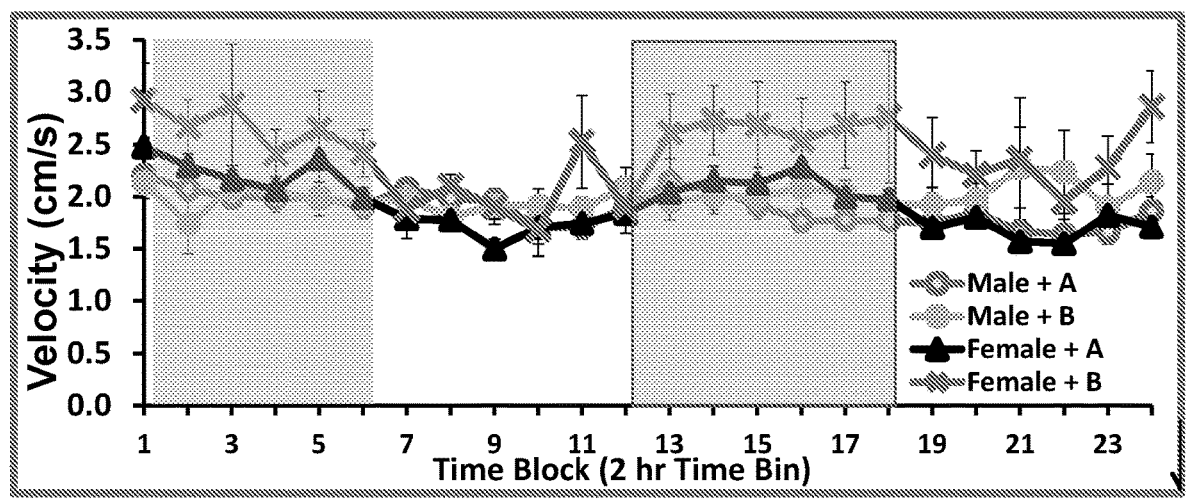
FIG. 24 shows Smart Cage analysis of locomotor activity on Compound 3-treated AD mice (A) and Untreated AD control mice (B) as assessed by velocity on mice that are free to roam for 48 hours with free access to food and water.

The mean arterial blood pressure was measured at 2 months and 7 months of age in the 3×TG mice and found no significant differences between the treated (M: 97±3; F: 85±2.4) vs untreated groups (M: 92±2.5; F: 92±2.6) (N=13-16) as expected (FIG. 21A-B). In another set of studies using the APP (London Mutation) Alzheimer's Disease mouse model and WT controls, mice were given a large daily dose (40 mg/kg/bw), but there was no changes in blood pressure between the Compound 3-treated and placebo groups (FIG. 21C). Compound 3-treated 3×TG female mice have increased body weight compared to untreated mice (FIG. 22). As body weight decreases during late stage Alzheimer's Disease, these results suggest that Compound 3 has reversed this symptom. Before testing, the mice were also subjected to a Smart Cage (automated noninvasive activity monitoring) assessment of locomotion to be sure that Compound 3 did not affect motor ability. Compound 3 (A treatment group) has little effect on locomotion as assessed by the amount of active time (FIG. 23) or as assessed by velocity (FIG. 24). At 12 months of age mice were subjected to long term potentiation (LTP) (FIG. 25). LTP was statistically significant (p<0.01) in female Compound 3-treated AD mouse model (A) compared to untreated AD mice (B). This results suggests that Compound 3 can increase long-term memory during Alzheimer's Disease.

Figure 26:
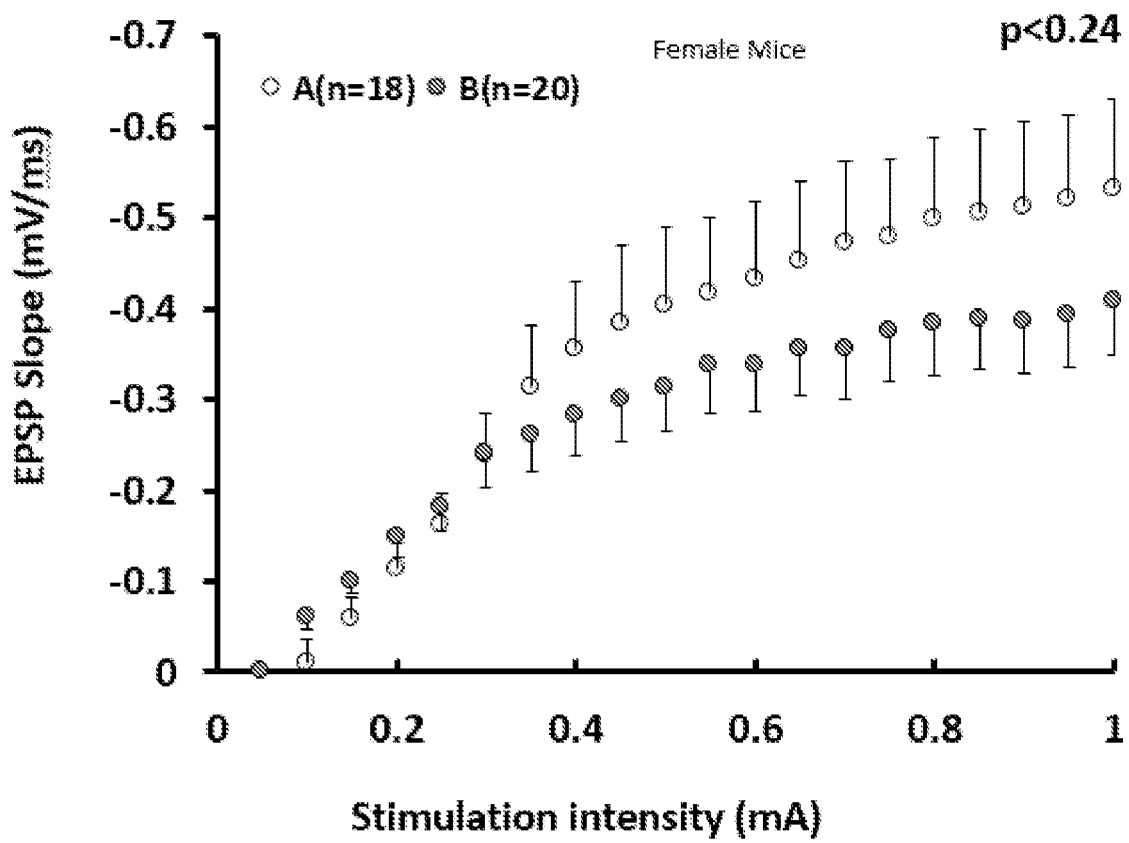
FIG. 26 shows basal synaptic transmission, as determined by the input-output relation between fiber volley amplitude stimulation (x axis) and fEPSP slope (y-axis), is increased in Compound 3-treated female 3×TG mice. The graph shows EPSP amplitudes (mean±SEM) as a function of stimulus intensity in the CA1 (stratum radiatum) hippocampus. Sensitivity to electrical stimulation was similar between treated and untreated mice, while response amplitudes, including the maximal response at 1 mA, were higher (p<0.24) than the untreated group.

Compound 3 can increase synaptic strength (i.e. synaptic plasticity) of the CA1 area of the hippocampus in the 3×TG Alzheimer's Disease Mouse model by increasing the Input/output neurotransmission (FIG. 26). While the data is only approaching significance, it is thought that increasing the number of mice would render this test statistically significant. The input-output curve is usually a measure of the efficacy of transmitter release illustrating how the output of a circuit changes relative to the input. A stronger synapse will give a bigger output with the same input compared to a weaker synapse. It is generally accepted that changes in synaptic strength contribute to learning and memory.

While these results are still not statistically significant, the results suggest that increasing the number of mice would allow statistical significance and indicates that Compound 3 treatment can increase synaptic plasticity, a measure of increased learning and memory functions in Alzheimer's Disease.

Figure 27:
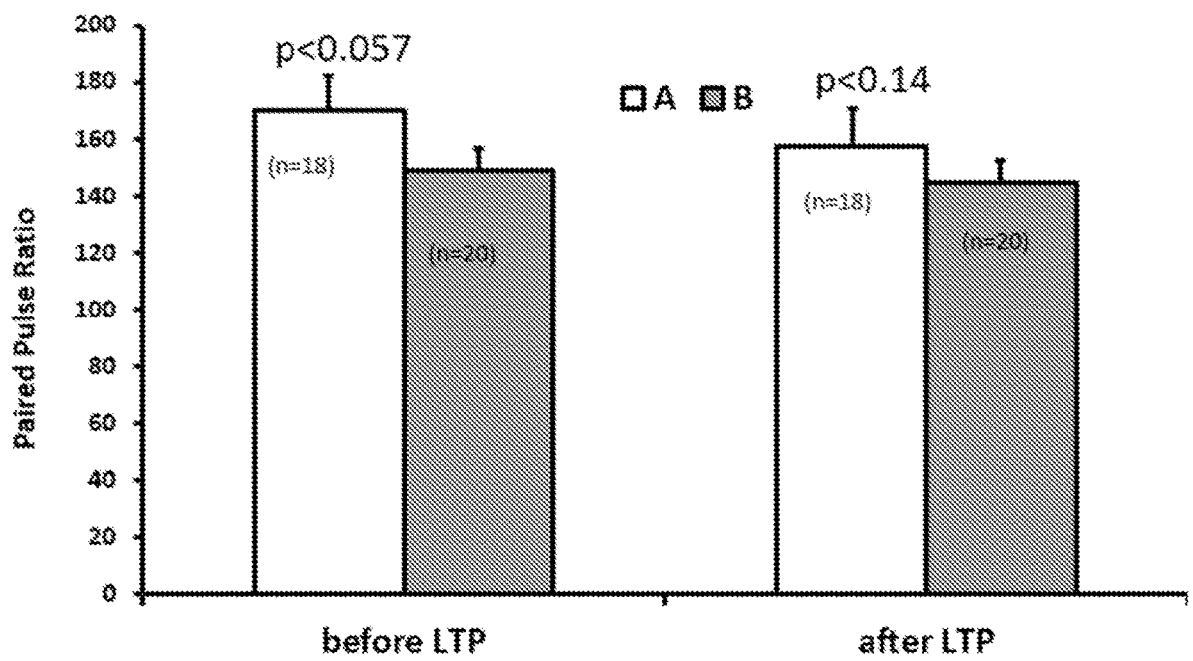
FIG. 27 shows paired-pulse ratio of evoked field potentials before and after high frequency stimulation (i.e. LTP) in female 3×TG Alzheimer's Disease mouse model. The graph shows the ratios of the second and first field potential amplitudes evoked by paired-pulse stimulation with 50 ms intervals for all groups. Values were obtained before and after the induction of long-term potentiation by HFS. All data are expressed as mean±standard error of the mean (S.E.M.).
Figure 28:
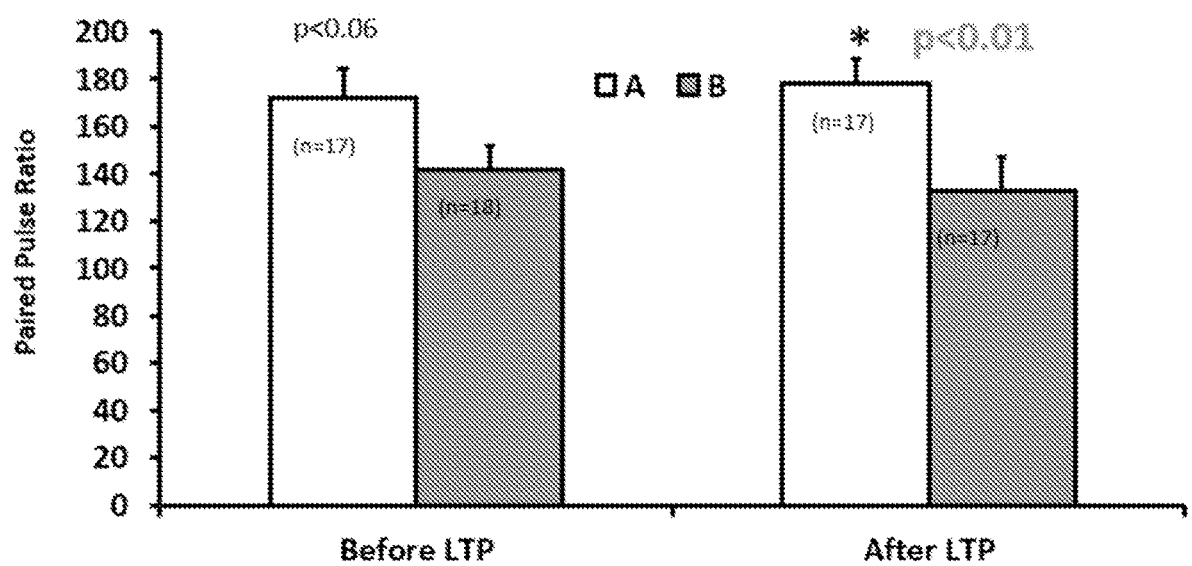
FIG. 28 shows paired-pulse ratio of evoked field potentials before and after high frequency stimulation (i.e. LTP) in male 3×TG Alzheimer's Disease mouse model. The graph shows the ratios of the second and first field potential amplitudes evoked by paired-pulse stimulation with 50 ms intervals for all groups. Values were obtained before and after the induction of long-term potentiation by HFS. All data are expressed as mean±standard error of the mean (S.E.M.).

Paired Pulse Ratio (PPR) is higher for Compound 3-treated Alzheimer's Disease (AD) 3×TG female mice (A) compared to untreated AD 3×TG female mice (B) (FIG. 27). Compound 3 also increased PPR in Compound 3-treated Alzheimer's Disease (AD) 3×Tg male mice (A) compared to untreated AD 3×TG mice (B) (FIG. 28).

Paired Pulse Facilitation (PPF) is a measure of short-term plasticity and allows neurons to generate appropriate output in response to acute changes in synaptic activity and facilitates learning and memory. It is a phenomenon in which postsynaptic potentials evoked by an impulse are increased when that impulse closely follows a prior impulse. The mechanisms underlying neural facilitation are exclusively pre-synaptic. PPF arises due to increased presynaptic $Ca^{2+}$ concentration leading to a greater release of neurotransmitter-containing synaptic vesicles. Neural facilitation may be involved in several neuronal tasks, including simple learning and information processing and considered a measure of synaptic plasticity/strength. Paired-pulse ratio (PPR), amplitude of the second response divided by that of the first response, depends on the probability of vesicular release at the synapse. As the PPR does not change after LTP, the mechanism of the synaptic plasticity is thought to be post-synaptic and not based upon enhanced neurotransmitter release. This would be consistent with an $\alpha_1$-AR mediated mechanism which are post-synaptic in nature. These results suggest that Compound 3 can increase short-term synaptic plasticity which may strengthen learning and memory functions.

Figure 29:
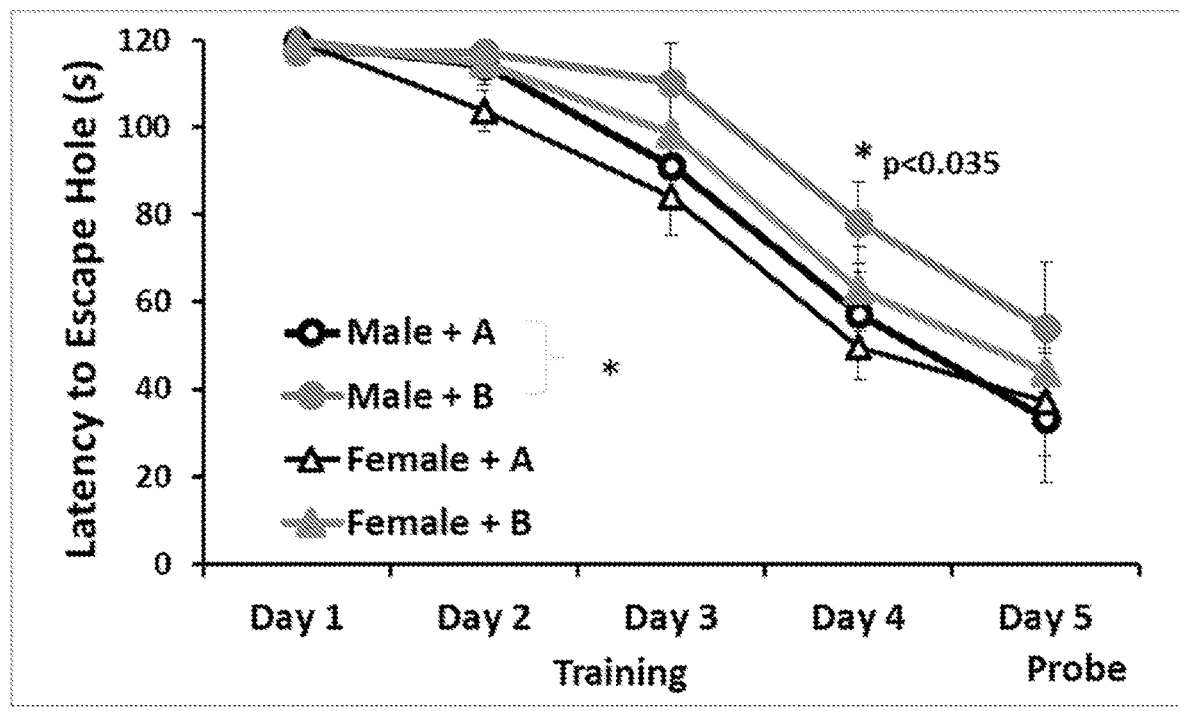
FIG. 29 shows latency to escape time (learning curve) during the 5 day training sessions for Compound 3-treated Alzheimer's Disease (AD) 3×TG mice (A) and untreated (B) AD mice in the shortened Barnes Maze test (spatial reference memory).
Figure 30:
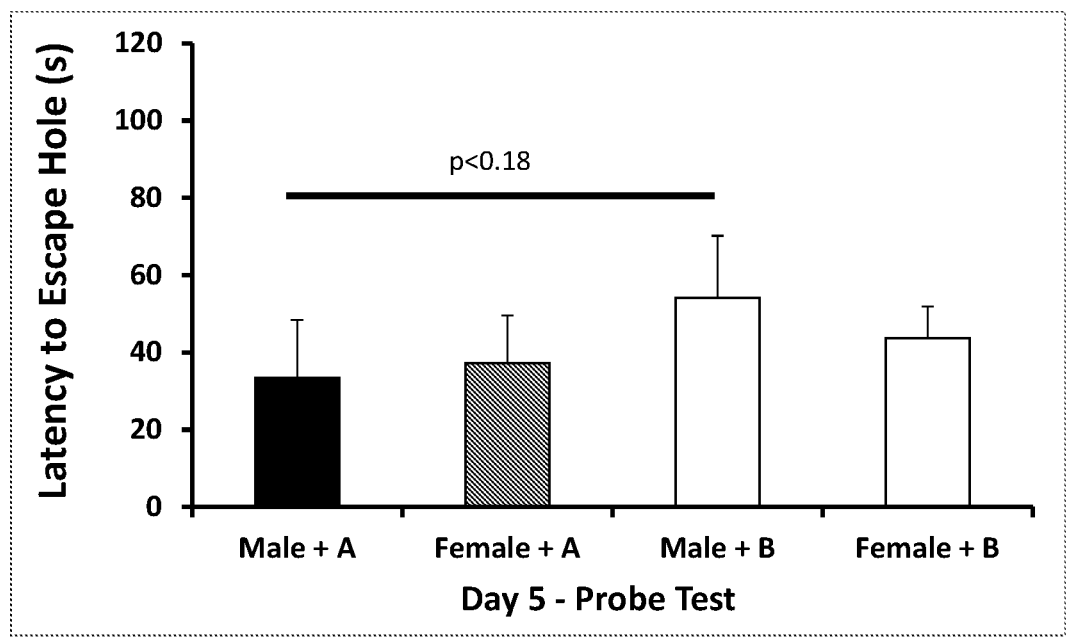
FIG. 30 shows latency to escape time during the day 5 short term memory probe test for Compound 3-treated (A) and untreated (B) AD mice in the shortened Barnes Maze test (spatial reference memory). Data approached significance and may reach significance if more mice are used.
Figure 31:
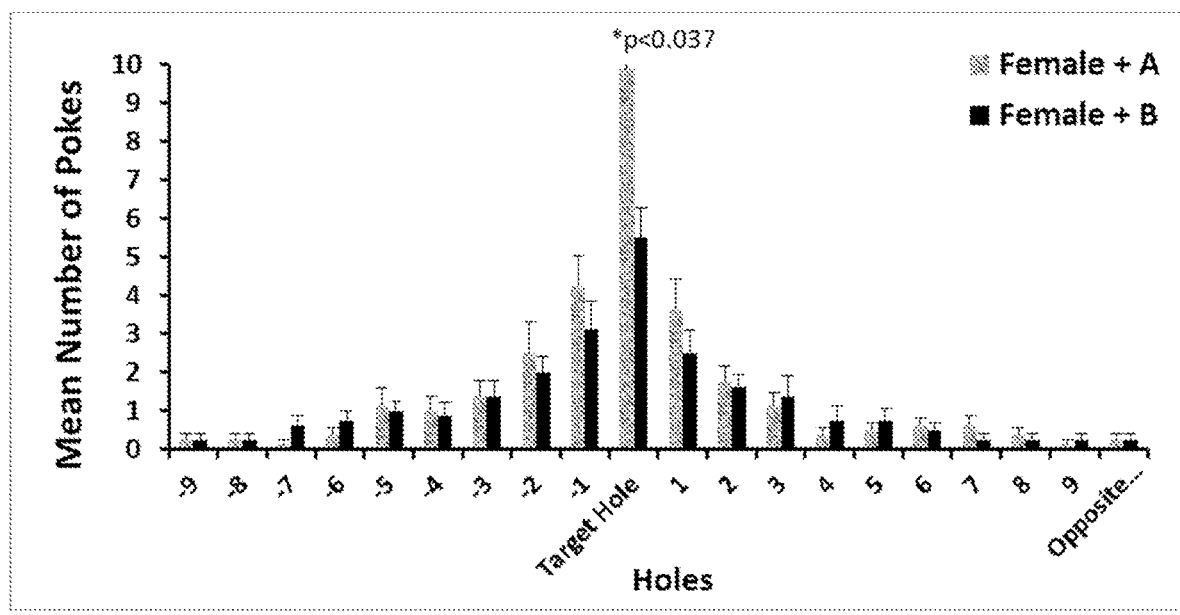
FIG. 31 shows the number of hole pokes for female mice during day 5 memory probe test of the shortened Barnes Maze for Compound 3-treated AD 3×TG (A) and untreated AD 3×TG (B) female mice. Good performance is the number of correct hole pokes at and near the target hole.

Compound 3 treatment can significantly decrease the latency to the escape hole for Alzheimer's Disease (AD) male mice compared to untreated control AD mice during the training period of the shortened Barnes Maze cognitive test (FIG. 29). Compound 3-treated AD mice (A) decreased the time to find the escape hole during day 5 of the memory test of the shortened Barnes Maze (FIG. 30). Compound 3 can increase the ability of female AD mice to find the correct escape hole as measured through the number of head pokes into each hole (FIG. 31). All these results from the Barnes Maze cognitive tests indicate that Compound 3 may increase spatial reference memory in Alzheimer's Disease.

Figure 32:
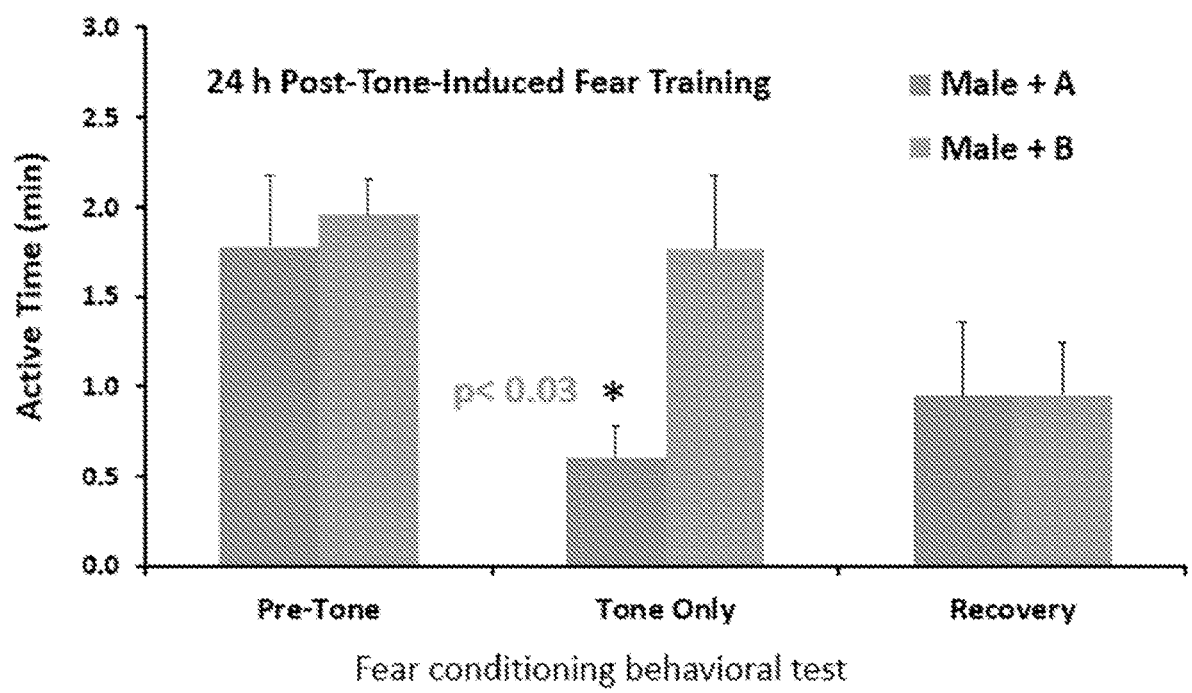
FIG. 32 shows amount of active time for male mice after Tone-Induced Fear Conditioning (Tone & Foot-shock) during the Pre-Tone, Tone Only and Recovery Periods for Compound 3-treated AD 3×TG (A) and Untreated (B) AD mice.
Figure 33:
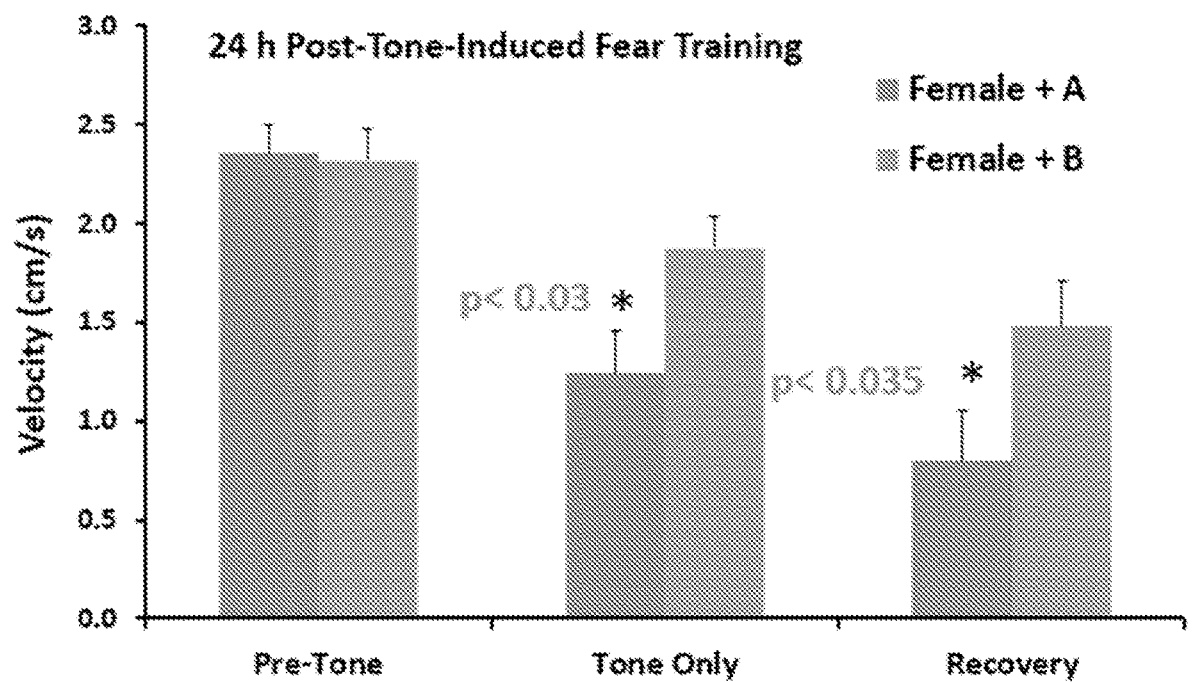
FIG. 33 shows velocity of distance traveled for Female mice after Tone-Induced Fear Conditioning (Tone & Foot-shock) during the Pre-Tone, Tone Only and Recovery Periods for treated (A) and Untreated (B) AD mice.

Compound 3-treated AD male mice (A) remember the foot-shock associated with the tone and freeze (i.e. less active time) compared to untreated control AD male mice (B) during a fear-conditioning behavioral test (FIG. 32). Compound 3-treated AD male female mice (A) also remember the foot-shock associated with the tone and freeze (i.e. slower movement speed) compared to untreated control AD female mice (B) during the fear-conditioning behavioral test (FIG. 33). These results suggest that Compound 3 may increase associative learning tasks during Alzheimer's Disease.

Figure 34:
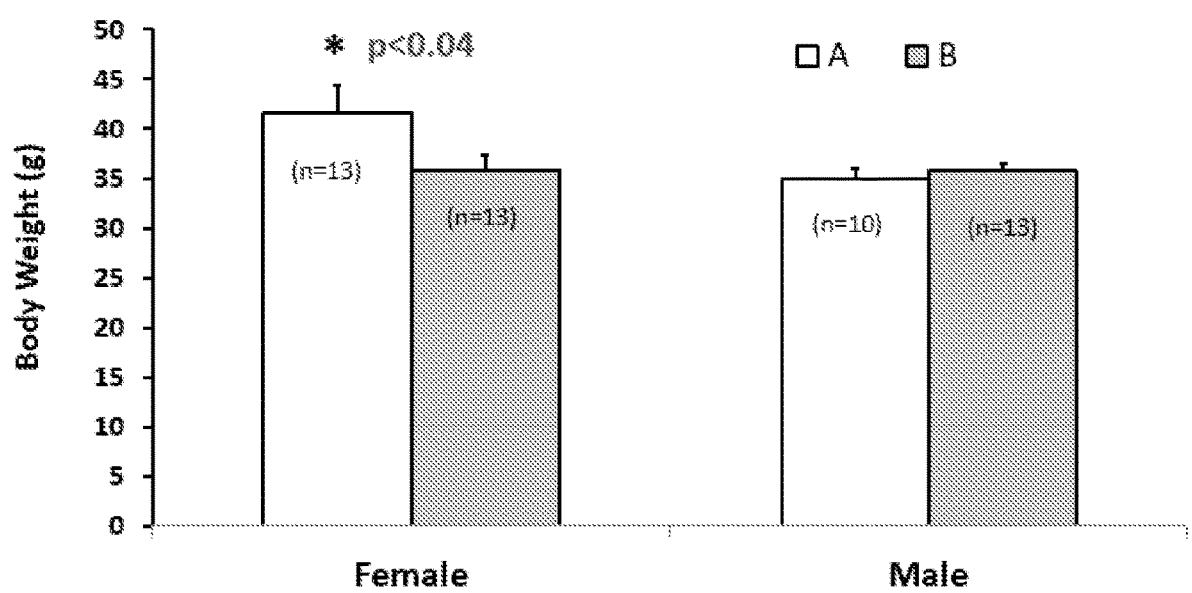
FIG. 34 shows end body weight of Compound 3-treated AD mice (A) and Untreated AD control mice (B) before the mice are sacrificed.

Compound 3-treated female AD mice (A) retained or gained body weight while other groups lost weight (FIG. 34). It is known that females in the 3×TG AD mouse model have higher penetrance for the disease than males so an increase in body weight may be a general sign of better health. Weight loss and muscle loss are well-known symptoms associated with AD (91-93). This result suggests that Compound 3 may be improving general health in Alzheimer's Disease.

Example 4

Screening Compounds

This Example describes how a given candidate compound of Formula I could be screened to determine if it selectively increases activation of $\alpha_{1A}$-AR in vitro (e.g., is a positive allosteric modulator (PAM) of $\alpha_{1A}$-AR), as well as further screening of such identified candidate compounds for their ability to cross the blood brain barrier, and retain activity in vivo, without causing increased blood pressure. Examples of such candidate compounds in Formulas I are those that are similar to Compound 3, but have one or more functional groups changed.

A. In Vitro Selective $\alpha_{1A}$-AR Activation Screening

The candidate compounds within Formula I are assessed by radioligand binding to determine affinity and PAM properties using AR-null cell lines stably transfected with cDNAs expressing individual AR subtypes. Candidate compounds are assessed for inositol phosphate and cAMP signaling properties in the presence or absence of norepinephrine or epinephrine.

Characterization: Binding affinity. Using AR null stably-transfected cell lines that each express only one of the three individual $\alpha_1$-AR subtypes, compounds are characterized for their selectivity for the $\alpha_{1A}$-AR in radioligand binding studies. To be sure of no cross-reactivity, binding affinity against the $\alpha_2$-ARs and $\beta$-ARs are also measured. Details for such procedures are found generally at references 25-26, 94-98, all of which are herein incorporated by reference. It has verified, through radioligand binding studies, that Compound 3 does not interact with high affinity with $\alpha_2$-ARs. Therefore, it is preferred that candidate compounds do not interact with $\alpha_2$-ARs.

Methods: Briefly, membranes are prepared as described previously (99) from stably transfected cell lines and competition reactions contain the non-selective $\alpha_1$-AR radiolabel [$^{125}$I]-HEAT (2-{[β-(4-Hydroxyphenyl)ethyl]aminomethyl}-1-tetralone hydrochloride) with increasing amounts of unlabeled ligand. Nonspecific binding is determined in the presence of phentolamine (100 uM). The binding buffer contains 20 mM HEPES, pH7.4, 1.4 mM EGTA, 12.5 mM MgCl$_2$, and pH to 7.4 using 1M NaOH. To convert all the conformations to a single low-affinity site, 0.5 mMGTP is added to the binding buffer. When the GTP is removed, both high and low affinity sites are observed (typical of GPCR agonists). Reactions are stopped after 1-2 h by the addition of cold buffer and filtered with a cell harvester. Binding data is analyzed using Graphpad Prism. Statistical testing is performed using an ANOVA and Student-Newman-Keuls multiple comparison test to determine significant differences ($p<0.05$).

Characterization: Using stable transfected cell lines that each express only one of the three individual $\alpha_1$-AR subtypes, one can characterize the candidate compounds in a dose response for their potency and intrinsic activity using functional inositol phosphate and cAMP assays with or without norepinephrine. For cAMP assays, cells are pre-incubated for 45 mins-1 hour with 10 uM propranolol, followed by 30 mins of pre-incubation with 100 uM IBMX, then norepinephrine or epinephrine and the test compound for 30 mins at 25C to optimize signal. For inositol phosphate assays, cells are co-incubated with $^3$H-inositol, compound and norepinephrine or epinephrine in the presence of 10 uM LiCl for 30 mins at 25C. Further general guidance can be found in references 25-26, 94-98, and 100-108, all of which are herein incorporated by reference.

General Properties of Identified Candidate Compounds: As cirazoline is already about 30-50 fold selective for the $\alpha_{1A}$-AR, and Compound 3 appears to be allosterically selective for the $\alpha_{1A}$-AR, one would generally expected similar or enhanced allosteric selectivity with identified candidate compounds. In certain embodiments, the identified candidate compound would be a compound that improved the PAM effect by increasing the affinity of norepinephrine by more than 5-fold or to show enhanced cAMP effect, increased BBB penetration, or increased stability in vivo.

B. Blood-Brain Barrier Screening

Identified candidate compounds can be assessed for blood brain barrier (BBB), pharmacokinetics, and verified target engagement.

BBB measurement: In Vitro: Identified candidate compounds can be screening through the human BBB kit from Neuromics (Cat #3D45002-12) according to manufacturer's instructions, or with a similar kit. This Neuromics kit mimics transport properties of the human BBB due to the formation of tight junctions, higher expression of specific carriers, or greater cell viability. This kit cultures brain endothelial cells with pericytes and astrocytes layered in an insert, resulting in improved endothelial cell polarization, enhanced formation of tight junctions, and better endothelial cell-to-cell contact. These conditions are important for barrier development and prevent the dilution of secreted neurotrophic factors.

Pharmacokinetics: Mice are dosed for each identified candidate compound via oral gavage and accessed for a three-arm PK study in C57BL/6 mice at 0, 15 min, 30 min, 1 hr, 3 hr, 6 hr, 12 hr, 24 hr, and 48 hrs. Three groups of 12 mice (N=3 per time point) are administered a PO dose of the identified compound of interest and following completion of the PK study, terminal blood plasma samples and brain tissue samples are collected at the time points to determine in vivo BBB penetrance. Parameters tested can include absorption, bioavailability, volume distribution, metabolism, Cmax, tmax, concentration, elimination rate and half-life, and clearance. Pharmacokinetics data for Compound 3 is shown in FIG. 35.

Verified Target Engagement In Vitro & In Vivo: The next step would be to repeat studies in membranes isolated from a WT mouse brain, ex vivo. In Vivo: Radioligand-displacement assays can also measure target engagement in animal models in vivo. These assays involve pre-treatment of rodents with a dose-range of drug followed by a radiolabeled tracer ligand ($I^{125}$-HEAT) that also binds to the target protein and then measurement of the radiotracer in the brain versus kidney. Dose-dependent reduction in radiotracer signal can be used to calculate target engagement. However, with $\alpha_1$-ARs in such low abundance, radiolabels are not easily measured in vivo. BODIPY: For a better in vivo target engagement, one can use BODIPY-prazosin. QAPB (quinazoline piperidine BODIPY) or BODIPY-prazosin (109-110) has been used to label native tissues expressing $\alpha_1$-ARs and could be used. This particular form of BODIPY is excited at 488 nm and emits above 515 nm. Their better utility is due to their high thermal and photochemical stability, chemical robustness, and tunable fluorescence properties. It fluoresces only when bound and not when free in solution. This allows us to study binding in live cells in real time and at equilibrium between the free ligand and that bound to the cell. This gives an advantage over conventional ligand binding, which employs 'post-wash' measurement of bound ligand because this means that the cells or tissues are exposed to ligand to allow binding but then have to be washed to remove unbound ligand. Post-washing is necessary with radioligands and with compounds that are fluorescent in solution because they would give too much background counts, swamping the bound ligand's measurement. With BODIPY, extracellular non-fluorescent compound is not detected so one can carry out measurements in real time and at equilibrium. Prazosin is non-selective but is very hydrophobic so it crosses the BBB very readily. BODIPY-based probes have been used in binding and imaging β-amyloid plaques in the brain (111) and can clearly visualize the plaque. Uptake into the brain occurs within 2 minutes post-injection. Sections of the brain are then prepared and visualized under fluorescent microscopy.

Ex Vivo Competition Binding Studies: A solution of BODIPY-prazosin (1 uM) to fully occupy all the $\alpha_1$-AR sites is injected intravenously directly into the tail of mice. This is followed by injecting increasing concentrations of the drug, using one concentration per mouse. The mice are sacrificed at 60 min postinjection. The brain is removed, fixed in 4% paraformaldehyde, embedded in agarose, and sectioned using a vibratome as has been previously described in $\alpha_{1A}$-AR brain localization studies (25, herein incorporated by reference in its entirety, and specifically for this assay). Fluorescence images of brains are acquired using a confocal microscope (excitation, 488 nm; emission, 515 nm). Memory centers such as the hippocampus, amygdala, prefrontal cortex are scanned at low magnification. The fluorescence intensity in each region of interest is assessed and compared with varying doses of the compound using image J software.

In Vivo Target Engagement: These assays involve a pre-treatment of rodents with a saturating dose of the BODIPY-prazosin, followed by increased doses of Compound 3 in a series of mice. Dose-dependent reduction in the fluorescent signal can be used to verify target engagement on an organ-dependent level. Prazosin is very hydrophobic so it crosses the blood brain barrier very readily. Uptake into the brain occurs within 2 minutes post-injection. Mice are first kept for 2 weeks on a special low-auto fluorescent chow diet available at researchdiets.com as many plant-based foods have chlorophyll and other fluorescent components. As a control for chow-related fluorescence, untreated mice with no BODIPY-prazosin are also imaged. BODIPY-prazosin is suspended in a mixture of DMSO/$H_2O$ (50:50, v/v). Animals are first dosed approximately at the 10 times the calculated Ki of prazosin (1 nM), using the blood volume of a mouse (58.5 ml of blood per kg of bw) (approx. 22 mg kg$^{-1}$ bw). After a quick scan as detailed below using larger sections to determine the equilibrium time for BODIPY-prazosin binding, a new set of mice injected with BODIPY-prazosin but now also with a saturating dose of Compound 3 ($10^{-5}$M) is added and mice are imaged at the Compound 3 $C_{Max}$ time point (as determined by PK-approx. 3 hr). PBS treated mice were used as negative controls.

Imaging acquisitions: Mice are sacrificed by isoflurane overdose and then flash frozen in OCT freezing medium by liquid nitrogen immersion. The frozen block is alternatively sectioned using a cryomicrotome and imaged in a tiled fashion every 50-μm yielding very large, high resolution data volumes. The entire mouse is sectioned and optically imaged every using a cryo-fluorescence imager (CryoViz™; Bioinvision, Inc., Cleveland, OH). Block-face images are collected with an in-plane resolution of 10.5×10.5 μm². Brightfield and fluorescent images are acquired, stitched together and visualized using proprietary software (Bioinvision, Inc). The excitation filter is 588 nm emission and 617 nm long pass is used to detect BODIPY® TR-X. Each spectral image set are acquired using a 10 s exposure. Mean intensities of the signal at each organ and background are computed and averaged for each image.

C. In Vivo Activity Screening

One can assess identified candidate compounds with desired properties to improve cognition, synaptic plasticity, LTP, hippocampal neurogenesis, and to decrease pathology in the triple mutation (3×Tg) AD mouse model. Such compounds may be screened to identify those that are able to, for example, improve cognition and neurological functions in the AD mouse model while decreasing pathology.

Alzheimer Disease animal model: One can utilize age-matched triple transgenic (3×Tg) mice (APP(swe), PS1 (M146V), tau(P301L)) available from Jackson labs. Male mice have been shown to have greater memory deficits than females in this AD model from ages 2-15 months (112, herein incorporated by reference). Synaptic dysfunction and LTP deficits manifests in an age-related manner beginning from 2-6 months that occurs prior to Aβ pathology (87, herein incorporated by reference). Hippocampal-dependent cognitive impairments begin at 4-6 months depending upon the strain (88-89, herein incorporated by reference). 3×Tg mice have documented cognitive deficits in the Morris water maze (88) and Barnes maze (9, 90). Deficits in long-term synaptic plasticity correlate with the accumulation of intraneuronal Aβ (88). 3×Tg have decreased neurogenesis in both SGZ and SVZ before Aβ pathology and treatments that increased neurogenesis improved memory in 3×TG mice (18-19, herein incorporated by reference). In addition, several other AD mouse models or aged mice can be utilized for in vivo screening as reviewed in (113).

Power Analysis: A Power Analysis can be performed on the results. Power analysis for a two-sided P value of 0.01 and a 50% effect over control requires 14 mice per group for a 95% confidence level. While males have memory deficits that are stronger than females in the 3×TG model (87), both sexes can be included, but in separate treatment groups.

Treatment: AD mice are first randomized and sorted into control or treatment groups. There are two treatment groups based upon sex (male only, female only) and age-matched, then two age and sex-matched control groups which do not receive the drug in the water. 14 AD mice from each treatment group receive the identified candidate compound in the drinking water at dose near its maximum PAM effect determined by pharmacological analysis above. Drinking volumes in mice have been previously analyzed to derive concentration values to use (21, herein incorporated by reference). Untreated AD mice controls are grouped and followed along the same schedule as treatment groups. Compound are administered in the drinking water for anywhere from 2 weeks to 10 months, then the mice are weighed, cognition assessed with different behavioral tests, followed by blood pressure analysis, then sacrificed for pathology and electrophysiology testing. Mice are maintained on the drug for the duration of the studies.

Behavioral/Cognitive Testing. Animals are acclimated. Testing equipment is cleaned between trials. All testing is video-captured, and analyzed blind to mouse treatment. The test is also taken the same time each day.

Barnes Maze. The Barnes maze is used to assess spatial learning and memory and consists of a white, flat, circular platform elevated above ground with 40 holes, under which one escape box is located. Three visual cues are placed surrounding the maze and their locations in relation to the escape box and remain constant. Two floodlights and four fans above the maze provide aversion. The first 4 days consist of learning trials. At the start of each trial, a mouse is placed in the center of the maze under a holding chamber for 30 seconds. When the chamber is lifted, the mouse is allowed up to 300 seconds to enter the escape box. If a mouse failed to enter after the allowed time, it was gently placed into the hole containing the escape box for 30 s. Memory trials are conducted on days 1, 4, 5, and 8 after the 4 days of training. The procedure for the memory trials is the same as learning, except the mice are allowed only one attempt to solve the maze each day. Data includes the time to solve, number of errors made, and distance traveled. Errors are defined as when a mouse poked more than three-quarters of its head into any hole other than the appropriate escape hole. Distance traveled is measured using ANY-MAZE software.

Multi-T Maze. The multi-T maze (60×60×16 cm) is a test of spatial working memory. Visual cues are placed along the correct path of the maze, which leads to a peanut butter reward and an escape box. Mice are trained on 4 consecutive days with the incorrect paths blocked, allowing access only to the correct solution. To test memory, the mice are retested on days 1-8 after training. Data includes time required to solve the maze and the number of errors made. Each time the mouse turned down the wrong path is an error.

Object Recognition: Spatial and non-spatial test version: In this task a rodent is placed in a circular open-field filled with different objects for 6 minutes. After a series of trials, at which point the animal has habituated to the configuration and properties of the different objects, some of the objects are switched from one location to another (spatial recognition); subsequently some of the objects are replaced for new ones (novel object recognition). The time spent exploring the open field (movement/inactivity) as well as number of times and length of time inspecting the objects over the different trials is calculated.

Morris Water Maze: The rodent is placed in a pool of water where it must use and remember visual cues located in the room to find a platform hidden underneath the surface of the water. The task is carried out across days to determine learning. Distance swam, latency to reach the platform, and swim speed are common measures of this test using a video tracking system. The capacity of the animal to retrieve and retain information learned or flexibility to purge and re-learn new strategies can be determined using a probe trial & reversal trial. In the probe trial the platform is taken out and the animals are allowed to swim in the pool. Time spent in the region that previously contained the platform, crossings over the platform area, and time to reach platform location or measured. The reversal trial is identical to the training trials but in this case the platform is switched to the opposite region of the pool, thus the animal has to have the cognitive flexibility necessary to re-learn the new location. A cued version of this task can also be used to measure none spatial strategies as well as visual acuity by rendering the platform visible.

Neurological functions-rationale and approach: As cognition tests are behavioral studies, one should seek to verify that actual neurological and biochemical functions have been modified and are responsible for the cognitive changes. CAM $\alpha_{1A}$-AR mice displayed increased basal synaptic function, paired-pulse facilitation, and LTP (24, herein incorporated by reference) and adult SGZ/SVZ neurogenesis (25, herein incorporated by reference) and it is expected that any compound that activates the $\alpha_{1A}$-AR in the brain will improve these functions in the AD mouse model. The same treated and control mice after behavioral testing may be used in the following further experiments.

In Vivo BrdU Incorporation. Mice are injected with BrdU at 150 mg/kg/bw. Two hours later, the mice are anesthetized, cardiac-perfused, and brains sectioned (25, herein incorporated by reference). Sections are incubated with anti-BrdU and then anti-mouse IgG with fluorescent labels. Samples are scanned using confocal microscopy and BrdU nuclei counted using stereology.

Electrophysiology. Hippocampi are removed and slices cut 400 µm thick and immediately transferred to an oxygenated holding chamber filled with artificial cerebrospinal fluid, acclimated and transferred to recording chambers. Micropipettes are backfilled with NaCl solution and placed in the stratum radiatum. Evoked field excitatory postsynaptic potentials (fEPSPs) are measured in current clamp mode. An ISO-flex stimulator paired with a 7.5-cm bipolar tungsten-stimulating electrode is used for presynaptic stimulation of the Schaffer collateral-commissural fibers. Signals are converted from analog to digital and electronic cycling and noise filtered. Basal synaptic transmission is assessed by determining input-output curves, generated by applying a stepwise 5 µA increase in stimulation intensity. Responses are elicited every 20 seconds with duration of 100 µs per pulse. Short-term plasticity is investigated by assessing paired-pulse facilitation (PPF) by applying two pulses with interpulse intervals of 35-300 ms. A baseline response of 30 min is recorded immediately after PPF, which is followed by θ-burst stimulation (TBS) given at 80% maximal response to induce LTP. fEPSPs are recorded at 50% maximal response every 20 seconds for 90 minutes.

Pathology: The 3×Tg-AD mice develop extracellular Aβ deposits prior to tangle formation. To determine whether APP was processed to liberate the Aβ peptide, brain homogenates are analyzed from treated and untreated mice by immunoprecipitation/Western blotting using the anti-Aβ 6E10 and 4G8 (Signet Laboratories, Dedham, MA). One can also compare Aβ40 and Aβ42 levels in the brains of treated and untreated mice by sandwich ELISA. There is a progressive increase in Aβ formation as a function of age in the 3×Tg-AD brains and a particularly pronounced effect on Aβ42 levels (87, herein incorporated by reference). Tau pathology is first apparent in the hippocampus of the 3×Tg-AD. Tau is conformationally altered and hyperphosphorylated at multiple residues in the brains of the 3×Tg-AD mice in an age-related and regional-dependent manner. Conformational-specific antibody MC1 and phospho-tau antibodies AT180, which detects phosphorylated threonine 231 and AT8, which detects tau phosphorylated at serine 202 and threonine 205 can be used.

Statistical Analysis: Results can be analyzed using GRAPHPAD PRISM or other commercial scientific graphing and statistics software. Statistical are performed between treated and untreated control mice using a Student's unpaired t test. Electrophysiological data are analyzed using Clampfit and Prism. Input-output curves are assessed by the slope of each fEPSP from the 5 to 80 µA, at 5-µA increments. PPF analysis compares the slope of the second elicited fEPSP and divided it by the first elicited fEPSP. Fiber volley amplitude is also analyzed to better assess synaptic transmission. Pre- and post-TBS baselines are analyzed by measuring fEPSP and comparing the pre-TBS baseline slope with the averaged post-TBS baseline. fEPSP slopes are expressed as a ratio of the pre-TBS baseline and normalized to the pre-TBS baseline. Significance levels are taken as p≤0.05.

Identifying Therapeutic Compounds: Identified candidate compounds that display PAM effects at norepinephrine to produce neurological, cognitive, and pathological improvement compared to untreated AD mice are generally considered therapeutic compounds.

D. Blood Pressure Screening

Next, successful identified therapeutic compounds can be assessed by assessing the treated and untreated mice from above for changes in blood pressure. Preferably, therapeutic compounds do not increase or alter blood pressure in the AD mouse model.

Assessment: Blood pressure. When mice are being tested for cognition as described above, one can also measure the mean arterial blood pressure using a blood pressure tail cuff piezoplethysmography method (see, e.g., procedures in references 108, and 114-115 all of which are herein incorporated by reference, including for a description of such methods). Mice are tested for blood pressure on separate days from the cognitive testing. Mice are placed into a warmed body restrainer and acclimated in a darken room for at least 15 minutes and trained for at least 3 days in this procedure before actual measurements are taken. Compounds that do not increase blood pressure by tail cuff method can be further confirmed by measuring blood pressure via an indwelling catheter in the carotid artery as described in reference 108 (herein incorporated by reference) or with doppler ultrasonic echocardiography.

Example 5

Compound 2 Data

Compound 2 (isomer #1) can increase the affinity of norepinephrine (neurotransmitter in brain) about 10 fold and also increase the affinity of epinephrine (hormone in heart function). Compound 2 is predicted to increase the cAMP signaling response but inhibit the inositol phosphate signaling response that increases the blood pressure. The cAMP response is thought to regulate neurotransmission in the brain and may increase cardiac output in the heart. The increased cardiac output would be therapeutic for heart failure and the preferred drug of choice as beta-adrenergic receptors and their cAMP output are downregulated in heart failure. Therefore, Compound 2 may be both cognitive-enhancing and cardioprotective and may result in an increased life span.

Figure 36:
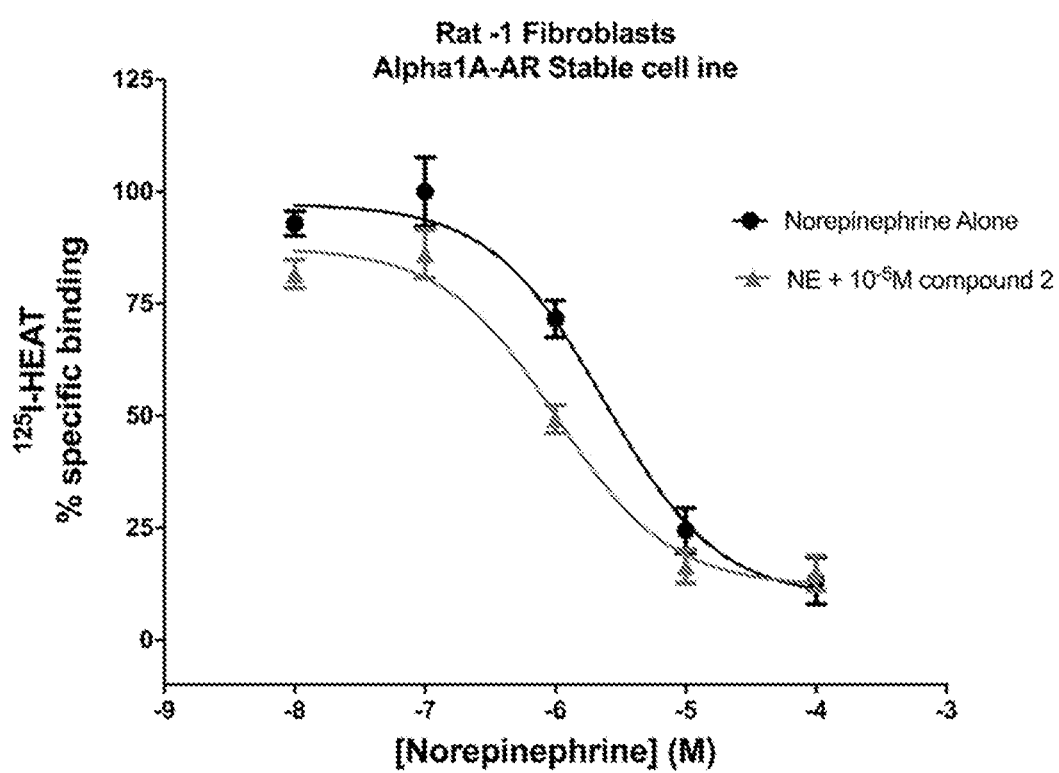
FIG. 36 shows a competition binding curve of norepinephrine at the alpha$_{1A}$-AR competing off the radiolabel antagonist $^{125}$I-HEAT with or without a $10^{-5}$M dose of compound 2 (also called isomer #1).
Figure 37:
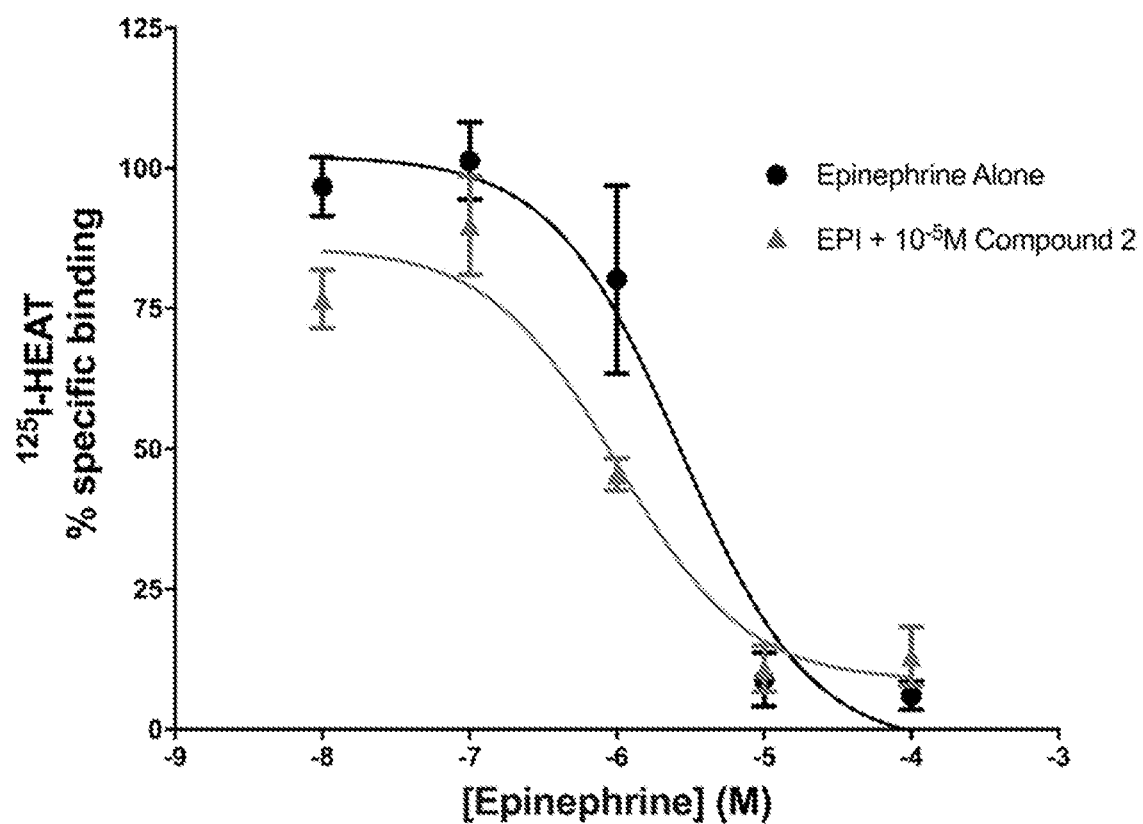
FIG. 37 shows a competition binding curve of epinephrine at the alpha$_{1A}$-AR competing off the radiolabel antagonist $^{125}$I-HEAT with or without a $10^{-5}$M dose of compound 2 (also called isomer #1).

Compound 2 (isomer #1) was characterized for its ligand binding properties at the $\alpha_1$-AR subtype, as described in Example 1 above, in a series of competition-binding experiments with the $\alpha_1$-AR-selective antagonist [$^{125}$I]HEAT as the radioligand. Compound 2 showed unique properties that suggest that it is a positive allosteric modulator (PAM) for BOTH norepinephrine (FIG. 36) and epinephrine (FIG. 37) so would activate the receptor throughout the body, not only in the brain. Compound 2 is not an agonist by itself, so should not increase the blood pressure response.

Example 6

Compound 10

Figure 38:
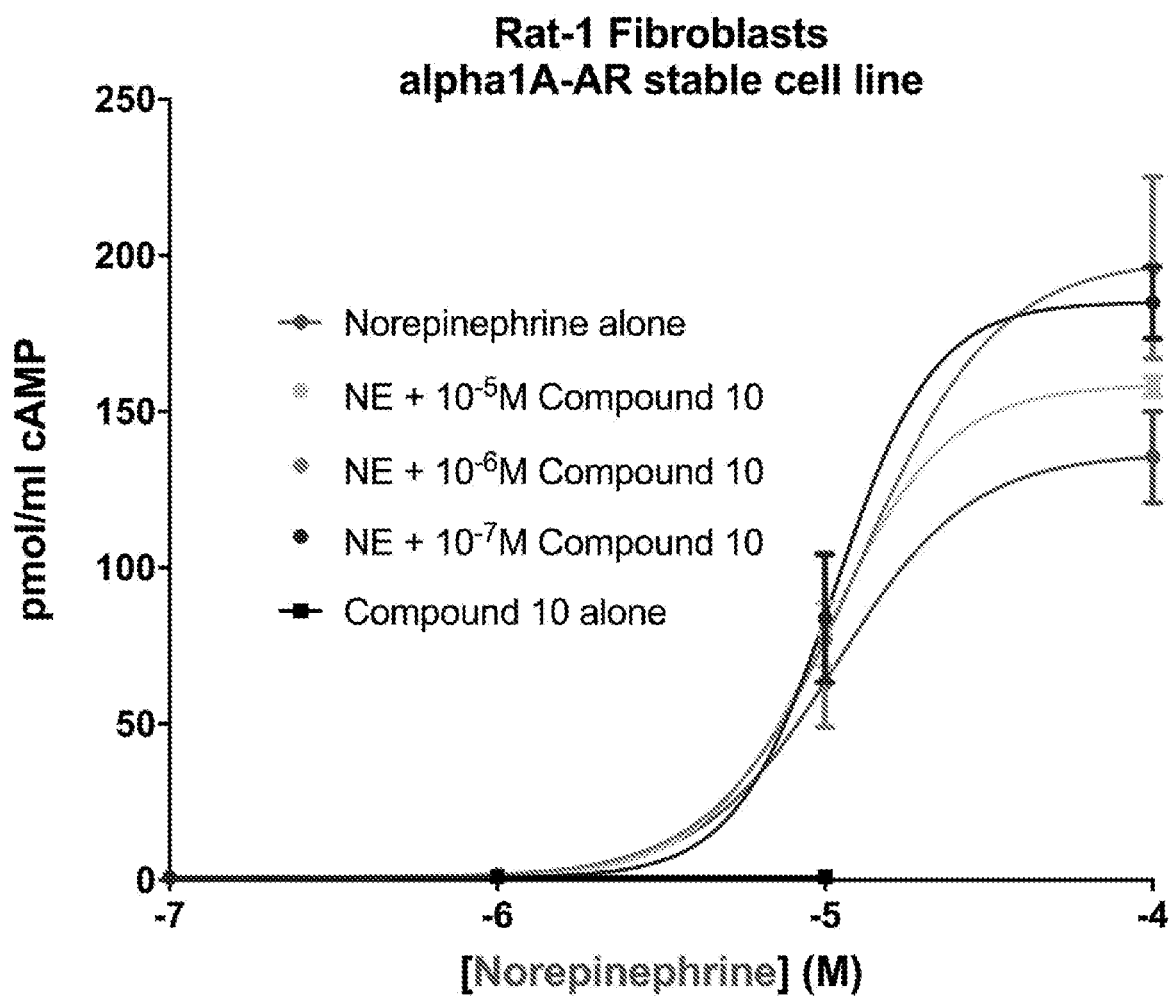
FIG. 38 shows data suggesting that Compound 10 is a positive allosteric modulator at the $\alpha_{1A}$-AR for norepinephrine at the cAMP response.
Figure 39:
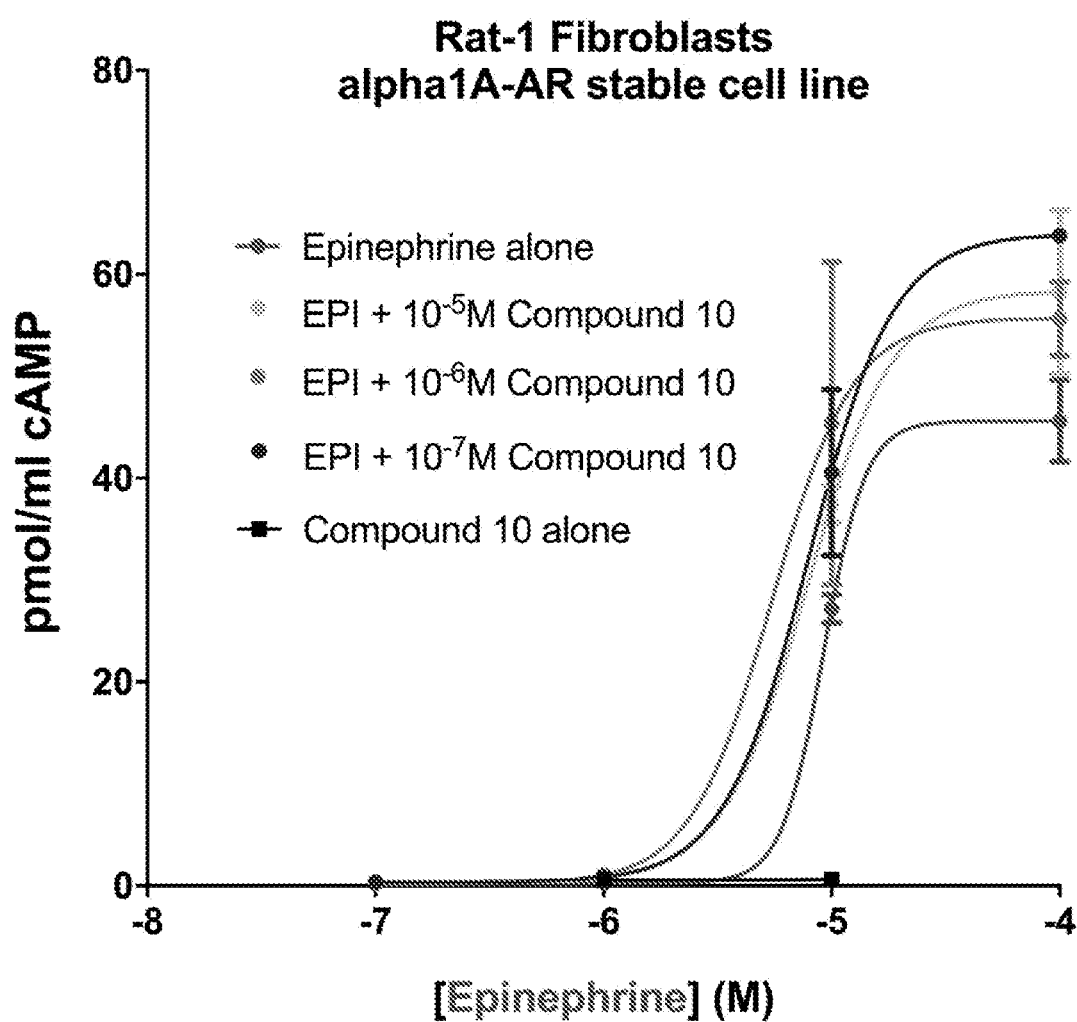
FIG. 39 shows data suggesting that Compound 10 is a positive allosteric modulator at the $\alpha_{1A}$-AR for epinephrine at the cAMP response.
Figure 40:
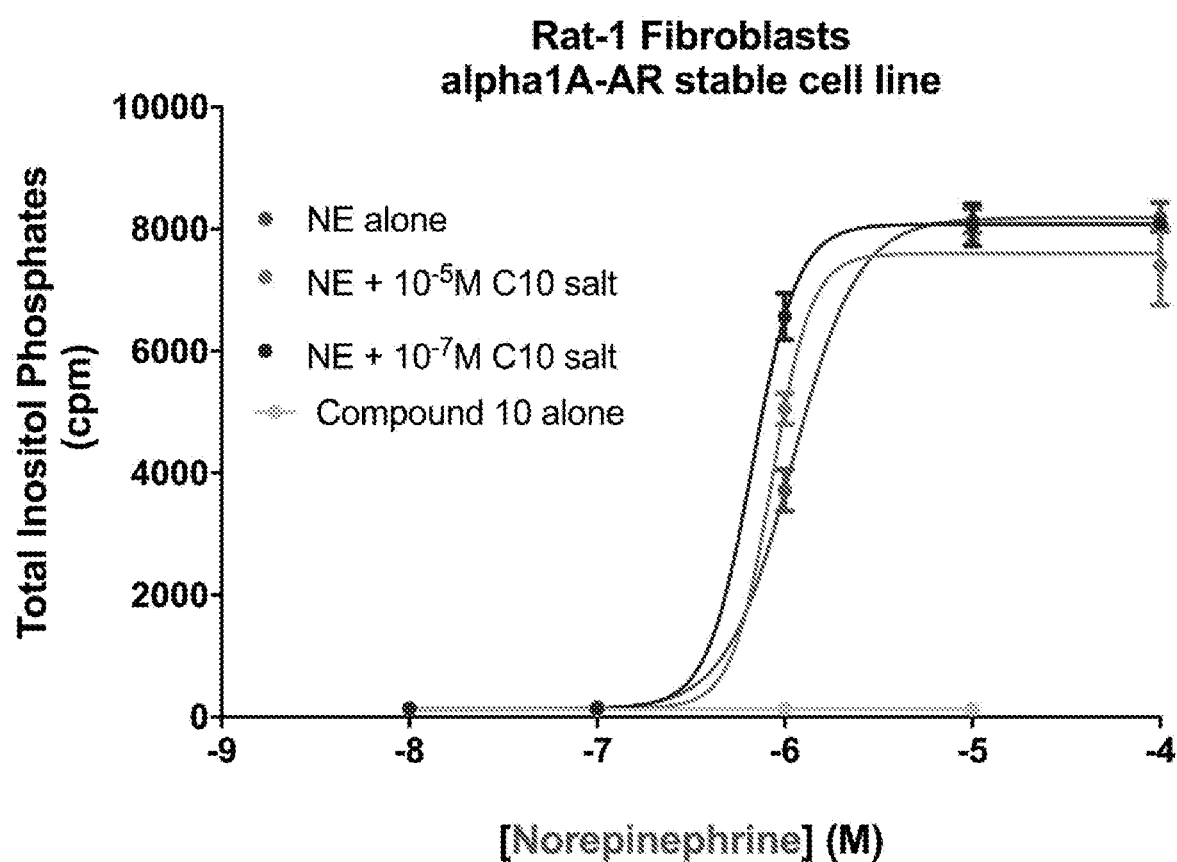
FIG. 40 shows data indicating that Compound 10 has the ability to increase the potency (i.e. EC50) of the norepinephrine mediated inositol phosphate response.
Figure 41:
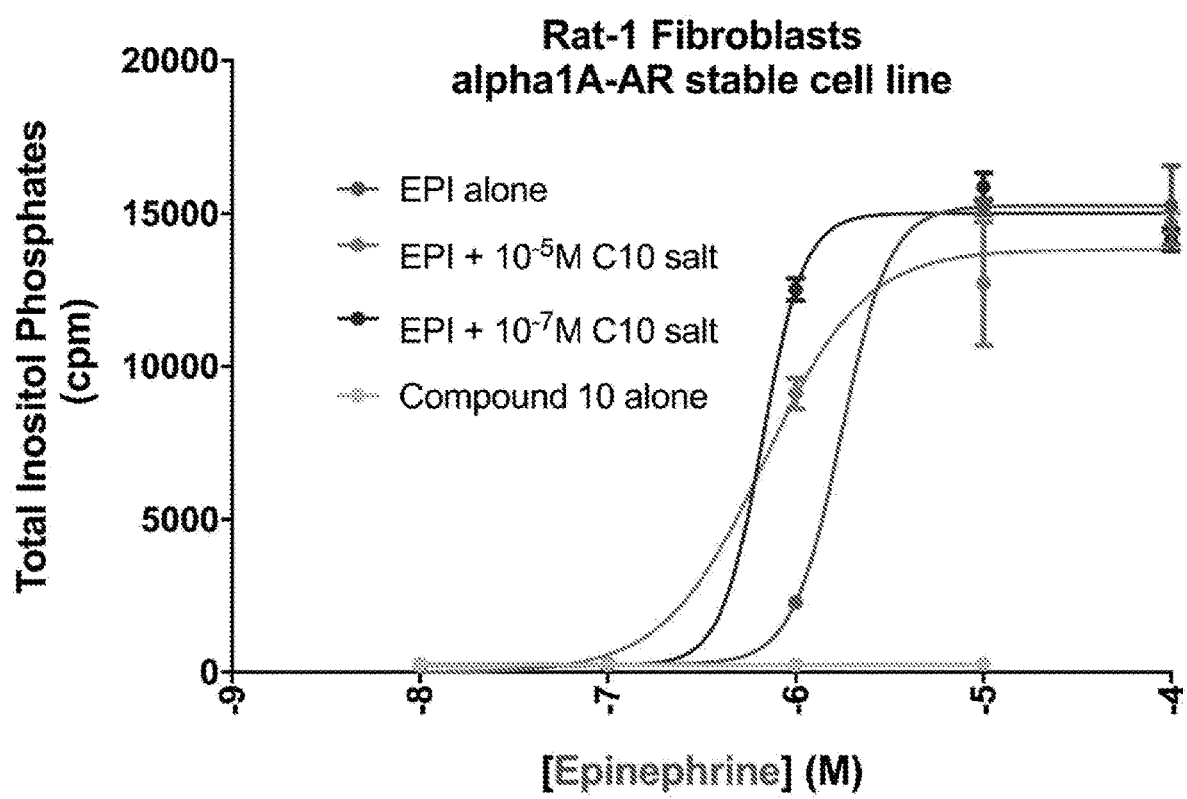
FIG. 41 shows data indicating that Compound 10 has the ability to increase the potency (i.e. EC50) of the epinephrine mediated inositol phosphate response.

Compound 10 also showed unique properties, different from Compound 3, but similar to Compound 2 that suggest that it is a positive allosteric modulator (PAM) at the $\alpha_{1A}$-AR for BOTH norepinephrine (FIG. 38) and epinephrine (FIG. 39) at the cAMP response. Unlike Compound 2 and 3, Compound 10 has the ability to increase the potency (i.e. EC50) of the norepinephrine (FIG. 40) and epinephrine (FIG. 41) mediated inositol phosphate response. Therefore, Compound 10 would potentiate both hormones (norepinephrine and epinephrine) and this effect would be throughout the body, not only in the brain or synapses. Compound 10 is not an agonist by itself, so similar to Compounds 2 and 3, should not increase the blood pressure response. The cAMP response is thought to regulate neurotransmission in the brain and may increase cardiac output in the heart. The increased cardiac output would be therapeutic for heart failure and the preferred drug of choice as beta-adrenergic receptors and their cAMP output are downregulated in heart failure. Therefore, Compound 10 may be both cognitive-enhancing and cardioprotective and may result in an increased life span.

Example 7

Synthesis of Compound 11 HCl Salt

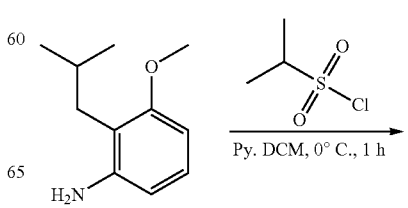

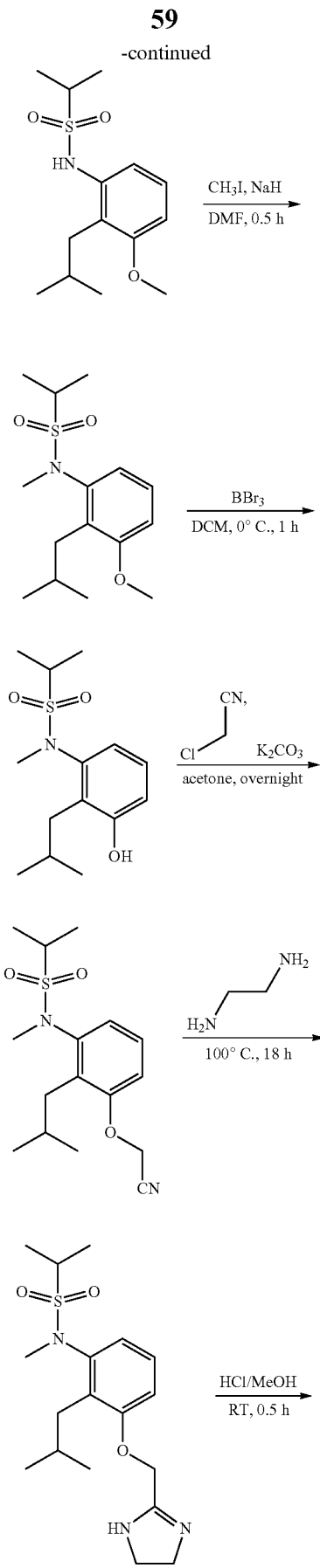

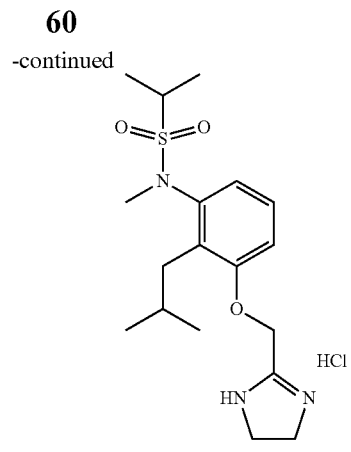

11

N-(2-Isobutyl-3-methoxyphenyl)propane-2-sulfonamide. 2-Isobutyl-3-methoxyaniline (500 mg, 2.79 mmol) was dissolved in DCM (15 mL), then pyridine (441 mg, 5.58 mol, 2.0 equiv) was added. The reaction mixture was cooled to 0° C. and propane-2-sulfonyl chloride (596 mg, 4.18 mmol, 1.5 equiv) was added dropwise. After 1 h, the reaction was complete and it was washed with water (3×20 mL). The organic phase was dried over anhydrous sodium sulfate and concentrated. The residue was purified on silica gel column chromatography using 0~20% EtOAc/Petroether to provide N-(2-isobutyl-3-methoxyphenyl)propane-2-sulfonamide (500 mg, 63% yield) as a yellow solid. LC-MS>94% (214, 254 nm), m/z=286.2 [M+H]$^+$.

N-(2-Isobutyl-3-methoxyphenyl)-N-methylpropane-2-sulfonamide. To a solution of N-(2-isobutyl-3-methoxyphenyl)methanesulfonamide (500 mg, 1.75 mmol) in dry DMF (15 mL) was added NaH (63 mg, 2.63 mmol, 1.5 equiv) and CH$_3$I (373 mg, 2.63 mmol, 1.5 equiv). The reaction mixture was stirred at rt for 0.5 h then water (50 mL) was added, it was extracted with EtOAc (3×20 mL). The combined organic phases were washed with brine (50 mL), dried over anhydrous sodium sulfate and concentrated. The residue was purified on silica gel column chromatography using 0~40% EtOAc/Petroether to provide N-(2-isobutyl-3-methoxyphenyl)-N-methylpropane-2-sulfonamide (510 mg, 98% yield) as a yellow solid. LC-MS>99% (214, 254 nm), m/z=300.2 [M+H]$^+$.

N-(3-Hydroxy-2-isobutylphenyl)-N-methylpropane-2-sulfonamide. To a solution of N-(2-isobutyl-3-methoxyphenyl)-N-methylmethanesulfonamide (510 mg, 1.71 mmol) in DCM (5 mL) at 0° C. was added BBr$_3$ (1.71 g, 6.83 mmol, 4.0 equiv) dropwise. After 1 h the reaction was complete, it was quenched with water (30 mL), and extracted with EtOAc (3×30 mL). The combined organic phases were dried over anhydrous sodium sulfate and concentrated. The residue was purified on silica gel column chromatography using 0~50% EtOAc/Petroether to provide N-(3-hydroxy-2-isobutylphenyl)-N-methylpropane-2-sulfonamide (400 mg, 83% yield) as a white solid. LC-MS>99% (214, 254 nm), m/z=286.0 [M+H]$^+$.

N-(3-(Cyanomethoxy)-2-isobutylphenyl)-N-methylpropane-2-sulfonamide. To a solution of N-(3-hydroxy-2-isobutylphenyl)-N-methylmethanesulfonamide (400 mg, 1.40 mmol) in acetone (20 mL) was added chloroacetonitrile (212 mg, 2.81 mmol, 2.0 equiv) and potassium carbonate (388 mg, 2.81 mmol, 2.0 equiv). The reaction mixture was stirred at 50° C. overnight. Then water (50 mL) was added and extracted with EtOAc (3×30 mL). The organics were combined, dried over anhydrous sodium sulfate and concentrated. The residue was purified on silica gel column chromatography using 0~50% EtOAc/Petroether to give N-(3-(cyanomethoxy)-2-isobutylphenyl)-N-methylpropane-2-sulfonamide (400 mg, 88% yield) as a yellow solid. LC-MS>95% (214, 254 nm), m/z=325.1 [M+H]$^+$.

N-(3-((4,5-Dihydro-1H-imidazol-2-yl)methoxy)-2-isobutylphenyl)-N-methylpropane-2-sulfonamide. The solution of N-(3-cyanomethoxy-2-isobutyl-phenyl)-N-methyl-methanesulfonamide (400 mg, 1.23 mmol) in ethylenediamine (4 mL) was heated to 100° C. for 56 hrs. The resulting solution was concentrated and purified on silica gel column chromatography using 0~100% EtOAc/Petroether then 0-20% MeOH/EtOAc as eluent to give N-(3-((4,5-dihydro-1H-imidazol-2-yl)methoxy)-2-isobutylphenyl)-N-methylpropane-2-sulfonamide (130 mg, 29% yield) as a colorless oil. LC-MS>99% (214, 254 nm), m/z=368.2 [M+H]$^+$.

Figure 2:
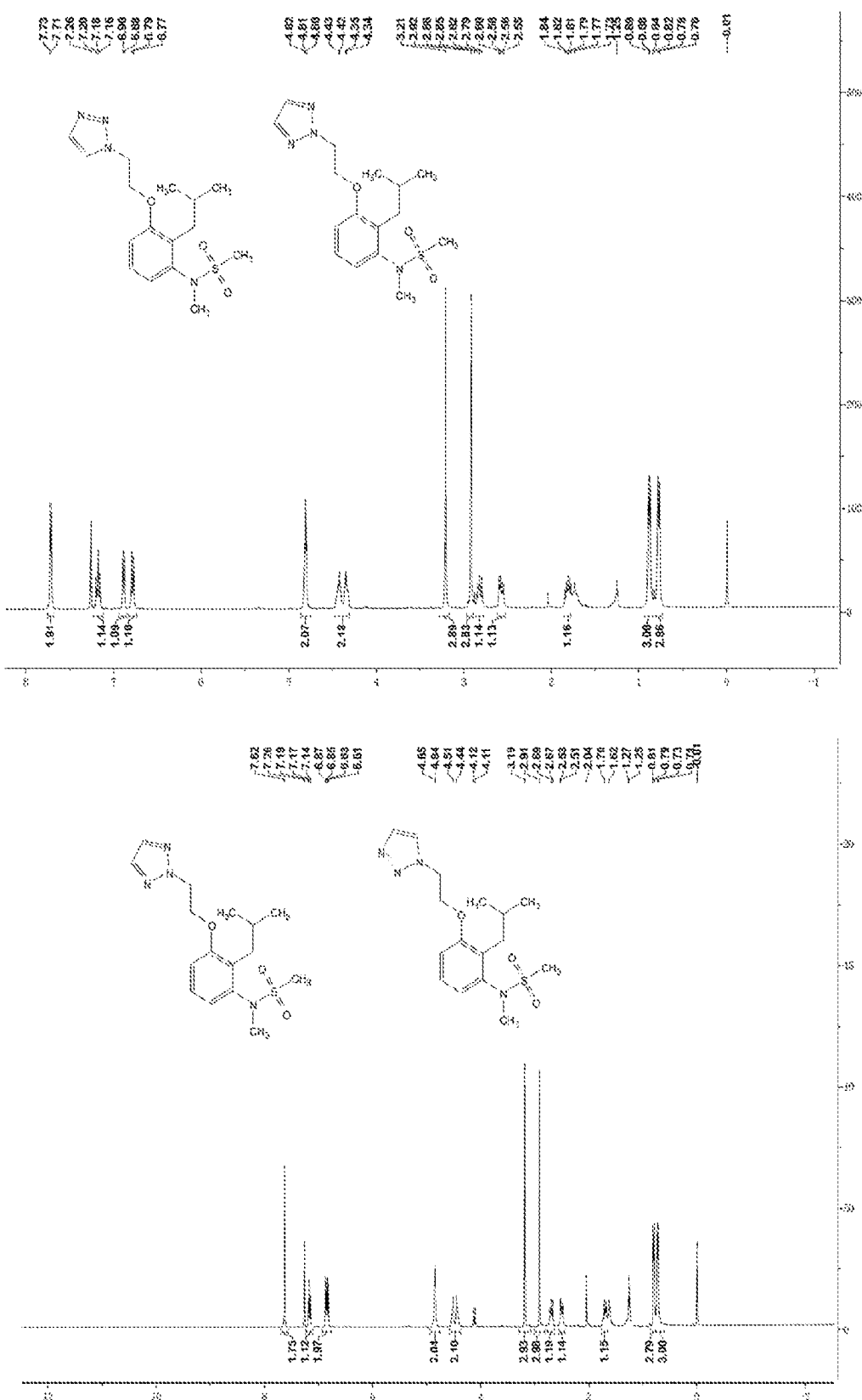
FIGS. 2A-J show $^1$H NMR spectra of exemplary compounds of Formula (I).
Figure 2:
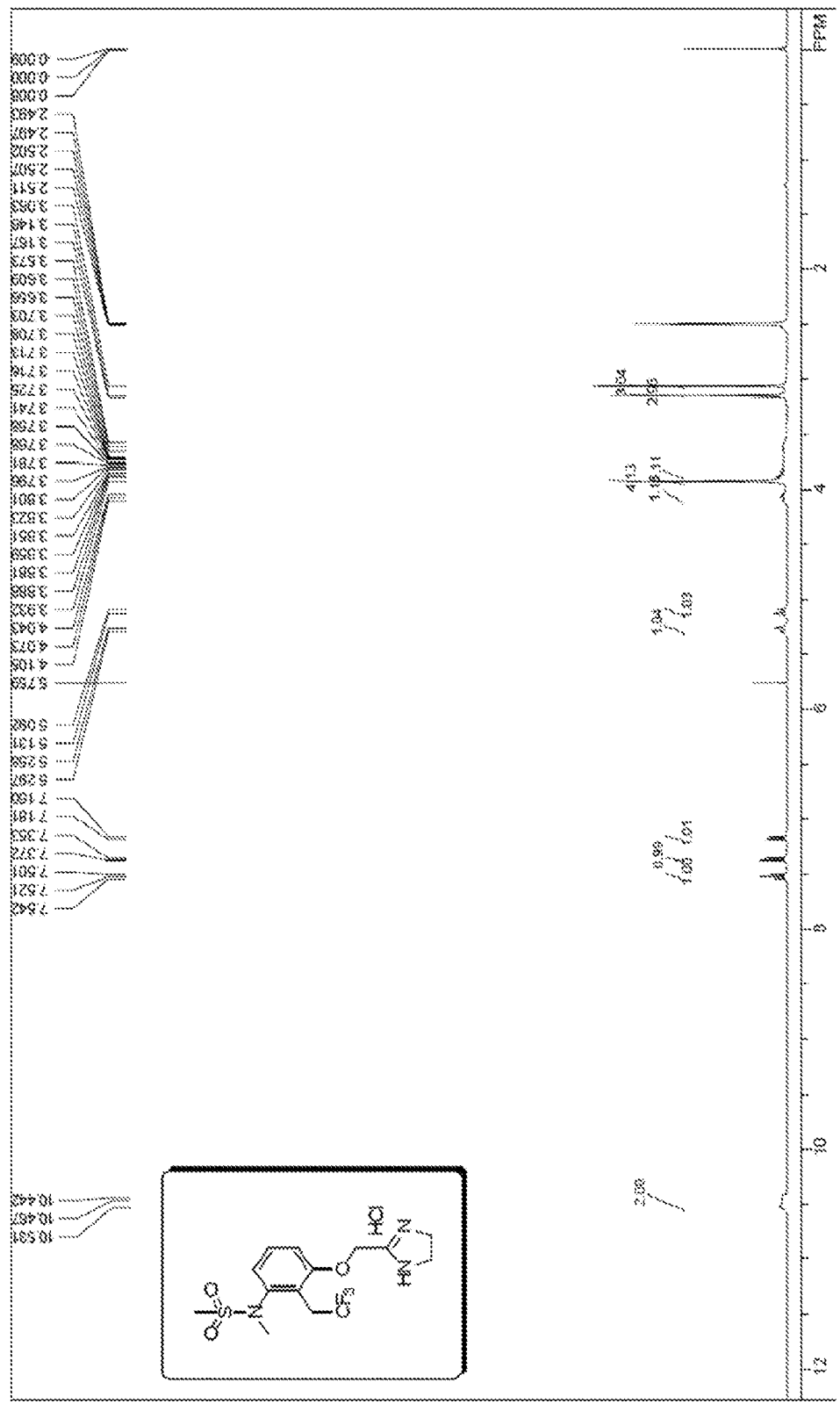

N-(3-((4,5-Dihydro-1H-imidazol-2-yl)methoxy)-2-isobutylphenyl)-N-methylpropane-2-sulfonamide hydrochloride (Compound 12). N-(3-((4,5-dihydro-1H-imidazol-2-yl)methoxy)-2-isobutylphenyl)-N-methylmethanesulfonamide (90 mg, 0.25 mmol) in MeOH (2 mL) was dissolved in HCl in MeOH (4 mol/L, 1.23 mL). It was stirred at room temperature for 30 min. After removing solvent under vacuo N-(3-((4,5-dihydro-1H-imidazol-2-yl)methoxy)-2-isobutylphenyl)-N-methylpropane-2-sulfonamide hydrochloride (Compound 12) (35.1 mg, 35.5% yield) was collected as a white solid. LC-MS>99% (214, 254 nm), m/z=368.1 [M+H]$^+$. $^1$H-NMR (400 MHz, DMSO-d$_6$) δ 10.39 (s, 2H), 7.29 (t, J=7.2 Hz, 1H), 7.17 (d, J=8.0 Hz, 1H), 7.01 (d, J=8.0 Hz, 1H), 5.15-5.04 (m, 2H), 3.92 (s, 4H), 3.61-3.54 (m, 1H), 3.17 (s, 3H), 2.74-2.69 (m, 2H), 1.95-1.88 (m, 1H), 1.38 (d, J=6.0 Hz, 3H), 1.24 (d, J=6.4 Hz, 3H), 0.87 (d, J=5.6 Hz, 3H), 0.80 (d, J=5.6 Hz, 3H). The NMR spectrum is shown in FIG. 2I.

Example 8

Synthesis of Compound 12 HCl Salt

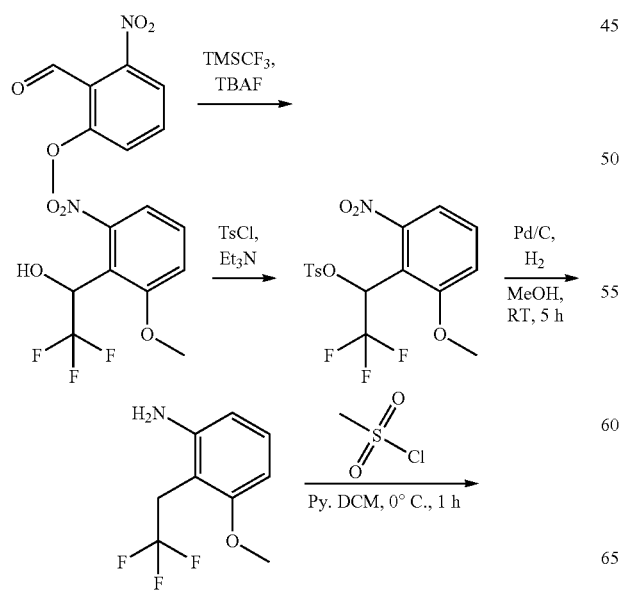

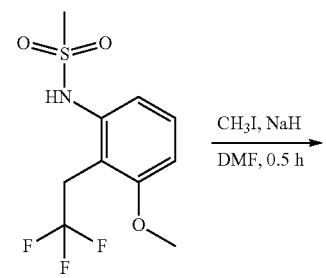

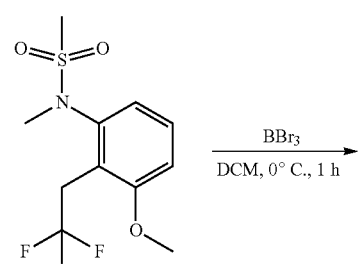

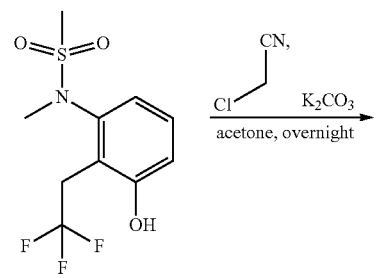

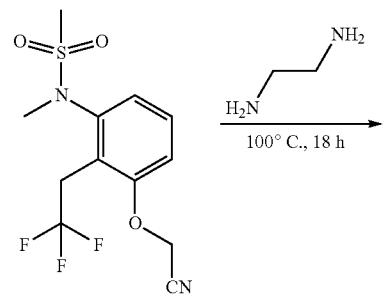

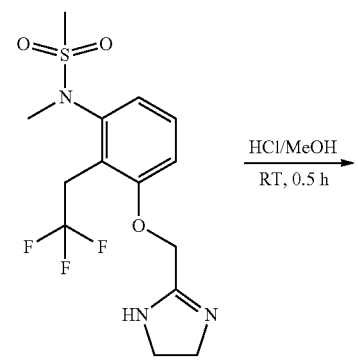

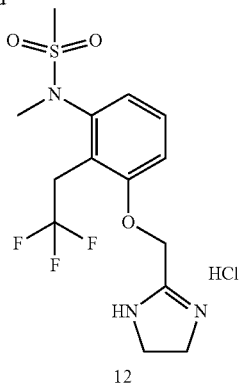

12

2,2,2-Trifluoro-1-(2-methoxy-6-nitrophenyl)ethanol. To a solution of 2-methoxy-6-nitrobenzaldehyde (3.0 g, 16.57 mmol) in THF (20 mL) were added a 1M solution of TBAF (1.02 g, 16.57 mmol, 2.0 equiv) and trimethyl(trifluoromethyl)silane (4.71 g, 33.14 mmol, 2.0 equiv) at room temperature, and the mixture was stirred for 2 hrs. Water (50 mL) was added and the solution was extracted with EtOAc (3×20 mL). The combined organics were washed with brine (50 mL), dried over anhydrous sodium sulfate and concentrated. The residue was purified on silica gel column chromatography using 0~20% EtOAc/Petroether to provide the title compound (3.8 g, 98% yield) as a yellow solid. LC-MS>99% (214, 254 nm), m/z=234.2 [M–OH]$^+$.

2,2,2-Trifluoro-1-(2-methoxy-6-nitrophenyl)ethyl 4-methylbenzenesulfonate. To a solution of 2,2,2-trifluoro-1-(2-methoxy-6-nitrophenyl)ethanol (3.8 g, 15.14 mmol) in DCM (30 mL) were added triethylamine (3.06 g, 30.28 mmol, 2.0 equiv) and tosyl chloride (3.17 g, 16.65 mmol, 1.1 equiv) at room temperature, and the mixture was stirred for 20 hrs. Water (50 mL) was added and the solution was extracted with EtOAc (3×30 mL). The combined organics were washed with brine (50 mL), dried over anhydrous sodium sulfate and concentrated. The residue was purified on silica gel column chromatography using 0~20% EtOAc/Petroether to provide the title compound (3.4 g, 55% yield) as a yellow solid. LC-MS>99% (214, 254 nm).

3-Methoxy-2-(2,2,2-trifluoroethyl)aniline. A mixture of 2,2,2-trifluoro-1-(2-methoxy-6-nitrophenyl)ethyl 4-methylbenzenesulfonate (3.4 g, 8.39 mmol) and 10 percent Pd/C (340 mg, 20% wt) in MeOH (30 mL) was hydrogenated for 3 hrs. Then the reaction was cooled to rt, filtered and concentrated to provide the title compound (1.0 g, 58% yield) as a yellow solid. LC-MS>99% (214, 254 nm), m/z=206.1 [M+H]$^+$.

N-(3-Methoxy-2-(2,2,2-trifluoroethyl)phenyl)methanesulfonamide. 3-Methoxy-2-(2,2,2-trifluoroethyl)aniline (1 g, 4.88 mmol) was dissolved in DCM (20 mL), then pyridine (772 mg, 9.76 mol, 2.0 equiv) was added. The reaction mixture was cooled to 0° C. and propane-2-sulfonyl chloride (838 mg, 7.32 mmol, 1.5 equiv) was added dropwise. After 1 h, the reaction was completed and it was washed with water (3×20 mL). The organic phase was dried over anhydrous sodium sulfate and concentrated. The residue was purified on silica gel column chromatography using 0-25% EtOAc/Petroether to provide the title compound (450 mg, 33% yield) as a yellow solid. LC-MS>94% (214, 254 nm), m/z=284.2 [M+H]+.

N-(3-Methoxy-2-(2,2,2-trifluoroethyl)phenyl)-N-methyl-methanesulfonamide. To a solution of N-(3-methoxy-2-(2,2,2-trifluoroethyl)phenyl)methanesulfonamide (450 mg, 1.59 mmol) in dry DMF (15 mL) was added NaH (57 mg, 2.39 mmol, 1.5 equiv) at 0° C. under N$_2$, and stirred for 30 min. Then CH$_3$I (339 mg, 2.39 mmol, 1.5 equiv) was added dropwise. The mixture was allowed warm up to rt and stirred for 30 min. Water (50 mL) was added and it was extracted with EtOAc (3×20 mL). The combined organics were washed with brine (50 mL), dried over anhydrous sodium sulfate and concentrated. The residue was purified on silica gel column chromatography using 0~30% EtOAc/Petroether to provide the title compound (450 mg, 95% yield) as a yellow solid. LC-MS>99% (214, 254 nm), m/z=298.2 [M+H]$^+$.

N-(3-Hydroxy-2-(2,2,2-trifluoroethyl)phenyl)-N-methyl-methanesulfonamide. To a solution of N-(3-methoxy-2-(2,2,2-trifluoroethyl)phenyl)-N-methylmethanesulfonamide (450 mg, 1.52 mmol) in DCM (5 mL) at 0° C. was added BBr$_3$ (1.52 g, 6.06 mmol, 4.0 equiv) dropwise. After stirred for 1 h, the reaction was quenched with water (30 mL), and extracted with EtOAc (3×30 mL). The combined organics were washed with brine, dried over anhydrous sodium sulfate and concentrated. The residue was purified on silica gel column chromatography using 0~50% EtOAc/Petroether to provide the title compound (340 mg, 79% yield) as a white solid. LC-MS>99% (214, 254 nm), m/z=284.0 [M+H]$^+$.

N-(3-(Cyanomethoxy)-2-(2,2,2-trifluoroethyl)phenyl)-N-methylmethanesulfonamide. To a solution of N-(3-hydroxy-2-(2,2,2-trifluoroethyl)phenyl)-N-methylmethanesulfonamide (340 mg, 1.20 mmol) in acetone (20 mL) was added chloroacetonitrile (181 mg, 2.40 mmol, 2.0 equiv) and potassium carbonate (332 mg 2.40 mmol, 2.0 equiv). The reaction mixture was stirred at 50° C. overnight. Then water (50 mL) was added and extracted with EtOAc (3×30 mL). The combined organics were washed with brine, dried over anhydrous sodium sulfate and concentrated. The residue was purified on silica gel column chromatography using 0~30% EtOAc/Petroether to give the title compound (350 mg, 91% yield) as a yellow solid. LC-MS>95% (214, 254 nm), m/z=323.1 [M+H]$^+$.

N-(3-((4,5-Dihydro-1H-imidazol-2-yl)methoxy)-2-(2,2,2-trifluoroethyl)phenyl)-N-methylmethanesulfonamide. The solution of N-(3-(cyanomethoxy)-2-(2,2,2-trifluoroethyl)phenyl)-N-methylmethanesulfonamide (350 mg, 1.09 mmol) in ethylenediamine (3.5 mL) was heated to 100° C. for 56 hrs. The solvent was removed under reduced pressure and the residue was purified on silica gel column chromatography using 0~100% EtOAc/Petroether then 0-20% MeOH/EtOAc as eluent to give the title compound (189 mg, 29% yield) as a colorless oil. LC-MS>99% (214, 254 nm), m/z=366.2 [M+H]$^+$.

N-(3-((4,5-Dihydro-1H-imidazol-2-yl)methoxy)-2-(2,2,2-trifluoroethyl)phenyl)-N-methylmethanesulfonamide hydrochloride (Compound 12). To a solution of N-(3-((4,5-dihydro-1H-imidazol-2-yl)methoxy)-2-(2,2,2-trifluoroethyl)phenyl)-N-methylmethanesulfonamide (90 mg, 0.25 mmol) in MeOH (2 mL) was added a 4M solution of HCl (1.23 mL, in MeOH). The mixture was stirred for 30 min at room temperature. Then the solvent was removed under reduced pressure to give the title compound (Compound 12) (98.1 mg, 98% yield) as a white solid. LC-MS>99% (214, 254 nm), m/z=366.2 [M+H]$^+$. $^1$H NMR (400 MHz, DMSO-d$_6$) δ 10.47 (s, 2H), 7.52 (t, J=8.4 Hz, 1H), 7.36 (d, J=7.6 Hz, 1H), 7.17 (d, J=8.4 Hz, 1H), 5.28 (d, J=15.6 Hz, 1H), 5.11 (d, J=15.6 Hz, 1H), 4.11-4.04 (m, 1H), 3.93 (s, 4H), 3.89-3.81 (m, 1H), 3.15 (s, 3H), 3.06 (s, 3H). The NMR spectrum is shown in FIG. 2J.

Example 9
Synthesis of Compound 13 HCl Salt
Compound 13 can be synthesized, for example, according to Schemes A and B below.
Scheme A
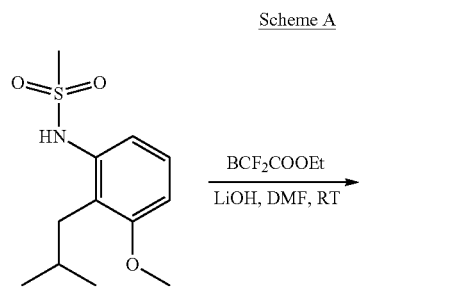
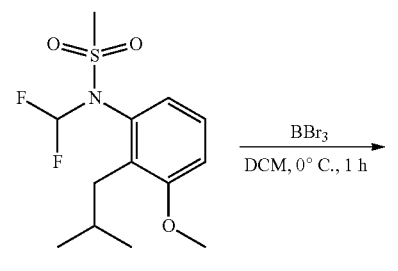
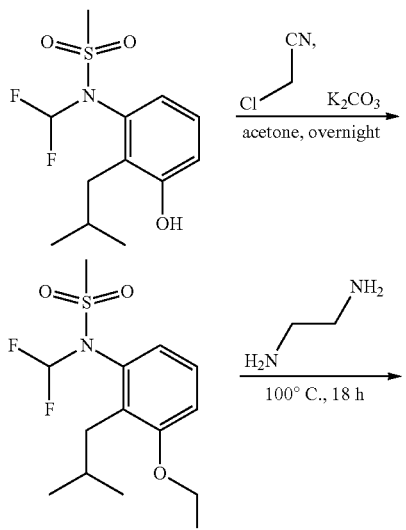
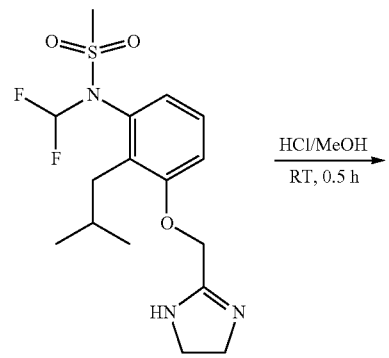
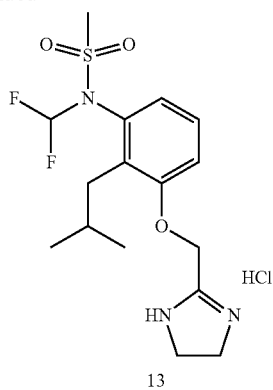 [SMILES: CC(C)Cc1c(OCC2=NCCN2)cccc1N(C(F)F)S(C)(=O)=O ; Cl]
13
Scheme B
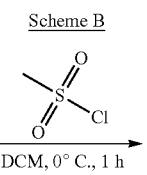

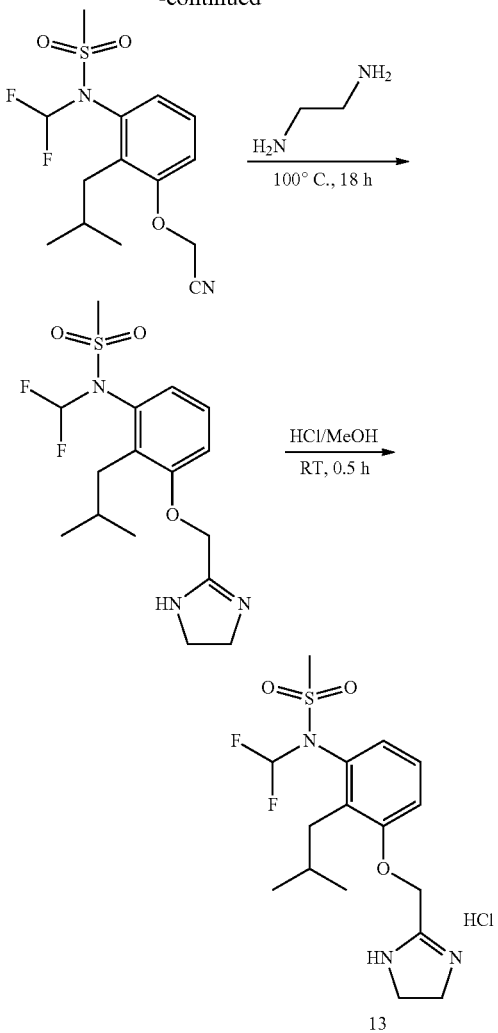

REFERENCES

1. Selkoe D J. Alzheimer's disease genes, proteins, and therapy. Physiol. Rev., 2001; 81:741-766.
2. Delacourte A, et al. The biochemical pathway of neurofibrillary degeneration in aging and Alzheimer's disease. Neurology. 1999; 52:1158-1165.
3. DeKosky S T, S. W Scheff. Synapse loss in frontal cortex biopsies in Alzheimer's disease correlation with cognitive severity. Ann. Neurol., 1990; 27: 457-464.
4. Dickson D W, et al. Correlations of synaptic and pathological markers with cognition of the elderly. Neurobiol. Aging, 1995; 16: 285-304.
5. Flood D G, P. D Coleman. Hippocampal plasticity in normal aging and decreased plasticity in Alzheimer's disease. Prog. Brain Res., 1990; 83: 435-443.
6. Masliah E, et al. Altered expression of synaptic proteins occurs early during progression of Alzheimer's disease. Neurology, 2001; 56: 127-129.
7. Sze C I, et al. Loss of the presynaptic vesicle protein synaptophysin in hippocampus correlates with cognitive decline in Alzheimer disease. J. Neuropathol. Exp. Neurol., 1997; 56: 933-944.
8. Chapman P F, et al. Impaired synaptic plasticity and learning in aged amyloid precursor protein transgenic mice. Nat. Neurosci. 1999; 2: 271-276.
9. Jacobsen J S, et al. Early-onset behavioral and synaptic deficits in a mouse model of Alzheimer's disease. Proc. Natl. Acad. Sci. U.S.A. 2006; 103: 5161-5166.
10. Auffret A, et al. Progressive age-related impairment of the late long-term potentiation in Alzheimer's disease presenilin-1 mutant knock-in mice. J. Alzheimers Dis. 2010; 19:1021-1033.
11. Middei S, et al. Learning discloses abnormal structural and functional plasticity at hippocampal synapses in the APP23 mouse model of Alzheimer's disease. Learn. Mem. 2010; 17, 236-240.
12. Ondrejcak T, et al. Alzheimer's disease amyloid β-protein and synaptic function. Neuromol Med. 2010; 12, 13-26.
13. Tran T T, et al. Chronic psychosocial stress accelerates impairment of long-term memory and late-phase long-term potentiation in an at-risk model of Alzheimer's disease. Hippocampus. 2011; 21(7):724-32.
14. Cullen W K, et al. Block of LTP in rat hippocampus in vivo by beta-amyloid precursor protein fragments. Neuroreport 1997; 8: 3213-3217.
15. Klyubin I, et al. Soluble Arctic amyloid beta protein inhibits hippocampal long-term potentiation in vivo. Eur. J. Neurosci. 2004; 19: 2839-2846.
16. Wang Q, et al. Block of long-term potentiation by naturally secreted and synthetic amyloid beta-peptide in hippocampal slices is mediated via activation of the kinases c-Jun N-terminal kinase, cyclin-dependent kinase 5, and p38 mitogen-activated protein kinase as well as metabotropic glutamate receptor type 5. J. Neurosci. 2004; 24: 3370-3378.
17. Shankar G M, et al. Amyloid-beta protein dimers isolated directly from Alzheimer's brains impair synaptic plasticity and memory. Nat. Med. 2008; 14: 837-842.
18. Chadwick W, et al. Amitriptyline-mediated cognitive enhancement in aged 3xTg Alzheimer's disease mice is associated with neurogenesis and neurotrophic activity. PLoS One. 2011; 6(6):e21660.
19. Hamilton L K, et al. Widespread deficits in adult neurogenesis precede plaque and tangle formation in the 3xTg mouse model of Alzheimer's disease. Eur J Neurosci. 2010 September; 32(6):905-20.
20. Perez D M and Doze V A. "Cardiac and Neuroprotection Regulated by $α_1$-Adrenergic Receptor Subtypes. J Recept Signal Transduct Res. 2011; 31(2):98-110.
21. Zuscik M J, et al., Perez D M. Overexpression of the $α_{1b}$-Adrenergic receptor causes apoptotic neurodegeneration: A multiple system atrophy. Nature Medicine 2000; 6:1388-1394.
22. Kunieda T, et al., Perez D M, Najm I M. Systemic overexpression of the am-adrenergic receptor in mice: An animal model of epilepsy. Epilepsia 2002; 43: 1324-1329.
23. Papay R, et al., Perez D M. Mice expressing the $α_{1b}$-Adrenergic receptor induces a synucleinopathy with excessive tyrosine nitration but decreased phosphorylation. J. Neurochem. 2002; 83:623-634.
24. Doze V A, et al., Perez D M. Long term $α_{1A}$-adrenergic receptor stimulation improves synaptic plasticity, cognitive function, mood and longevity. Mol Pharmacology 2011; 80(4):747-58.
25. Papay R, et al., Perez D M. Localization of the Mouse $α_{1A}$-Adrenergic Receptor in the Brain: $α_{1A}$-AR is expressed in Neurons, GABAergic Interneurons and NG2 Oligodendrocyte Progenitors. J. Comparative Neurology. 2006; 497: 209-222.
26. Gupta M K, et al., Perez D M. $α_1$-Adrenergic receptors regulate neurogenesis and gliogenesis. Molecular Pharmacology. 2009; 76(2):314-26.

27. Rorabaugh B R, et al., Perez D M. The $\alpha_{1A}$- but not the $\alpha_{1B}$-Adrenergic Receptor Preconditions the Ischemic Mouse Heart through a staurosporine-sensitive, chelerythrine-insensitive mechanism. Cardiovas Research 2005; 65:436-45.

28. Shi T, Papay R S and Perez D M. $\alpha_{1A}$-Adrenergic receptor prevents cardiac ischemic damage through PKCδ/GLUT1/4-mediated glucose uptake. *J Receptors Signal Transduction,* 36(3):261-70, 2016.

29. Szot P, et al. Changes in adrenoreceptors in the prefrontal cortex of subjects with dementia: evidence of compensatory changes. Neuroscience. 2007; 146(1):471-80.

30. Shimohama S, et al. Biochemical characterization of $\alpha_1$-adrenergic receptors in human brain and changes in Alzheimer-type dementia. J Neurochem. 1986; 47(4):1295-301.

31. Hong C J, et al. A study of α-adrenoceptor gene polymorphisms and Alzheimer disease. J Neural Transm. 2001; 108(4):445-50.

32. Szot P, White S S, Greenup J L, Leverenz J B, Peskind E R, Raskind M A. Alpha1-adrenoreceptor in human hippocampus: binding and receptor subtype mRNA expression. Brain Res Mol Brain Res. 2005 Oct. 3; 139(2):367-71.

33. Sirvia J, MacDonald E. Central $\alpha_1$-adrenoceptors: their role in the modulation of attention and memory formation. Pharmacol Ther 1999; 83: 49-65.

34. Arnsten A F, Jentsch J D. The $\alpha_1$-adrenergic agonist, cirazoline, impairs spatial working memory performance in aged monkeys. Pharmacol Biochem Behav. 1997 September; 58(1):55-9.

35. Gibbs M E, Summers R J. Stimulation of $\alpha_1$-adrenoceptors inhibits memory consolidation in the chick. Eur J Neurosci 2001; 14:1369-1376.

36. Puumala T, et al. Stimulation of $\alpha_1$-adrenergic receptors facilitates spatial learning in rats. Eur Neuropsychopharmacol 1998; 8:17-26.

37. Puumala T, Sirviö J. Stimulation and blockade of $\alpha_1$-adrenoceptors affect behavioural activity, but not spatial working memory assessed by delayed non-matching to position task in rats. J Psychopharmacol 1997; 11:45-51.

38. Ferry B, et al. Involvement of $\alpha_1$-adrenoceptors in the basolateral amygdala in modulation of memory storage. Eur J Pharmacol 1999; 372:9-16.

39. Minneman K P, et al. Selectivity of agonists for cloned $\alpha_1$-adrenergic receptor subtypes. Mol Pharmacol 1994; 46:936.

40. Puumala T, et al. Effects of St-587 and prazosin on water maze and passive avoidance performance of scopolamine-treated rats. Pharmacol Biochem Behav 1996; 55:107-115.

41. Puumala T, et al. Stimulation of $\alpha_1$-adrenergic receptors facilitates spatial learning in rats. Eur Neuropsychopharmacol 1999; 8:17-26.

42. Moshfegh A, et al. Involvement of dorsal hippocampal $\alpha_1$-adrenergic receptors in the effect of WIN55, 212-2 on memory retrieval in inhibitory avoidance task. Neurosci Lett 2011; 489:69-73.

43. Azami N S, et al. Involvement of dorsal hippocampal α-adrenergic receptors in the effect of scopolamine on memory retrieval in inhibitory avoidance task. Neurobiol Learn Mem 2010; 93:455-462.

44. Zarrindast M R, et al. The role of α-adrenoceptors in the amnestic effect of intracerebroventricular dexamethasone. Pharmacological Res 2002; 46:339-344.

45. Segal M, Markram H, Richter-Levin G. Actions of norepinephrine in the rat hippocampus. *Prog Brain Res* 1991; 88:323-330.

46. Wood P L, Ryan R, Li M. Excitatory amino acid signal transduction in the hippocampus: role of noradrenergic afferents and nitric oxide in cGMP increases in vivo. *Life Sci* 1992; 51:601-606.

47. Lynch G, Granger R. Variations in synaptic plasticity and types of memory in corticohippocampal networks. *J Cogn Neurosci* 1992; 4:189-199.

48. Nicoll R A, Malenka R C. Contrasting properties of two forms of long-term potentiation in the hippocampus. *Nature* 1995; 377:115-118.

49. Katsuki H, Izumi Y, Zorumski C F. Noradrenergic regulation of synaptic plasticity in the hippocampal CA1 region. *J Neurophysiol* 1997; 77:3013-3020.

50. Pussinen R, Sirviö J. Minor role for $\alpha_1$-adrenoceptors in the facilitation of induction and early maintenance of long-term potentiation in the CA1 field of the hippocampus. *J Neurosci Res* 1998; 51:309-315.

51. Izumi Y, Zorumski C F. Norepinephrine promotes long-term potentiation in the adult rat hippocampus in vitro. *Synapse* 1999; 31:196-202.

52. Scheiderer C L, Smith C C, McCutchen E, McCoy P A, Thacker E E, Kolasa K, Dobrunz L E, McMahon L L. Coactivation of M(1) muscarinic and $\alpha_1$-adrenergic receptors stimulates extracellular signal-regulated protein kinase and induces long-term depression at CA3-CA1 synapses in rat hippocampus. *J Neurosci* 2008; 28:5350-5358.

53. Scheiderer C L, Dobrunz L E, McMahon L L. Novel form of long-term synaptic depression in rat hippocampus induced by activation of $\alpha_1$-adrenergic receptors. *J Neurophysiol* 2004; 91:1071-1077.

54. Scanziani M, Gahwiler B H, Thompson S M. Presynaptic inhibition of excitatory synaptic transmission mediated by a-adrenergic receptors in area CA3 of the rat hippocampus in vitro. *J Neurosci* 1993; 13:5393-5401.

55. Rutecki P A. Noradrenergic modulation of epileptiform activity in the hippocampus. *Epilepsy Res* 1995; 20:125-136.

56. Ul Haq R, Liotta A, Kovacs R, Rösler A, Jarosch M J, Heinemann U, Behrens C J. Adrenergic modulation of sharp wave-ripple activity in rat hippocampal slices. *Hippocampus* 2012; 22:516-533.

57. Buzsaki G. Two stage model of memory trace formation: a role for "noisy" brain states. *Neuroscience* 1989; 31:551-570.

58. Liang, K. C., Juler, R. & McGaugh, J. L. (1986) Modulating effects of posttraining epinephrine on memory: involvement of the amygdala noradrenergic system. *Brain Res.,* 368, 125-133.

59. Liang, K.C., McGaugh, J. L. & Yao, H.-Y. (1990) Involvement of amygdala pathways in the influence of post-training intra-amygdala norepinephrine and peripheral epinephrine on memory storage. *Brain Res.,* 508, 225-233.

60. Introini-Collison, I. B., Miyazaki, B. & McGaugh, J. L. (1991) Involvement of the amygdala in the memory-enhancing effects of clenbuterol. *Psychopharmacology,* 104, 541-544.

61. Ferry, B., Roozendaal, B. & McGaugh, J. L. (1999b) Involvement of α1-adrenoceptors in the basolateral amygdala in modulation of memory storage. *Eur. J. Pharmacol.,* 372, 9-16.

62. Ferry, B., Roozendaal, B. & McGaugh, J. L. (1999c) Basolateral amygdala noradrenergic influences on memory storage are mediated by an interaction between β- and α1-adrenoceptors. *J. Neurosci.,* 19, 5119-5123.

63. Hatfield, T. & McGaugh, J. L. (1999) Norepinephrine infused into the basolateral amygdala enhances spatial water maze memory. *Neurobiol. Learn. Mem.,* 71, 232-239.

64. Perkins, J. P. & Moore, M. M. (1973) Characterization of the adrenergic receptors mediating a rise in cyclic 3',5'-adenosine monophosphate in rat cerebral cortex. *J. Pharmacol. Exp. Ther.*, 185,371-378.

65. Schultz, J. & Daly, J. W. (1973) Accumulation of cyclic adenosine 3',5'-monophosphate in cerebral cortical slices from rat and mouse: stimulatory effect of α- and β-adrenergic agents and adenosine. *J. Neurochem.*, 21, 1319-1326.

66. Leblanc, G. G. & Ciaranello, R. D. (1984) α-Noradrenergic potentiation of neurotransmitter-stimulated cAMP production in rat striatal slices. *Brain Res.*, 293, 57-65.

67. Johnston, R. D. & Minneman, K. P. (1986) Characterization of α1-adrenergic receptors which increase cyclic AMP accumulation in rat cerebral cortex. *Eur. J. Pharmacol.*, 129, 293-300.

68. Song Y, Huang Y, Dong E D, Han Q D, Zhang Y Y. Characterization of cAMP accumulation mediated by three alpha1-adrenoceptor subtypes in HEK293 cells. Acta Pharmacol Sin. 2003 June; 24(6):549-54.

69. Thonberg H, Fredriksson J M, Nedergaard J, Cannon B. A novel pathway for adrenergic stimulation of cAMP-response-element-binding protein (CREB) phosphorylation: mediation via alpha1-adrenoceptors and protein kinase C activation. Biochem J. 2002 May 15; 364(Pt 1):73-9.

70. Lin R Z, Chen J, Hu Z W, Hoffman B B. Phosphorylation of the cAMP response element-binding protein and activation of transcription by alpha1 adrenergic receptors. J Biol Chem. 1998 Nov. 6; 273(45):30033-8.

71. Harley C W, Darby-King A, McCann J, McLean J H. Beta1-adrenoceptor or alpha1-adrenoceptor activation initiates early odor preference learning in rat pups: support for the mitral cell/cAMP model of odor preference learning. Learn Mem. 2006 January-February; 13(1):8-13.

72. Shi T, Papay R S, Perez D M. The role of $\alpha_1$-adrenergic receptors in regulating metabolism: increased glucose tolerance, leptin secretion and lipid oxidation. J Recept Signal Transduct Res. 2017 April; 37(2):124-132

73. Collette K M, Zhou X D, Amoth H M, Lyons M J, Papay R S, Sens D A, Perez D M, Doze V A. Long-term $\alpha_{1B}$-adrenergic receptor activation shortens lifespan, while $\alpha_{1A}$-adrenergic receptor stimulation prolongs lifespan in association with decreased cancer incidence. Age (Dordr). 2014; 36(4):9675.

74. Schmeichel B E, Berridge C W. Wake-promoting actions of noradrenergic $\alpha_1$- and β-receptors within the lateral hypothalamic area. Eur J Neurosci. 2013 March; 37(6):891-900.

75. Stojkov N J, Baburski A Z, Bjelic M M, Sokanovic S J, Mihajlovic A I, Drljaca D M, Janjic M M, Kostic T S, Andric S A. In vivo blockade of $\alpha_1$-adrenergic receptors mitigates stress-disturbed cAMP and cGMP signaling in Leydig cells. Mol Hum Reprod. 2014 January; 20(1):77-88.

76. Bóta J, Hajagos-Tóth J, Ducza E, Samavati R, Borsodi A, Benyhe S, Gáspár R. The effects of female sexual hormones on the expression and function of $\alpha_{1A}$- and $\alpha_{1D}$-adrenoceptor subtypes in the late-pregnant rat myometrium. Eur J Pharmacol. 2015 Dec. 15; 769:177-84.

77. Shi T, Moravec C S and Perez D M. Novel proteins associated with human dilated cardiomyopathy: Selective reduction in $\alpha_{1A}$-adrenergic receptors and increased desensitization proteins. J Receptors Signal Transduction 2013; 33: 96-106.

78. Erne P, Conen D, Kiowski W, Bolli P, Müller F B, Bühler F R. Calcium antagonist induced vasodilation in peripheral, coronary and cerebral vasculature as important factors in the treatment of elderly hypertensives. Eur Heart J. 1987 November; 8 Suppl K:49-56.

79. Kiowski W. Place of calcium antagonists in the treatment of hypertension. Cor Vasa. 1990; 32(2 Suppl 1):2-11.

80. Kiowski W, Bolli P, Erne P, Müller F B, Hulthén U L, Bühler F R. Mechanisms of action and clinical use of calcium antagonists in hypertension. Circulation. 1989 December; 80(6 Suppl):IV136-44.

81. Hackos D H, Hanson, J E. Diverse modes of NMDA receptor positive allosteric modulation: Mechanisms and consequences. Neuropharmacology 2017; 112:34-45.

82. Allegretti M, Cesta M C, Locati M. Allosteric Modulation of Chemoattractant Receptors. Front Immunol. 2016 May 2; 7:170.

83. Targowska-Duda K M, Kaczor A A, Jozwiak K, Arias H R. Molecular interactions of type I and type II positive allosteric modulators with the human α7 nicotinic acetylcholine receptor: an in silico study. J Biomol Struct Dyn. 2018 Feb. 16:1-29 (ahead of print).

84. Leppik R A, Mynett A, Lazareno S, and Birdsall N J (2000) Allosteric interactions between the antagonist prazosin and amiloride analogs at the human $\alpha_{1A}$-adrenergic receptor. Mol Pharmacol 57:436-445.

85. Sharpe I A, Thomas L, Loughnan M, Motin L, Palant E, Croker D E, Alewood D, Chen S, Graham R M, Alewood P F, et al. (2003) Allosteric α1-adrenoreceptor antagonism by the conopeptide ρ-TIA. J Biol Chem 278:34451-34457.

86. Campbell A P, Wakelin L P, Denny W A, Finch A M. Homobivalent Conjugation Increases the Allosteric Effect of 9-aminoacridine at the α1-Adrenergic Receptors. Mol Pharmacol. 2017 February; 91(2):135-144.

87. Oddo S, et al. Amyloid deposition precedes tangle formation in a triple transgenic model of Alzheimer's disease. Neurobiol Aging 2003; 24:1063-1070.

88. Romberg C, et al. Impaired attention in the 3xTgAD mouse model of Alzheimer's disease: rescue by donepezil (Aricept). J Neurosci. 2011; 31(9):3500-7.

89. Sterniczuk R, et al. Characterization of the 3xTg-AD mouse model of Alzheimer's disease: part 2. Behavioral and cognitive changes. Brain Res. 2010 Aug. 12; 1348:149-55.

90. Attar A, et al. A shortened Barnes maze protocol reveals memory deficits at 4-months of age in the triple-transgenic mouse model of Alzheimer's disease. PLoS One. 2013 Nov. 13; 8(11):e80355

91. Grundman M (2005) Weight loss in the elderly may be a sign of impending dementia. Arch Neurol 62(1):20-22.

92. Burns J M, Johnson D K, Watts A, Swerdlow R H, Brooks W M (2010) Reduced lean mass in early Alzheimer disease and its association with brain atrophy. Arch Neurol 67(4):428-433.

93. Tamura B K, Masaki K H, Blanchette P (2007) Weight loss in patients with Alzheimer's disease. J Nutr Elder 26(3-4):21-38.

94. Hwa J, Graham R M and Perez D M: Identification of critical determinants of α1-adrenergic receptor subtype selective agonist binding J Biol Chem 270: 23189-23195, 1995.

95. Hwa J, Perez D M. The unique nature of the serine interactions for a1-adrenergic receptor agonist binding and activation. J Biol Chem. 1996 Mar. 15; 271(11):6322-7.

96. McCune D F, et al., Perez D M. Bulk is a Determinant of Oxymetazoline Affinity for the $\alpha_{1A}$-Adrenergic Receptor. Receptors and Channels 10: 109-116, 2004 (cover issue).

97. Waugh D J J, et al., Perez D M. Phe308 and Phe312 in TM VII are major sites of α1-AR Antagonist Binding: Imidazoline Agonists Bind Like Antagonists J. Biol. Chem. 276: 25366-25371, 2001.

98. Perez D M, Hwa J, Gaivin R, Mathur M, Brown F, and Graham R M: Constitutive Activation of a Single Effector Pathway: Evidence for Multiple Activation States of a G-Protein-Coupled Receptor. Mol Pharmacol. 49: 112-122, 1996.

99. Billings L M, et al Intraneuronal Aβ causes the onset of early Alzheimer's disease-related cognitive deficits in transgenic mice. Neuron. 2005; 45(5):675-88.

100. Hwa J, Graham R M and Perez D M: Chimeras of α1-adrenergic receptor subtypes identify critical residues that modulate active-state isomerization J. Biol. Chem. 271: 7956-7964, 1996.

101. Zhao M-M, Hwa, J and Perez D M: Identification of critical extracellular loop residues involved in α1-adrenergic receptor subtype selective antagonist binding. Mol. Pharmacol. 50: 1118-1126, 1996.

102. Porter J, Hwa J and Perez D M: Activation of the α1b-adrenergic receptor is initiated by disruption of an inter-helical salt-bridge constraint. J. Biol. Chem. 271: 28318-28323, 1996

103. Hwa J, Gaivin R, Porter J and Perez D M: Synergism of constitutive activity in α1-adrenergic receptor activation. Biochemistry 36: 633-639, 1997.

104. Zhao M-M, Gaivin, R J, and Perez D M. The third extracellular loop of the α2-adrenergic receptor can modulate receptor/G-protein affinity. Mol. Pharmacol. 53: 524-529, 1998.

105. Porter J, Edlemann S, Waugh D J, Piascik, M T, and Perez D M. The agonism and synergistic potentiation of partial agonists by triethylamine in α1-adrenergic receptor activation. Mol. Pharmacol. 53: 766-771, 1998.

106. Waugh D J, Zhao M M, Zuscik M J, Perez D M. Novel aromatic residues in transmembrane domains IV and V involved in agonist binding at alpha(1a)-adrenergic receptors. J Biol Chem. 2000 Apr. 21; 275(16):11698-705.

107. Waugh D J J, Gaivin R J, Zuscik M J, Gonzalez-Cabrera P, Ross S A, Yun J and Perez D M. Phe308 and Phe312 in TM VII are major sites of α1-Adrenergic Receptor Antagonist Binding: Imidazoline Agonists Bind Like Antagonists J. Biol. Chem. 276: 25366-25371, 2001.

108. Zuscik M J, et al., Perez D M. Hypotension, autonomic failure and cardiac hypertrophy in transgenic mice over-expressing the α1b-adrenergic receptor. J. Biol. Chem. 276: 13738-13743, 2001.

109. Daly C J, Ross R A, Whyte J, Henstridge C M, Irving A J, McGrath J C. Fluorescent ligand binding reveals heterogeneous distribution of adrenoceptors and 'cannabinoid-like' receptors in small arteries. Br J Pharmacol. 2010 February; 159(4):787-96.

110. Daly C J, Milligan C M, Milligan G, Mackenzie J F, McGrath J C. Cellular localisation and pharmacological characterisation of functioning α1-adrenoceptors by fluorescent ligand binding and image analysis reveals identical binding properties of clustered and diffuse populations of receptors. J Pharmacol Exp Ther. 1998; 286:984-990.

111. Masahiro Ono, Hiroyuki Watanabe, Hiroyuki Kimura, Hideo Saji. BODIPY-Based Molecular Probe for Imaging of Cerebral β-Amyloid Plaques. ACS Chem Neurosci. 2012 Apr. 18; 3(4): 319-324.

112. Stevens, L M and Brown R E. Reference and working memory deficits in the 3×TG-AD mouse between 2 and 15 months of age: A cross-sectional study. Behavioural Brain Research 278, 496-505, 2015.

113. Esquerda-Canals G, Montoliu-Gaya L, Güell-Bosch J, Villegas S. Mouse Models of Alzheimer's Disease. J Alzheimers Dis. 2017; 57(4):1171-1183.

114. Piascik M T, Guarino R D, Smith M S, Soltis E E, Saussy D L, Jr, and Perez D M: The specific contribution of the novel $\alpha_{1D}$-adrenoceptor to the contraction of vascular smooth muscle. J Pharmacol Exper Therapeu, 275: 1583-1589, 1995.

115. Hrometz S L, Edelmann S E, McCune D F, Olges J R, Hadley R W, Perez D M, and Piascik M T Expression of multiple $\alpha_1$-adrenergic receptors on vascular smooth muscle: correlation with the regulation of contraction. J Pharmacol Exper Therapeu 290: 452-463, 1999.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A compound of formula (I):

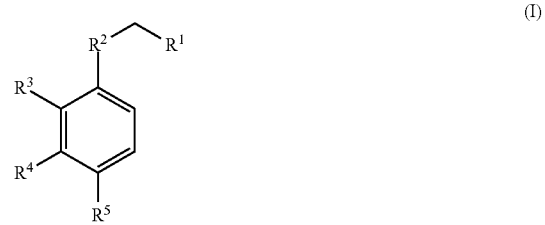

or a pharmaceutically acceptable salt thereof,
wherein:
$R^1$ is a 5-membered heterocyclyl ring having 1, 2, or 3 nitrogen atoms;
$R^2$ is —X—$(CH_2)_m$—, wherein X is selected from —O—, —NH—, —S—, and —$CH_2$—, and wherein m is 0, 1, or 2;
$R^3$ is selected from $C_2$-$C_6$ alkyl, $C_2$-$C_6$ alkenyl, $C_2$-$C_6$ alkynyl, $C_2$-$C_6$ hydroxyalkyl, $C_2$-$C_6$ haloalkyl, $C_2$-$C_6$ hydroxyhaloalkyl, $C_3$-$C_6$ cycloalkyl, aryl, halo, a hydrophobic amino acid moiety, and —$(CHR^a)_n$—$R^6$, wherein:
$R^a$ is selected from hydrogen and hydroxy;
n is 1 or 2; and
$R^6$ is selected from aryl, $C_3$-$C_6$ cycloalkyl, a 3- to 6-membered heterocyclic ring having 1, 2, or 3 heteroatoms selected from O, N, and S;
$R^4$ is selected from —$NR^b$—$SO_2$—$R^7$, —$(CR^cR^d)$—$SO_2$—$R^7$, and —$(CR^eR^f)_p$—$R^8$, wherein:
$R^b$ is selected from hydrogen, $C_1$-$C_3$ alkyl and $C_1$-$C_3$ haloalkyl;
$R^c$ and $R^d$ are each independently selected from hydrogen and methyl, or $R^c$ and $R^d$ are taken together with the carbon atom to which they are attached to form a $C_3$-$C_4$ cycloalkyl group;
$R^e$ and $R^f$ are each independently selected from hydrogen and halo;

p is 0 or 1;

R⁷ is selected from hydrogen, $C_1$-$C_3$ alkyl, $C_1$-$C_3$ haloalkyl, and $C_3$-$C_6$ cycloalkyl; and R⁸ is selected from $C_1$-$C_4$ alkoxy, $C_1$-$C_4$ haloalkoxy, hydroxy, —COOH, —CONH₂, and a 5-membered heteroaryl having 1, 2, or 3 nitrogen atoms; and R⁵ is selected from hydrogen, halo, and any of the groups indicated for R³ and R⁴;

wherein each aryl, heteroaryl, cycloalkyl, and heterocyclyl can be independently unsubstituted or substituted with 1, 2, or 3 substituents independently selected from hydroxy, halo, $C_1$-$C_3$ alkyl, $C_1$-$C_3$ haloalkyl, and oxo.

2. The compound of claim 1, or a pharmaceutically acceptable salt thereof, wherein R¹ is selected from imidazolinyl and imidazolidinyl.

3. The compound of claim 1, or a pharmaceutically acceptable salt thereof, wherein R¹ is 4,5-dihydroimidazol-2-yl.

4. The compound of claim 1, or a pharmaceutically acceptable salt thereof, wherein R² is O.

5. The compound of claim 1, or a pharmaceutically acceptable salt thereof, wherein the compound has formula (Ia):

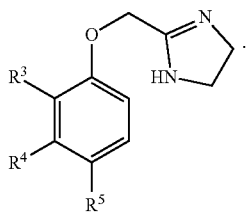

(Ia)

6. The compound of claim 1, or a pharmaceutically acceptable salt thereof, wherein R³ is selected from $C_2$-$C_6$ alkyl, $C_2$-$C_6$ hydroxyalkyl, $C_2$-$C_6$ haloalkyl, $C_2$-$C_6$ hydroxyhaloalkyl, halo, and —(CHR$^a$)$_n$—R⁶.

7. The compound of claim 1, or a pharmaceutically acceptable salt thereof, wherein R³ is isobutyl.

8. The compound of claim 1, or a pharmaceutically acceptable salt thereof, wherein R⁴ is —NR$^b$—SO₂—R⁷ or —(CR$^c$R$^d$)—SO₂—R⁷.

9. The compound of claim 8, or a pharmaceutically acceptable salt thereof, wherein R⁴ is —NR$^b$—SO₂—R⁷, R$^b$ is $C_1$-$C_3$ alkyl, and R⁷ is hydrogen or $C_1$-$C_3$ alkyl.

10. The compound of claim 9, or a pharmaceutically acceptable salt thereof, wherein R⁴ is —N(CH₃)—SO₂—CH₃.

11. The compound of claim 1, or a pharmaceutically acceptable salt thereof, wherein R⁵ is selected from hydrogen and halo.

12. The compound of claim 11, or a pharmaceutically acceptable salt thereof, wherein R⁵ is hydrogen.

13. The compound of claim 1, wherein the compound is selected from:

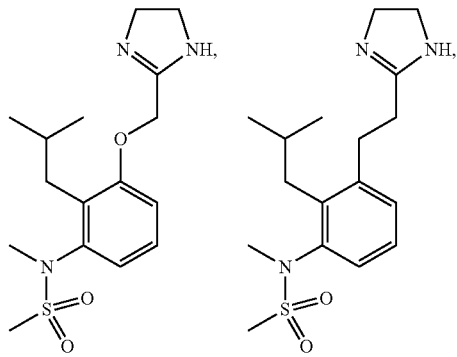 [SMILES: CC(C)Cc1c(OCC2=NCCN2)cccc1N(C)S(C)(=O)=O ; CC(C)Cc1c(CCC2=NCCN2)cccc1N(C)S(C)(=O)=O]

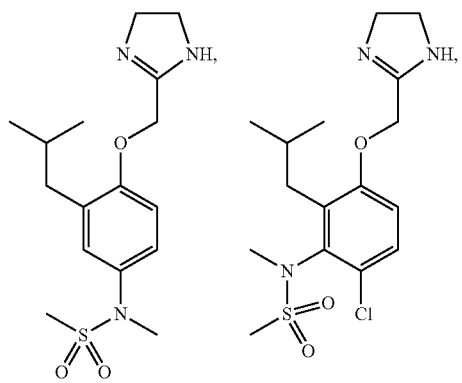

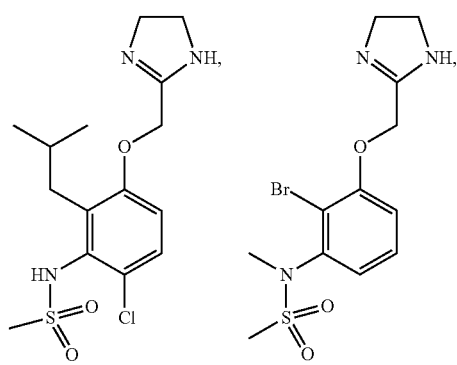

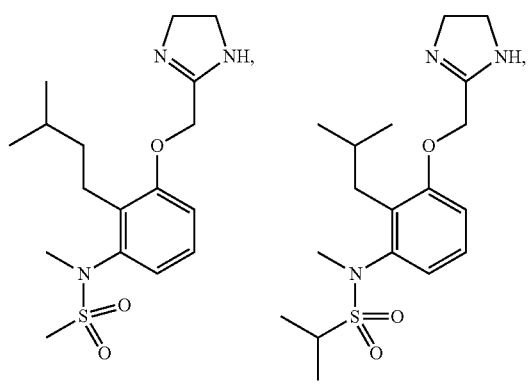

-continued

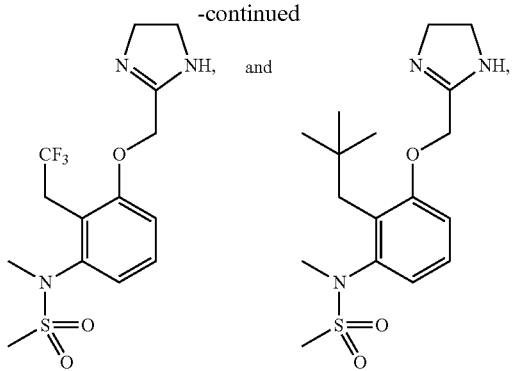

or a pharmaceutically acceptable salt thereof.

14. The compound of claim 1, wherein the compound is not in a salt form.

15. The compound of claim 1, wherein the compound is in the form of a pharmaceutically acceptable salt.

16. The compound of claim 15, wherein the compound is in the form of a hydrochloride salt.

17. A method of treating a disorder in a subject, comprising: treating the subject with a compound of claim 1, wherein the disorder is selected from the group consisting of: benign prostatic hyperplasia, Alzheimer's disease, memory loss, cognitive decline, depression, depressed mood, diabetes, seizures, neurodegeneration, Parkinson's disease, autonomic failure, Multiple System Atrophy, amyotrophic lateral sclerosis (ALS), Huntington's disease, heart failure, cardiovascular disease, and Multiple Sclerosis.

18. The method of claim 17, wherein said treating causes at least one of the following: improved memory, reduced depression, increased mood, increased metabolism, prolonged lifespan, arousal, satiety, and reduced seizures.

19. The method of claim 17, wherein said subject has Alzheimer's disease.

20. A method of treating loss of bladder control in a subject, comprising treating the subject with a compound of claim 1.

* * * * *